(12) United States Patent
Calloway et al.

(10) Patent No.: US 11,607,277 B2
(45) Date of Patent: Mar. 21, 2023

(54) REGISTRATION OF SURGICAL TOOL WITH REFERENCE ARRAY TRACKED BY CAMERAS OF AN EXTENDED REALITY HEADSET FOR ASSISTED NAVIGATION DURING SURGERY

(71) Applicant: GLOBUS MEDICAL, INC., Audubon, PA (US)

(72) Inventors: Thomas Calloway, Pelham, NH (US); Isaac Dulin, Somerville, MA (US)

(73) Assignee: Globus Medical, Inc., Audubon, PA (US)

(*) Notice: Subject to any disclaimer, the term of this patent is extended or adjusted under 35 U.S.C. 154(b) by 0 days.

(21) Appl. No.: 16/861,741

(22) Filed: Apr. 29, 2020

(65) Prior Publication Data

US 2021/0338337 A1   Nov. 4, 2021

(51) Int. Cl.
*A61B 34/20* (2016.01)
*G06F 3/01* (2006.01)
*G06T 7/20* (2017.01)
*G06T 11/00* (2006.01)
*A61B 34/30* (2016.01)
*A61B 90/00* (2016.01)
(Continued)

(52) U.S. Cl.
CPC .............. *A61B 34/20* (2016.02); *G06F 3/011* (2013.01); *G06T 7/20* (2013.01); *G06T 11/00* (2013.01); *A61B 34/30* (2016.02); *A61B 2034/2057* (2016.02); *A61B 2034/2072* (2016.02); *A61B 2090/363* (2016.02); *A61B 2090/365* (2016.02); *A61B 2090/3764* (2016.02); *A61B 2090/502* (2016.02); *G02B 27/0172* (2013.01); *G02B 2027/0138* (2013.01); *G06T 2200/24* (2013.01); *G06T 2207/30244* (2013.01)

(58) Field of Classification Search
CPC ................................ A61B 34/20; G06F 3/011
See application file for complete search history.

(56) References Cited

U.S. PATENT DOCUMENTS

| | | |
|---|---|---|
| 4,722,056 A | 1/1988 | Roberts et al. |
| 5,526,812 A | 6/1996 | Dumoulin et al. |
| 5,740,802 A | 4/1998 | Nafis et al. |

(Continued)

FOREIGN PATENT DOCUMENTS

| | | |
|---|---|---|
| EP | 3025665 A1 | 6/2016 |
| JP | 2018529399 A | 10/2018 |

(Continued)

*Primary Examiner* — Yi Yang

(57) ABSTRACT

A camera tracking system is disclosed for computer assisted navigation during surgery. The camera tracking system is configured to identify a reference array tracked by a set of tracking cameras attached to an extended reality (XR) headset, and determine whether the reference array is registered as being paired with characteristics of one of a plurality of surgical tools defined in a surgical tool database. The camera tracking system is further configured to, based on the reference array being determined to not be registered and receiving user input, register the reference array to be paired with characteristics of one of the plurality of surgical tools selected based on the user input. The camera tracking system is further configured to provide a representation of the characteristics to a display device of the XR headset for display to the user.

18 Claims, 23 Drawing Sheets

(51) Int. Cl.
*A61B 90/50* (2016.01)
*G02B 27/01* (2006.01)

(56) References Cited

U.S. PATENT DOCUMENTS

| | | |
|---|---|---|
| 5,961,456 A | 10/1999 | Gildenberg |
| 6,226,548 B1 | 5/2001 | Foley et al. |
| 6,301,495 B1 | 10/2001 | Gueziec et al. |
| 6,349,001 B1 | 2/2002 | Spitzer |
| 6,503,195 B1 | 1/2003 | Keller et al. |
| 6,544,176 B2 | 4/2003 | Mikus et al. |
| 6,614,453 B1 | 9/2003 | Suri et al. |
| 6,669,635 B2 | 12/2003 | Kessman et al. |
| 6,725,080 B2 | 4/2004 | Melkent et al. |
| 6,856,324 B2 | 2/2005 | Sauer et al. |
| 6,867,753 B2 | 3/2005 | Chinthammit et al. |
| 6,919,867 B2 | 7/2005 | Sauer |
| 6,920,347 B2 | 7/2005 | Simon et al. |
| 6,947,786 B2 | 9/2005 | Simon et al. |
| 7,050,845 B2 | 5/2006 | Vilsmeier |
| 7,176,936 B2 | 2/2007 | Sauer et al. |
| 7,480,402 B2 | 1/2009 | Bar-Zohar et al. |
| 7,493,153 B2 | 2/2009 | Ahmed et al. |
| 7,542,791 B2 | 6/2009 | Mire et al. |
| 7,570,791 B2 | 8/2009 | Frank et al. |
| 7,599,730 B2 | 10/2009 | Hunter et al. |
| 7,605,826 B2 | 10/2009 | Sauer |
| 7,606,613 B2 | 10/2009 | Simon et al. |
| 7,774,044 B2 | 8/2010 | Sauer et al. |
| 7,831,294 B2 | 11/2010 | Viswanathan |
| 7,835,778 B2 | 11/2010 | Foley et al. |
| 7,953,470 B2 | 5/2011 | Vetter et al. |
| 7,987,001 B2 | 7/2011 | Teichman et al. |
| 8,106,905 B2 | 1/2012 | Markowitz et al. |
| 8,123,675 B2 | 2/2012 | Funda et al. |
| 8,228,368 B2 | 7/2012 | Zhao et al. |
| 8,314,815 B2 | 11/2012 | Navab et al. |
| 8,325,873 B2 | 12/2012 | Helm et al. |
| 8,358,818 B2 | 1/2013 | Miga et al. |
| 8,374,673 B2 | 2/2013 | Adcox et al. |
| 8,427,527 B2 | 4/2013 | Visser et al. |
| 8,504,136 B1 | 8/2013 | Sun et al. |
| 8,509,503 B2 | 8/2013 | Nahum et al. |
| 8,532,741 B2 | 9/2013 | Heruth et al. |
| 8,660,635 B2 | 2/2014 | Simon et al. |
| 8,672,836 B2 | 3/2014 | Higgins et al. |
| 8,700,123 B2 | 4/2014 | Okamura et al. |
| 8,774,363 B2 | 7/2014 | Van Den Houten et al. |
| 8,784,443 B2 | 7/2014 | Tripathi |
| 8,842,893 B2 | 9/2014 | Teichman et al. |
| 8,878,900 B2 | 11/2014 | Yang et al. |
| 8,891,847 B2 | 11/2014 | Helm et al. |
| 8,938,283 B2 | 1/2015 | Zentgraf et al. |
| 8,938,301 B2 | 1/2015 | Hagedorn |
| 8,945,140 B2 | 2/2015 | Hubschman et al. |
| 8,948,935 B1 | 2/2015 | Peeters et al. |
| 9,095,252 B2 | 8/2015 | Popovic |
| 9,105,207 B2 | 8/2015 | Leung |
| 9,119,670 B2 | 9/2015 | Yang et al. |
| 9,123,155 B2 | 9/2015 | Cunningham et al. |
| 9,232,982 B2 | 1/2016 | Soler et al. |
| 9,265,468 B2 | 2/2016 | Rai et al. |
| 9,289,267 B2 | 3/2016 | Sauer et al. |
| 9,295,435 B2 | 3/2016 | Florent et al. |
| 9,333,361 B2 | 5/2016 | Li et al. |
| 9,436,993 B1 | 9/2016 | Stolka et al. |
| 9,439,556 B2 | 9/2016 | Pandya et al. |
| 9,492,241 B2 | 11/2016 | Jaskowicz et al. |
| 9,498,132 B2 | 11/2016 | Maier-Hein et al. |
| 9,538,962 B1 | 1/2017 | Hannaford et al. |
| 9,547,940 B1 | 1/2017 | Sun et al. |
| 9,554,866 B2 | 1/2017 | Cunningham et al. |
| 9,563,266 B2 | 2/2017 | Banerjee et al. |
| 9,576,106 B2 | 2/2017 | Ahmad |
| 9,626,805 B2 | 4/2017 | Lampotang et al. |
| 9,645,379 B2 | 5/2017 | Ren et al. |
| 9,681,925 B2 | 6/2017 | Azar et al. |
| 9,707,400 B2 | 7/2017 | Grenz et al. |
| 9,767,608 B2 | 9/2017 | Lee et al. |
| 9,773,312 B2 | 9/2017 | Lee |
| 9,788,756 B2 | 10/2017 | Demmer |
| 9,795,282 B2 | 10/2017 | Sholev et al. |
| 9,833,254 B1 | 12/2017 | Barral et al. |
| 9,835,862 B1 | 12/2017 | Zhou et al. |
| 9,839,365 B1 | 12/2017 | Homyk et al. |
| 9,855,103 B2 | 1/2018 | Tsekos et al. |
| 9,892,564 B1 | 2/2018 | Cvetko et al. |
| 9,895,063 B1 | 2/2018 | Hannaford et al. |
| 9,898,662 B2 | 2/2018 | Tsuda et al. |
| 9,911,187 B2 | 3/2018 | Steinle et al. |
| 9,925,013 B2 | 3/2018 | Dell et al. |
| 9,928,629 B2 | 3/2018 | Benishti et al. |
| 9,931,040 B2 | 4/2018 | Homyk et al. |
| 9,949,637 B1 | 4/2018 | Wong et al. |
| 9,970,955 B1 | 5/2018 | Homyk et al. |
| 9,980,698 B2 | 5/2018 | Bakker et al. |
| 10,010,373 B2 | 7/2018 | Canfield et al. |
| 10,010,379 B1 | 7/2018 | Gibby et al. |
| 10,013,808 B2 | 7/2018 | Jones et al. |
| 10,016,243 B2 | 7/2018 | Esterberg |
| 10,052,170 B2 | 8/2018 | Saget et al. |
| 10,073,515 B2 | 9/2018 | Awdeh |
| 10,092,164 B2 | 10/2018 | Sholev et al. |
| 10,092,237 B2 | 10/2018 | Wong et al. |
| 10,092,361 B2 | 10/2018 | Ferro et al. |
| 10,105,187 B2 | 10/2018 | Corndorf et al. |
| 10,152,789 B2 | 12/2018 | Carnes et al. |
| 10,152,796 B2 | 12/2018 | Guo et al. |
| 10,154,239 B2 | 12/2018 | Casas |
| 10,163,252 B2 | 12/2018 | Yun et al. |
| 10,166,019 B2 | 1/2019 | Nawana et al. |
| 10,176,642 B2 | 1/2019 | Tran et al. |
| 10,191,615 B2 | 1/2019 | Helm et al. |
| 10,194,990 B2 | 2/2019 | Amanatullah et al. |
| 10,195,076 B2 | 2/2019 | Fateh |
| 10,197,803 B2 | 2/2019 | Badiali et al. |
| 10,197,816 B2 | 2/2019 | Waisman et al. |
| 10,226,298 B2 | 3/2019 | Ourselin et al. |
| 10,231,784 B2 | 3/2019 | Hettrick et al. |
| 10,235,737 B2 | 3/2019 | Cheatham, III et al. |
| 10,242,292 B2 | 3/2019 | Zisimopoulos et al. |
| 10,251,714 B2 | 4/2019 | Carnes et al. |
| 10,258,426 B2 | 4/2019 | Silva et al. |
| 10,265,138 B2 | 4/2019 | Choudhry et al. |
| 10,275,927 B2 | 4/2019 | Kuhn et al. |
| 10,278,726 B2 | 5/2019 | Barth et al. |
| 10,285,765 B2 | 5/2019 | Sachs et al. |
| 10,292,780 B2 | 5/2019 | Park |
| 10,360,730 B2 | 7/2019 | Hasegwa |
| 10,366,489 B2 | 7/2019 | Boettger et al. |
| 10,376,318 B2 | 8/2019 | Tsusaka et al. |
| 10,379,048 B2 | 8/2019 | Wang et al. |
| 10,383,654 B2 | 8/2019 | Yilmaz et al. |
| 10,390,780 B2 | 8/2019 | Han et al. |
| 10,390,890 B2 | 8/2019 | Jagga |
| 10,390,891 B2 | 8/2019 | Govari et al. |
| 10,398,514 B2 | 9/2019 | Ryan et al. |
| 10,405,927 B1 | 9/2019 | Lang |
| 10,412,377 B2 | 9/2019 | Forthmann et al. |
| 10,413,363 B2 | 9/2019 | Fahim et al. |
| 10,426,339 B2 | 10/2019 | Papac |
| 10,426,345 B2 | 10/2019 | Shekhar et al. |
| 10,426,554 B2 | 10/2019 | Siewerdsen et al. |
| 10,431,008 B2 | 10/2019 | Djajadiningrat et al. |
| 10,432,913 B2 | 10/2019 | Shokri et al. |
| 10,433,915 B2 | 10/2019 | Isaacs et al. |
| 10,448,003 B2 | 10/2019 | Gafenberg |
| 2003/0179308 A1 | 9/2003 | Zamorano et al. |
| 2003/0210812 A1 | 11/2003 | Khamene et al. |
| 2004/0254454 A1 | 12/2004 | Kockro |
| 2005/0054910 A1 | 3/2005 | Tremblay et al. |
| 2005/0215879 A1 | 9/2005 | Chuanggui |
| 2005/0267354 A1* | 12/2005 | Marquart ............ A61B 90/36 600/411 |

(56) References Cited

U.S. PATENT DOCUMENTS

| | | |
|---|---|---|
| 2006/0176242 A1 | 8/2006 | Jaramaz et al. |
| 2006/0293557 A1 | 12/2006 | Chuanggui et al. |
| 2007/0021738 A1 | 1/2007 | Hasset et al. |
| 2007/0167702 A1 | 7/2007 | Hasser et al. |
| 2007/0236514 A1 | 10/2007 | Agusanto et al. |
| 2007/0238981 A1 | 10/2007 | Zhu et al. |
| 2007/0248261 A1 | 10/2007 | Zhou et al. |
| 2008/0123910 A1 | 5/2008 | Zhu |
| 2008/0183068 A1 | 7/2008 | Carls et al. |
| 2008/0183074 A1 | 7/2008 | Carls et al. |
| 2008/0183188 A1 | 7/2008 | Carls et al. |
| 2008/0243142 A1 | 10/2008 | Gildenberg |
| 2010/0210902 A1 | 8/2010 | Navab et al. |
| 2011/0306986 A1 | 12/2011 | Lee et al. |
| 2012/0059378 A1 | 3/2012 | Farrell |
| 2012/0203067 A1 | 8/2012 | Higgins et al. |
| 2012/0302875 A1 | 11/2012 | Kohring |
| 2013/0211232 A1 | 8/2013 | Murphy et al. |
| 2013/0267838 A1 | 10/2013 | Fronk et al. |
| 2013/0274596 A1 | 10/2013 | Azizian et al. |
| 2014/0022283 A1 | 1/2014 | Chan et al. |
| 2014/0044333 A1 | 2/2014 | Barth, Jr. et al. |
| 2014/0139405 A1 | 5/2014 | Ribble et al. |
| 2014/0206994 A1 | 7/2014 | Jain et al. |
| 2014/0347353 A1 | 11/2014 | Popovic et al. |
| 2015/0031990 A1 | 1/2015 | Boctor et al. |
| 2015/0073265 A1 | 3/2015 | Popovic et al. |
| 2015/0084990 A1 | 3/2015 | Laor |
| 2015/0085979 A1* | 3/2015 | Zheng ................ G06K 9/6203 |
| | | 378/62 |
| 2015/0112126 A1 | 4/2015 | Popovic et al. |
| 2015/0146946 A1 | 5/2015 | Elhawary et al. |
| 2015/0201892 A1 | 7/2015 | Hummel et al. |
| 2015/0230689 A1 | 8/2015 | Blohm et al. |
| 2015/0238276 A1 | 8/2015 | Atarot et al. |
| 2015/0248793 A1 | 9/2015 | Abovitz et al. |
| 2015/0305828 A1 | 10/2015 | Park et al. |
| 2015/0366628 A1 | 12/2015 | Ingmanson |
| 2016/0015469 A1 | 1/2016 | Goshayesh et al. |
| 2016/0015470 A1 | 1/2016 | Border |
| 2016/0018640 A1 | 1/2016 | Haddick et al. |
| 2016/0018641 A1 | 1/2016 | Haddick et al. |
| 2016/0018642 A1 | 1/2016 | Haddick et al. |
| 2016/0019715 A1 | 1/2016 | Haddick et al. |
| 2016/0019716 A1 | 1/2016 | Huang et al. |
| 2016/0019719 A1 | 1/2016 | Osterhout et al. |
| 2016/0021304 A1 | 1/2016 | Osterhout |
| 2016/0022125 A1 | 1/2016 | Nicolau et al. |
| 2016/0086380 A1 | 3/2016 | Vayser et al. |
| 2016/0163105 A1 | 6/2016 | Hong et al. |
| 2016/0249989 A1 | 9/2016 | Devam et al. |
| 2016/0287337 A1 | 10/2016 | Aram et al. |
| 2016/0317119 A1 | 11/2016 | Tahmasebi Maraghoosh et al. |
| 2016/0324598 A1 | 11/2016 | Bothorel et al. |
| 2016/0360117 A1 | 12/2016 | Elefteriu et al. |
| 2017/0035517 A1 | 2/2017 | Geri et al. |
| 2017/0053437 A1 | 2/2017 | Ye et al. |
| 2017/0099479 A1 | 4/2017 | Browd et al. |
| 2017/0119471 A1 | 5/2017 | Winner et al. |
| 2017/0119474 A1 | 5/2017 | Kronman |
| 2017/0151034 A1 | 6/2017 | Oda et al. |
| 2017/0172381 A1 | 6/2017 | Morimoto |
| 2017/0172663 A1 | 6/2017 | Popovic et al. |
| 2017/0202624 A1 | 7/2017 | Atarot et al. |
| 2017/0202633 A1 | 7/2017 | Liu |
| 2017/0224427 A1 | 8/2017 | Lavallee et al. |
| 2017/0231714 A1 | 8/2017 | Kosmecki et al. |
| 2017/0238996 A1 | 8/2017 | Frame et al. |
| 2017/0251900 A1 | 9/2017 | Hansen et al. |
| 2017/0256095 A1 | 9/2017 | Bani-Hashemi |
| 2017/0273549 A1 | 9/2017 | Nazareth et al. |
| 2017/0296292 A1 | 10/2017 | Mahmood et al. |
| 2017/0315364 A1 | 11/2017 | Masumoto |
| 2017/0322410 A1 | 11/2017 | Watson et al. |
| 2017/0323062 A1 | 11/2017 | Djajadiningrat et al. |
| 2017/0336870 A1 | 11/2017 | Everett et al. |
| 2017/0367766 A1 | 12/2017 | Mahfouz |
| 2017/0367771 A1 | 12/2017 | Tako et al. |
| 2018/0014379 A1* | 1/2018 | Carvalho ................ G06F 3/017 |
| 2018/0021099 A1 | 1/2018 | Warner et al. |
| 2018/0032130 A1 | 2/2018 | Meglan |
| 2018/0042692 A1 | 2/2018 | Kim et al. |
| 2018/0049809 A1 | 2/2018 | Marti et al. |
| 2018/0071032 A1 | 3/2018 | De Almeida Barreto |
| 2018/0078316 A1 | 3/2018 | Schaewe et al. |
| 2018/0082480 A1 | 3/2018 | White et al. |
| 2018/0092698 A1 | 4/2018 | Chopra et al. |
| 2018/0092706 A1 | 4/2018 | Anderson et al. |
| 2018/0116724 A1 | 5/2018 | Gmeiner et al. |
| 2018/0116732 A1 | 5/2018 | Lin et al. |
| 2018/0125586 A1 | 5/2018 | Sela et al. |
| 2018/0140362 A1 | 5/2018 | Cali et al. |
| 2018/0158201 A1 | 6/2018 | Thompson et al. |
| 2018/0161102 A1 | 6/2018 | Wei et al. |
| 2018/0168730 A1 | 6/2018 | Nazy |
| 2018/0168741 A1 | 6/2018 | Swayze |
| 2018/0168769 A1 | 6/2018 | Wood et al. |
| 2018/0185100 A1 | 7/2018 | Weinstein et al. |
| 2018/0220100 A1 | 8/2018 | Ovchinnikov et al. |
| 2018/0228555 A1 | 8/2018 | Charron et al. |
| 2018/0232925 A1 | 8/2018 | Frakes et al. |
| 2018/0233222 A1 | 8/2018 | Daley et al. |
| 2018/0235739 A1 | 8/2018 | Jahn |
| 2018/0247449 A1 | 8/2018 | Park et al. |
| 2018/0249912 A1 | 9/2018 | Schneider et al. |
| 2018/0256256 A1 | 9/2018 | May et al. |
| 2018/0263698 A1 | 9/2018 | Wang et al. |
| 2018/0263727 A1 | 9/2018 | Pellerito |
| 2018/0289428 A1 | 10/2018 | Lee et al. |
| 2018/0289983 A1 | 10/2018 | Fishman |
| 2018/0299675 A1 | 10/2018 | Benz et al. |
| 2018/0303377 A1 | 10/2018 | West et al. |
| 2018/0303558 A1 | 10/2018 | Thomas |
| 2018/0303667 A1 | 10/2018 | Peyman |
| 2018/0310811 A1 | 11/2018 | Meglan et al. |
| 2018/0310831 A1 | 11/2018 | Cheng et al. |
| 2018/0310875 A1 | 11/2018 | Meglan et al. |
| 2018/0325604 A1 | 11/2018 | Atarot et al. |
| 2018/0325618 A1 | 11/2018 | Justin et al. |
| 2018/0333073 A1 | 11/2018 | Hill et al. |
| 2018/0333207 A1 | 11/2018 | Moctezuma De La Barrera |
| 2018/0333208 A1 | 11/2018 | Kotian et al. |
| 2018/0344266 A1 | 12/2018 | Altmann |
| 2018/0344408 A1 | 12/2018 | Rotilio et al. |
| 2018/0357825 A1 | 12/2018 | Hoffmann et al. |
| 2018/0360310 A1 | 12/2018 | Berlin |
| 2018/0368930 A1 | 12/2018 | Esterberg et al. |
| 2019/0000564 A1 | 1/2019 | Navab et al. |
| 2019/0000570 A1 | 1/2019 | Esterberg et al. |
| 2019/0008592 A1 | 1/2019 | Thienphrapa et al. |
| 2019/0011709 A1 | 1/2019 | Yadav et al. |
| 2019/0015162 A1 | 1/2019 | Abhari et al. |
| 2019/0015167 A1 | 1/2019 | Draelos et al. |
| 2019/0029757 A1 | 1/2019 | Roh et al. |
| 2019/0035156 A1 | 1/2019 | Wei et al. |
| 2019/0038362 A1 | 2/2019 | Nash et al. |
| 2019/0046232 A1* | 2/2019 | Tokuda ................ A61B 17/3403 |
| 2019/0046276 A1* | 2/2019 | Inglese ................ A61C 9/0046 |
| 2019/0050665 A1 | 2/2019 | Sakuragi |
| 2019/0053851 A1 | 2/2019 | Siemionow et al. |
| 2019/0053855 A1 | 2/2019 | Siemionow et al. |
| 2019/0053858 A1 | 2/2019 | Kapoo et al. |
| 2019/0054632 A1 | 2/2019 | Grafenberg et al. |
| 2019/0059773 A1 | 2/2019 | Laughlin et al. |
| 2019/0066260 A1 | 2/2019 | Suehling et al. |
| 2019/0066390 A1 | 2/2019 | Vogel et al. |
| 2019/0069962 A1 | 3/2019 | Tabandeh et al. |
| 2019/0076194 A1 | 3/2019 | Jang |
| 2019/0080515 A1 | 3/2019 | Geri et al. |
| 2019/0088162 A1 | 3/2019 | Meglan |
| 2019/0090955 A1 | 3/2019 | Singh et al. |
| 2019/0099221 A1 | 4/2019 | Schmidt et al. |
| 2019/0099225 A1 | 4/2019 | Todd et al. |
| 2019/0104919 A1 | 4/2019 | Shelton, IV et al. |

(56) References Cited

U.S. PATENT DOCUMENTS

| | | |
|---|---|---|
| 2019/0108654 A1 | 4/2019 | Lasserre et al. |
| 2019/0117190 A1 | 4/2019 | Djajadonongrat |
| 2019/0122443 A1 | 4/2019 | Stocker |
| 2019/0125361 A1 | 5/2019 | Shelton, IV et al. |
| 2019/0125454 A1 | 5/2019 | Shelton, IV et al. |
| 2019/0142520 A1 | 5/2019 | Vandyken |
| 2019/0159841 A1 | 5/2019 | Abhari et al. |
| 2019/0167148 A1 | 6/2019 | Durfee et al. |
| 2019/0175058 A1 | 6/2019 | Godwin et al. |
| 2019/0180441 A1 | 6/2019 | Peng et al. |
| 2019/0183576 A1 | 6/2019 | Fahim et al. |
| 2019/0183590 A1 | 6/2019 | Hladio et al. |
| 2019/0192230 A1 * | 6/2019 | Siemionow .......... A61B 90/39 |
| 2019/0192232 A1 | 6/2019 | Altmann et al. |
| 2019/0200844 A1 | 7/2019 | Shelton, IV et al. |
| 2019/0200977 A1 | 7/2019 | Shelton, IV et al. |
| 2019/0201104 A1 | 7/2019 | Shelton, IV et al. |
| 2019/0201106 A1 | 7/2019 | Siemionow et al. |
| 2019/0201158 A1 | 7/2019 | Shelton, IV et al. |
| 2019/0206062 A1 | 7/2019 | Matsuoka et al. |
| 2019/0206134 A1 | 7/2019 | Devam et al. |
| 2019/0206565 A1 | 7/2019 | Shelton, IV |
| 2019/0209241 A1 | 7/2019 | Begg |
| 2019/0214126 A1 | 7/2019 | Goeiz |
| 2019/0216572 A1 | 7/2019 | Wang et al. |
| 2019/0223746 A1 | 7/2019 | Intrator |
| 2019/0231220 A1 | 8/2019 | Refai et al. |
| 2019/0231443 A1 | 8/2019 | Mcginley et al. |
| 2019/0239850 A1 | 8/2019 | Dalvin et al. |
| 2019/0251551 A1 * | 8/2019 | Mousavi .................. H04L 9/30 |
| 2019/0254753 A1 | 8/2019 | Johnson et al. |
| 2019/0274762 A1 | 9/2019 | Kim et al. |
| 2019/0282099 A1 | 9/2019 | Themelis |
| 2019/0307516 A1 | 10/2019 | Schotzko et al. |
| 2019/0369717 A1 * | 12/2019 | Frielinghaus .......... G06F 3/012 |

FOREIGN PATENT DOCUMENTS

| | | |
|---|---|---|
| JP | 201930385 A | 2/2019 |
| WO | 2015143508 A1 | 10/2015 |

* cited by examiner

US 11,607,277 B2

REGISTRATION OF SURGICAL TOOL WITH REFERENCE ARRAY TRACKED BY CAMERAS OF AN EXTENDED REALITY HEADSET FOR ASSISTED NAVIGATION DURING SURGERY

FIELD

The present disclosure relates to medical devices and systems, and more particularly, camera tracking systems used for computer assisted navigation during surgery.

BACKGROUND

Computer assisted navigation during surgery can provide a surgeon with computerized visualization of the present pose of a surgical tool relative to medical images of a patient's anatomy. Camera tracking systems for computer assisted navigation typically use a set of cameras to track a set of fiducials attached to a surgical tool which is being positioned by a surgeon or other user during surgery. The set of fiducials, also referred to as a dynamic reference array or dynamic reference base (DRB) allows the camera tracking system to determine a pose of the surgical tool relative to anatomical structure within a medical image and relative to patient for display to the surgeon. The surgeon can thereby use the real-time pose feedback to navigate the surgical tool during a surgical procedure.

Extended reality (XR) headsets are being combined with camera tracking systems to enable surgeons to see the real-time pose feedback as graphical objects overlaid on the patient. There is a continuing need to enable a surgeon wearing an XR headset to be able to work with a myriad of types of surgical tools while reducing error in tool selection and while reducing interruption of a surgeon's concentration during a surgical procedure.

SUMMARY

Various embodiments disclosed herein are directed to improvements in computer assisted navigation during surgery. A XR headset is used to assist with registering characteristics of a surgical tool with a reference array that is identified by a camera tracking system. A representation of the characteristics can be displayed to the XR headset to enable the user to confirm correctness of the registration process. Using the XR headset during the registration process can provide a more intuitive, time efficient and reliable process for surgeons and other medical personnel (users) to register surgical tools with a camera tracking system before and/or during a surgical procedure.

In one embodiment, a camera tracking system for computer assisted navigation during surgery is configured to identify a reference array which is being tracked by a set of tracking cameras attached to an XR headset. The camera tracking system determines whether the reference array is registered as being paired with characteristics of one of a plurality of surgical tools defined in a surgical tool database. Based on the reference array being determined to not be registered and receiving user input, the camera tracking system registers the reference array as paired with characteristics of one of the plurality of surgical tools selected based on the user input. The camera tracking system then provides a representation of the characteristics to a display device of the XR headset for display to the user.

Related computer program products for and methods by a camera tracking system are disclosed.

Other camera tracking systems, computer program products, and methods according to embodiments will be or become apparent to one with skill in the art upon review of the following drawings and detailed description. It is intended that all such camera tracking systems, computer program products, and methods be included within this description, be within the scope of the present disclosure, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings.

DETAILED DESCRIPTION

Inventive concepts will now be described more fully hereinafter with reference to the accompanying drawings, in which examples of embodiments of inventive concepts are shown. Inventive concepts may, however, be embodied in many different forms and should not be construed as limited to the embodiments set forth herein. Rather, these embodiments are provided so that this disclosure will be thorough and complete, and will fully convey the scope of various present inventive concepts to those skilled in the art. It should also be noted that these embodiments are not mutually exclusive. Components from one embodiment may be tacitly assumed to be present or used in another embodiment.

Various embodiments disclosed herein are directed to improvements in computer assisted navigation during surgery. An extended reality (XR) headset is operatively connected to the surgical system and configured to provide an interactive environment through which a surgeon, assistant, and/or other personnel can view and select among patient images, view and select among computer generated surgery navigation information, and/or control surgical equipment in the operating room. As will be explained below, the XR headset may be configured to augment a real-world scene with computer generated XR images. The XR headset may be configured to provide an augmented reality (AR) viewing environment by displaying the computer generated XR images on a see-through display screen that allows light from the real-world scene to pass therethrough for combined viewing by the user. Alternatively, the XR headset may be configured to provide a virtual reality (VR) viewing environment by preventing or substantially preventing light from the real-world scene from being directly viewed by the user while the user is viewing the computer generated AR images on a display screen. An XR headset can be configured to provide both AR and VR viewing environments. In one embodiment, both AR and VR viewing environments are provided by lateral bands of substantially differing opacity arranged between the see-through display screen and the real-world scene, so that a VR viewing environment is provided for XR images aligned with a high opacity band and an AR viewing environment is provided for XR images aligned with the low opacity band. In another embodiment, both AR and VR viewing environments are provided by computer adjustable control of an opacity filter that variably constrains how much light from the real-world scene passes through a see-through display screen for combining with the XR images viewed by the user. Thus, the XR headset can also be referred to as an AR headset or a VR headset.

Figure 1:
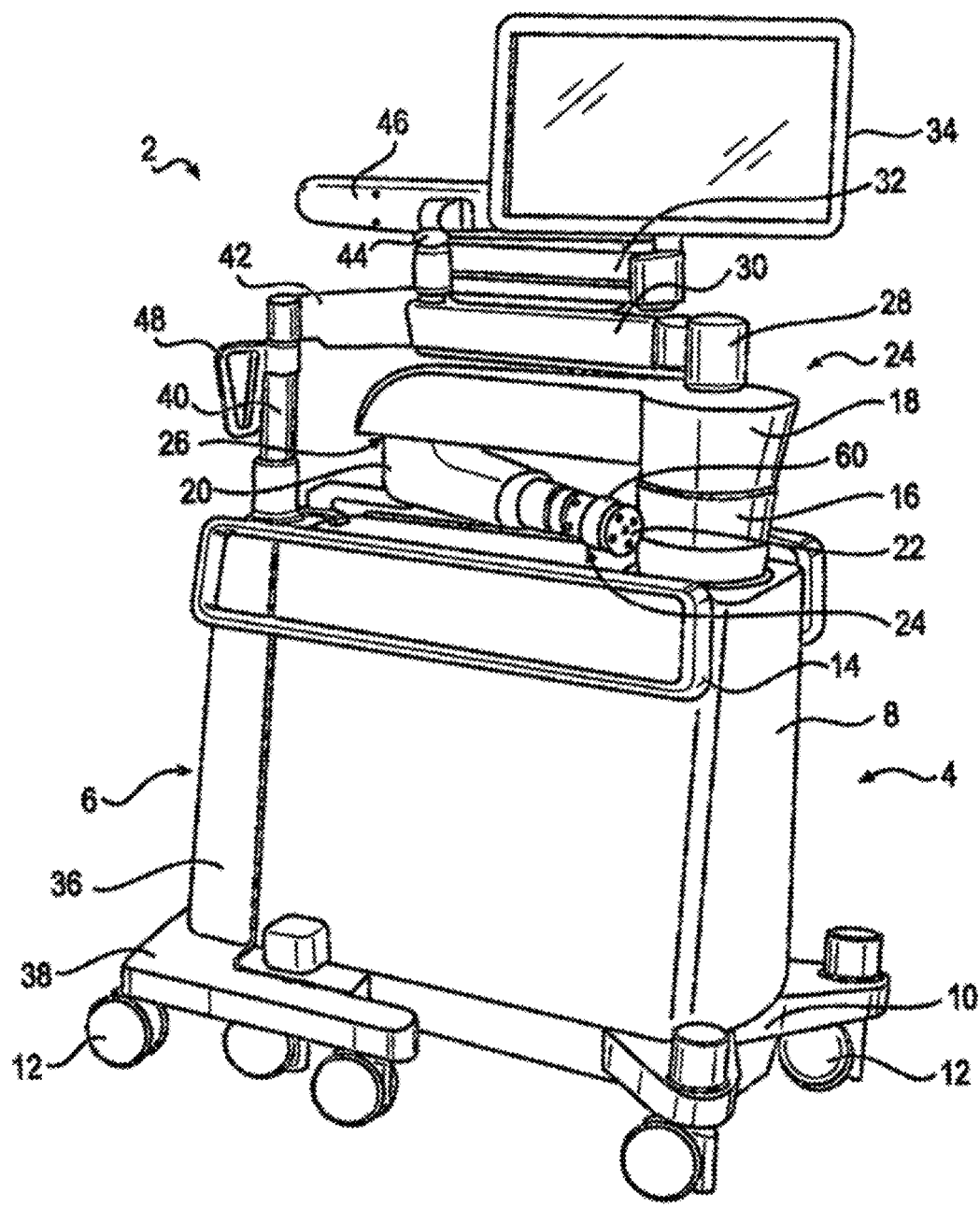
FIG. 1 illustrates an embodiment of a surgical system according to some embodiments of the present disclosure.

FIG. 1 illustrates an embodiment of a surgical system 2 according to some embodiments of the present disclosure. Prior to performance of an orthopedic or other surgical procedure, a three-dimensional ("3D") image scan may be taken of a planned surgical area of a patient using, e.g., the C-Arm imaging device 104 of FIG. 10 or O-Arm imaging device 106 of FIG. 11, or from another medical imaging device such as a computed tomography (CT) image or MRI. This scan can be taken pre-operatively (e.g. few weeks before procedure, most common) or intra-operatively. However, any known 3D or 2D image scan may be used in accordance with various embodiments of the surgical system 2. The image scan is sent to a computer platform in communication with the surgical system 2, such as the computer platform 910 of the surgical system 900 (FIG. 9) which may include the camera tracking system component 6, the surgical robot 4 (e.g., robot 2 in FIG. 1), imaging devices (e.g., C-Arm 104, O-Arm 106, etc.), and an image database 950 for storing image scans of patients. A surgeon reviewing the image scan(s) on a display device of the computer platform 910 (FIG. 9) generates a surgical plan defining a target pose for a surgical tool to be used during a surgical procedure on an anatomical structure of the patient. Example surgical tools, also referred to as tools, can include, without limitation, drills, screw drivers, saws, retractors, and implants such as a screws, spacers, interbody fusion devices, plates, rods, etc. In some embodiments, the surgical plan defining the target plane is planned on the 3D image scan displayed on a display device.

As used herein, the term "pose" refers to the position and/or the rotational angle of one object (e.g., dynamic reference array, end effector, surgical tool, anatomical structure, etc.) relative to another object and/or to a defined coordinate system. A pose may therefore be defined based on only the multidimensional position of one object relative to another object and/or to a defined coordinate system, only on the multidimensional rotational angles of the object relative to another object and/or to a defined coordinate system, or on a combination of the multidimensional position and the multidimensional rotational angles. The term "pose" therefore is used to refer to position, rotational angle, or combination thereof.

The surgical system 2 of FIG. 1 can assist surgeons during medical procedures by, for example, holding tools, aligning tools, using tools, guiding tools, and/or positioning tools for use. In some embodiments, surgical system 2 includes a surgical robot 4 and a camera tracking system component 6. The ability to mechanically couple surgical robot 4 and camera tracking system component 6 can allow for surgical system 2 to maneuver and move as a single unit, and allow surgical system 2 to have a small footprint in an area, allow easier movement through narrow passages and around turns, and allow storage within a smaller area.

A surgical procedure may begin with the surgical system 2 moving from medical storage to a medical procedure room. The surgical system 2 may be maneuvered through doorways, halls, and elevators to reach a medical procedure room. Within the room, the surgical system 2 may be physically separated into two separate and distinct systems, the surgical robot 4 and the camera tracking system component 6. Surgical robot 4 may be positioned adjacent the patient at any suitable location to properly assist medical personnel. Camera tracking system component 6 may be positioned at the base of the patient, at the patient shoulders, or any other location suitable to track the present pose and movement of the pose of tracks portions of the surgical robot 4 and the patient. Surgical robot 4 and camera tracking system component 6 may be powered by an onboard power source and/or plugged into an external wall outlet.

Surgical robot 4 may be used to assist a surgeon by holding and/or using tools during a medical procedure. To properly utilize and hold tools, surgical robot 4 may rely on a plurality of motors, computers, and/or actuators to function properly. Illustrated in FIG. 1, robot body 8 may act as the structure in which the plurality of motors, computers, and/or actuators may be secured within surgical robot 4. Robot body 8 may also provide support for robot telescoping support arm 16. The size of robot body 8 may provide a solid platform supporting attached components, and may house, conceal, and protect the plurality of motors, computers, and/or actuators that may operate attached components.

Robot base 10 may act as a lower support for surgical robot 4. In some embodiments, robot base 10 may support robot body 8 and may attach robot body 8 to a plurality of powered wheels 12. This attachment to wheels may allow robot body 8 to move in space efficiently. Robot base 10 may run the length and width of robot body 8. Robot base 10 may be about two inches to about 10 inches tall. Robot base 10 may cover, protect, and support powered wheels 12.

In some embodiments, as illustrated in FIG. 1, at least one powered wheel 12 may be attached to robot base 10. Powered wheels 12 may attach to robot base 10 at any location. Each individual powered wheel 12 may rotate about a vertical axis in any direction. A motor may be disposed above, within, or adjacent to powered wheel 12. This motor may allow for surgical system 2 to maneuver into any location and stabilize and/or level surgical system 2. A rod, located within or adjacent to powered wheel 12, may be pressed into a surface by the motor. The rod, not pictured, may be made of any suitable metal to lift surgical system 2. The rod may lift powered wheel 10, which may lift surgical system 2, to any height required to level or otherwise fix the orientation of the surgical system 2 in relation to a patient. The weight of surgical system 2, supported through small contact areas by the rod on each wheel, prevents surgical system 2 from moving during a medical procedure. This rigid positioning may prevent objects and/or people from moving surgical system 2 by accident.

Moving surgical system 2 may be facilitated using robot railing 14. Robot railing 14 provides a person with the ability to move surgical system 2 without grasping robot body 8. As illustrated in FIG. 1, robot railing 14 may run the length of robot body 8, shorter than robot body 8, and/or may run longer the length of robot body 8. Robot railing 14 may further provide protection to robot body 8, preventing objects and or personnel from touching, hitting, or bumping into robot body 8.

Robot body 8 may provide support for a Selective Compliance Articulated Robot Arm, hereafter referred to as a "SCARA." A SCARA 24 may be beneficial to use within the surgical system 2 due to the repeatability and compactness of the robotic arm. The compactness of a SCARA may provide additional space within a medical procedure, which may allow medical professionals to perform medical procedures free of excess clutter and confining areas. SCARA 24 may comprise robot telescoping support 16, robot support arm 18, and/or robot arm 20. Robot telescoping support 16 may be disposed along robot body 8. As illustrated in FIG. 1, robot telescoping support 16 may provide support for the SCARA 24 and display 34. In some embodiments, robot telescoping support 16 may extend and contract in a vertical direction. The body of robot telescoping support 16 may be any width and/or height configured to support the stress and weight placed upon it.

In some embodiments, medical personnel may move SCARA 24 through a command submitted by the medical personnel. The command may originate from input received on display 34, a tablet, and/or an XR headset (e.g., headset 920 in FIG. 9) as will be explained in further detail below. The XR headset may eliminate the need for medical personnel to refer to any other display such as the display 34 or a tablet, which enables the SCARA 24 to be configured without the display 34 and/or the tablet. The command may be generated by the depression of a switch and/or the depression of a plurality of switches, and/or may be generated based on a hand gesture command and/or voice command that is sensed by the XR headset as will be explained in further detail below.

Figure 5:
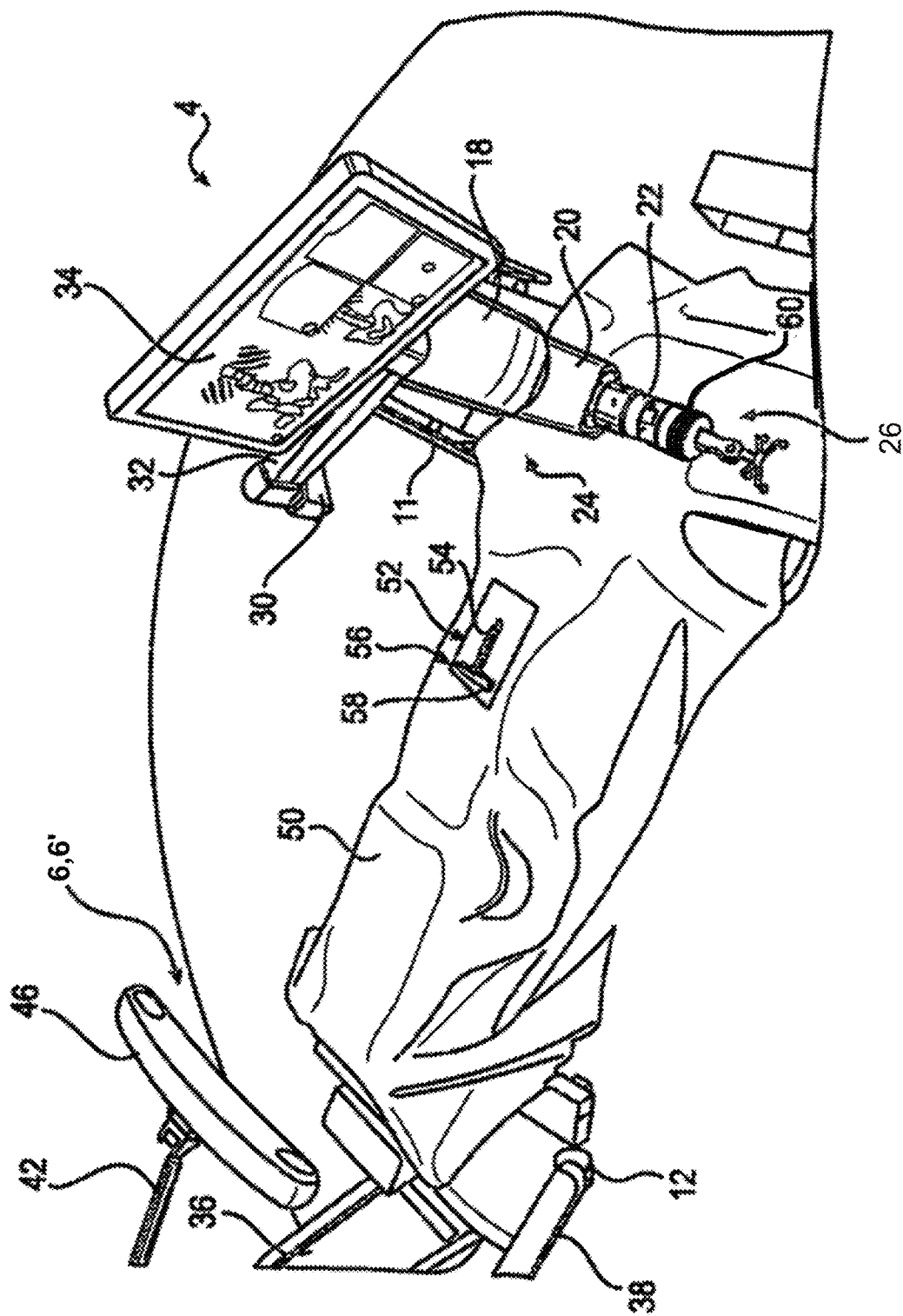
FIG. 5 illustrates a medical operation in which a surgical robot and a camera system are disposed around a patient.

As shown in FIG. 5, an activation assembly 60 may include a switch and/or a plurality of switches. The activation assembly 60 may be operable to transmit a move command to the SCARA 24 allowing an operator to manually manipulate the SCARA 24. When the switch, or plurality of switches, is depressed the medical personnel may have the ability to move SCARA 24 through applied hand movements. Alternatively or additionally, an operator may control movement of the SCARA 24 through hand gesture commands and/or voice commands that are sensed by the XR headset as will be explained in further detail below. Additionally, when the SCARA 24 is not receiving a command to move, the SCARA 24 may lock in place to prevent accidental movement by personnel and/or other objects. By locking in place, the SCARA 24 provides a solid platform through which the end effector 26 can guide a surgical tool during a medical procedure.

Robot support arm 18 can be connected to robot telescoping support 16 by various mechanisms. In some embodiments, best seen in FIGS. 1 and 2, robot support arm 18 rotates in any direction in regard to robot telescoping support 16. Robot support arm 18 may rotate three hundred and sixty degrees around robot telescoping support 16. Robot arm 20 may connect to robot support arm 18 at any suitable location and by various mechanisms that enable rotation in any direction relative to robot support arm 18. In one embodiment, the robot arm 20 can rotate three hundred and sixty degrees relative to the robot support arm 18. This free rotation allows an operator to position robot arm 20 according to a surgical plan.

Figure 4:
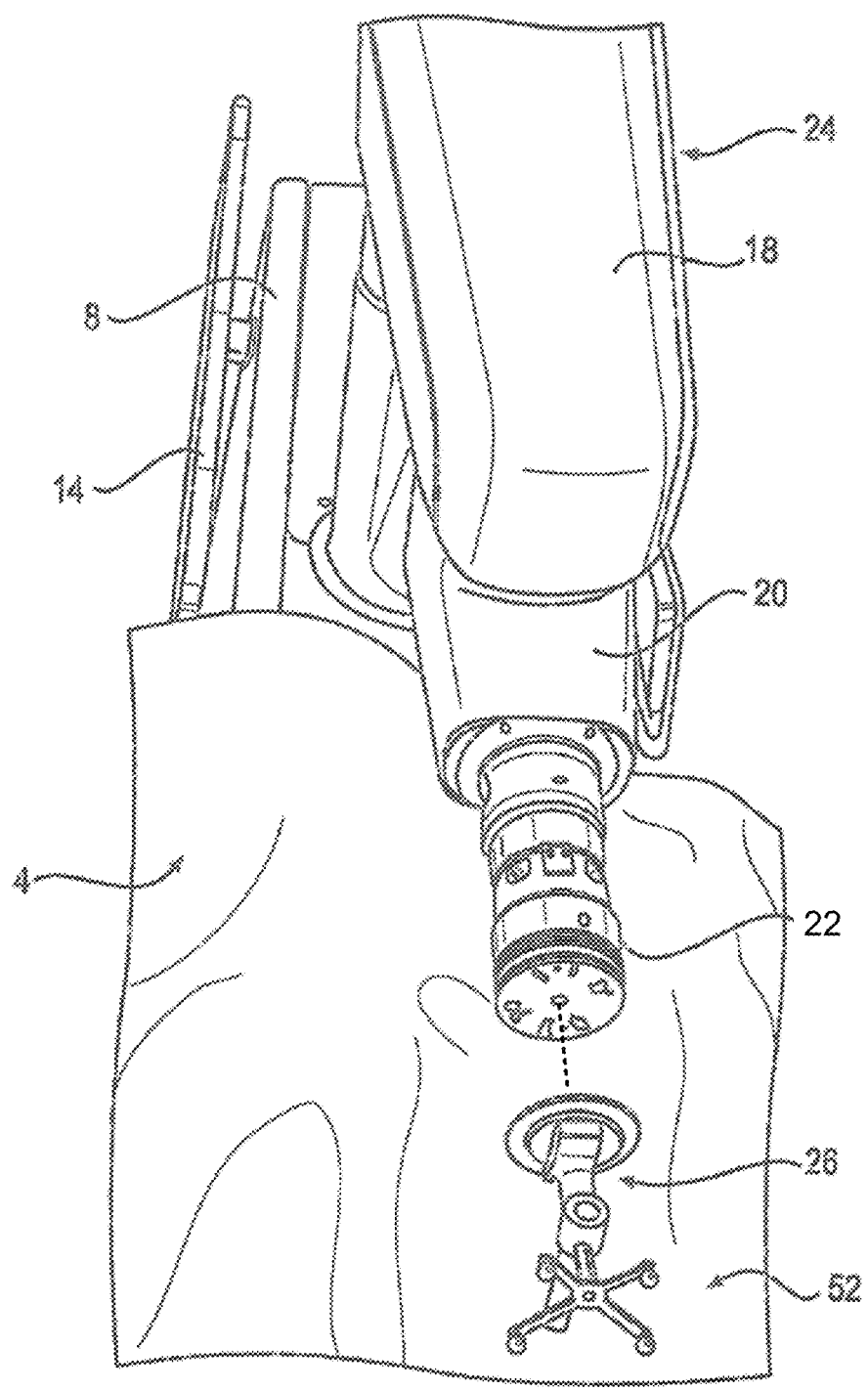
FIG. 4 illustrates an embodiment of an end effector that is connectable to a robot arm and configured according to some embodiments of the present disclosure.

The end effector 26 shown in FIGS. 4 and 5 may attach to robot arm 20 in any suitable location. The end effector 26 can be configured to attach to an end effector coupler 22 of the robot arm 20 positioned by the surgical robot 4. The example end effector 26 includes a tubular guide that guides movement of an inserted surgical tool relative to an anatomical structure on which a surgical procedure is to be performed.

In some embodiments, a dynamic reference array 52 is attached to the end effector 26. Dynamic reference arrays, also referred to as "DRAB" and "reference arrays" herein, can be rigid bodies, markers, or other indicia which may be attached or formed on one or more XR headsets being worn by personnel in the operating room, the end effector, the surgical robot, a surgical tool in a navigated surgical procedure, and an anatomical structure (e.g., bone) of a patient. The computer platform 910 in combination with the camera tracking system component 6 or other 3D localization system are configured to track in real-time the pose (e.g., positions and rotational orientations) of the DRA. The DRA can include fiducials, such as the illustrated arrangement of balls. This tracking of 3D coordinates of the DRA can allow the surgical system 2 to determine the pose of the DRA in any multidimensional space in relation to the target anatomical structure of the patient 50 in FIG. 5.

Figure 2:
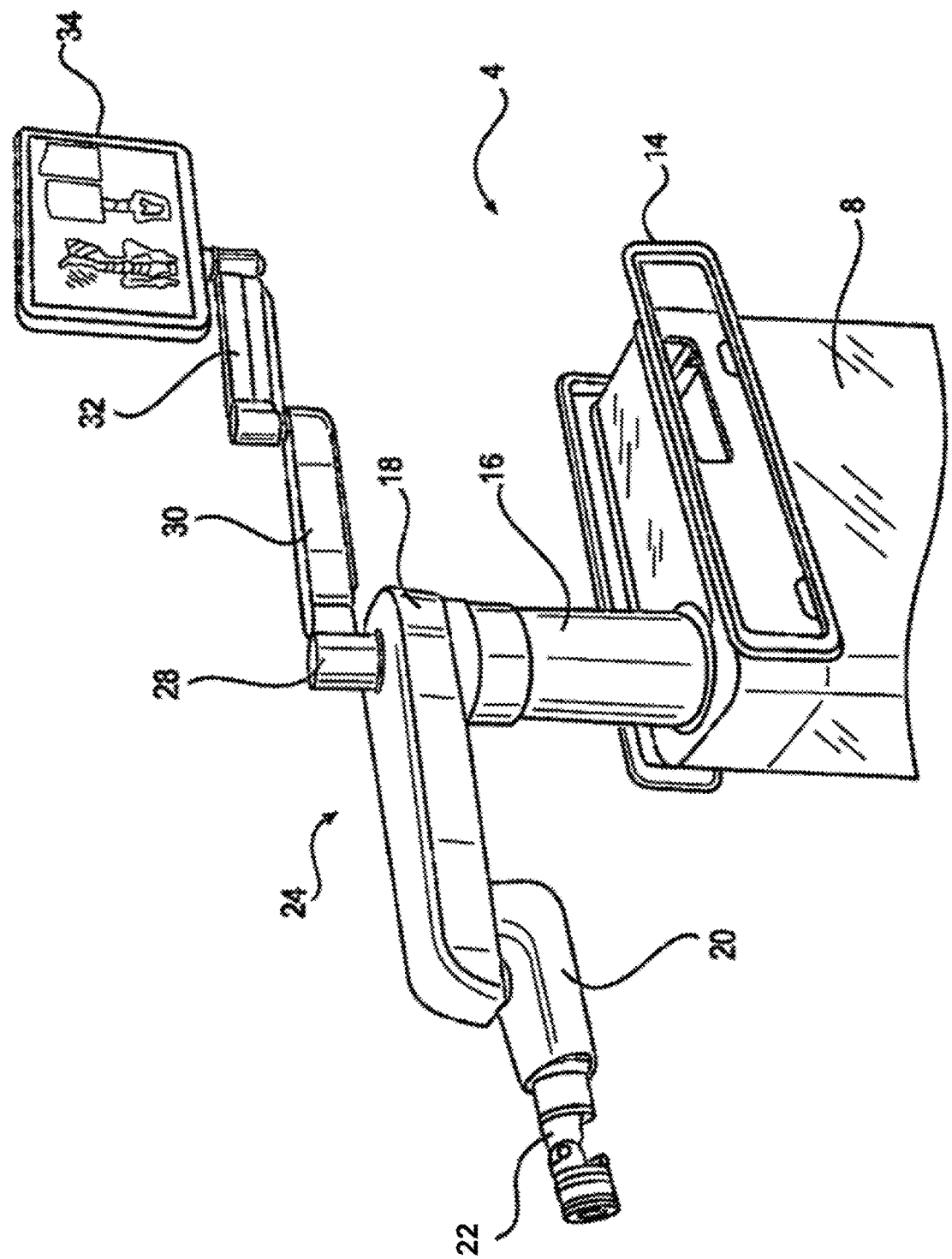
FIG. 2 illustrates a surgical robot component of the surgical system of FIG. 1 according to some embodiments of the present disclosure.

As illustrated in FIG. 1, a light indicator 28 may be positioned on top of the SCARA 24. Light indicator 28 may illuminate as any type of light to indicate "conditions" in which surgical system 2 is currently operating. In some embodiments, the light may be produced by LED bulbs, which may form a ring around light indicator 28. Light indicator 28 may comprise a fully permeable material that can let light shine through the entirety of light indicator 28. Light indicator 28 may be attached to lower display support 30. Lower display support 30, as illustrated in FIG. 2 may allow an operator to maneuver display 34 to any suitable location. Lower display support 30 may attach to light indicator 28 by any suitable mechanism. In some embodiments, lower display support 30 may rotate about light indicator 28 or be rigidly attached thereto. Upper display support 32 may attach to lower display support 30 by any suitable mechanism.

In some embodiments, a tablet may be used in conjunction with display 34 and/or without display 34. The tablet may be disposed on upper display support 32, in place of display 34, and may be removable from upper display support 32 during a medical operation. In addition the tablet may communicate with display 34. The tablet may be able to connect to surgical robot 4 by any suitable wireless and/or wired connection. In some embodiments, the tablet may be able to program and/or control surgical system 2 during a medical operation. When controlling surgical system 2 with the tablet, all input and output commands may be duplicated on display 34. The use of a tablet may allow an operator to manipulate surgical robot 4 without having to move around patient 50 and/or to surgical robot 4.

As will be explained below, in some embodiments a surgeon and/or other personnel can wear XR headsets that may be used in conjunction with display 34 and/or a tablet or the XR head(s) may eliminate the need for use of the display 34 and/or tablet.

Figure 3A:
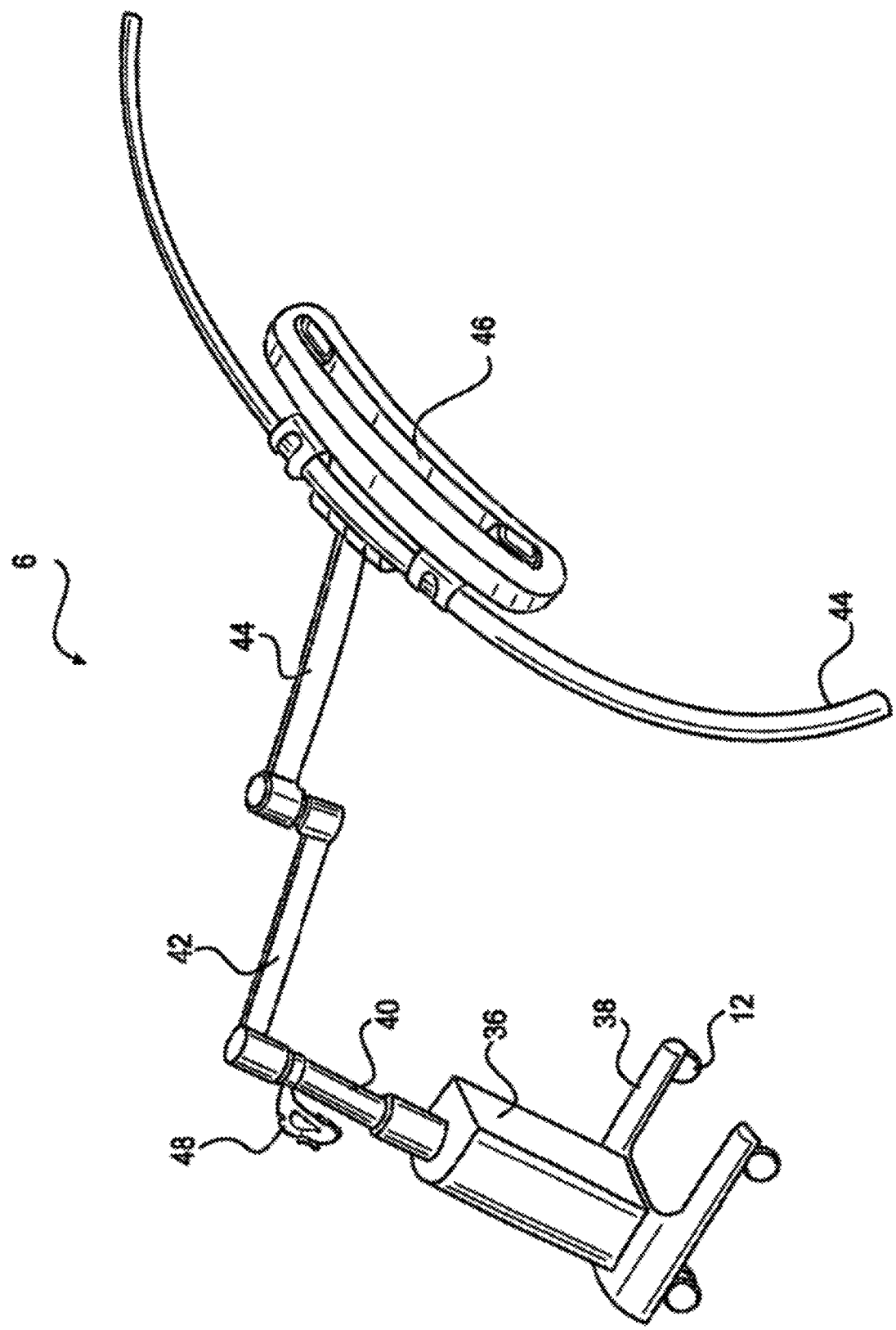
FIG. 3A illustrates a camera tracking system component of the surgical system of FIG. 1 according to some embodiments of the present disclosure.

As illustrated in FIGS. 3A and 5, camera tracking system component 6 works in conjunction with surgical robot 4 through wired or wireless communication networks. Referring to FIGS. 1, 3 and 5, camera tracking system component 6 can include some similar components to the surgical robot 4. For example, camera body 36 may provide the functionality found in robot body 8. Robot body 8 may provide an auxiliary tracking bar upon which cameras 46 are mounted. The structure within robot body 8 may also provide support for the electronics, communication devices, and power supplies used to operate camera tracking system component 6. Camera body 36 may be made of the same material as robot body 8. Camera tracking system component 6 may communicate directly to an XR headset, tablet and/or display 34 by a wireless and/or wired network to enable the XR headset, tablet and/or display 34 to control the functions of camera tracking system component 6.

Camera body 36 is supported by camera base 38. Camera base 38 may function as robot base 10. In the embodiment of FIG. 1, camera base 38 may be wider than robot base 10. The width of camera base 38 may allow for camera tracking system component 6 to connect with surgical robot 4. As illustrated in FIG. 1, the width of camera base 38 may be large enough to fit outside robot base 10. When camera tracking system component 6 and surgical robot 4 are connected, the additional width of camera base 38 may allow surgical system 2 additional maneuverability and support for surgical system 2.

As with robot base 10, a plurality of powered wheels 12 may attach to camera base 38. Powered wheel 12 may allow camera tracking system component 6 to stabilize and level or set fixed orientation in regards to patient 50, similar to the operation of robot base 10 and powered wheels 12. This stabilization may prevent camera tracking system component 6 from moving during a medical procedure and may keep cameras 46 on the auxiliary tracking bar from losing track of a DRA connected to an XR headset and/or the surgical robot 4, and/or losing track of one or more DRAs 52 connected to an anatomical structure 54 and/or tool 58 within a designated area 56 as shown in FIGS. 3A and 5. This stability and maintenance of tracking enhances the ability of surgical robot 4 to operate effectively with camera tracking system component 6. Additionally, the wide camera base 38 may provide additional support to camera tracking system component 6. Specifically, a wide camera base 38 may prevent camera tracking system component 6 from tipping over when cameras 46 is disposed over a patient, as illustrated in FIGS. 3A and 5.

Camera telescoping support 40 may support cameras 46 on the auxiliary tracking bar. In some embodiments, telescoping support 40 moves cameras 46 higher or lower in the vertical direction. Camera handle 48 may be attached to camera telescoping support 40 at any suitable location and configured to allow an operator to move camera tracking system component 6 into a planned position before a medical operation. In some embodiments, camera handle 48 is used to lower and raise camera telescoping support 40. Camera handle 48 may perform the raising and lowering of camera telescoping support 40 through the depression of a button, switch, lever, and/or any combination thereof.

Lower camera support arm 42 may attach to camera telescoping support 40 at any suitable location, in embodiments, as illustrated in FIG. 1, lower camera support arm 42 may rotate three hundred and sixty degrees around telescoping support 40. This free rotation may allow an operator to position cameras 46 in any suitable location. Lower camera support arm 42 may connect to telescoping support 40 by any suitable mechanism. Lower camera support arm 42 may be used to provide support for cameras 46. Cameras 46 may be attached to lower camera support arm 42 by any suitable mechanism. Cameras 46 may pivot in any direction at the attachment area between cameras 46 and lower camera support arm 42. In embodiments a curved rail 44 may be disposed on lower camera support arm 42.

Curved rail 44 may be disposed at any suitable location on lower camera support arm 42. As illustrated in FIG. 3A, curved rail 44 may attach to lower camera support arm 42 by any suitable mechanism. Curved rail 44 may be of any suitable shape, a suitable shape may be a crescent, circular, oval, elliptical, and/or any combination thereof. Cameras 46 may be moveably disposed along curved rail 44. Cameras 46 may attach to curved rail 44 by, for example, rollers, brackets, braces, motors, and/or any combination thereof. Motors and rollers, not illustrated, may be used to move cameras 46 along curved rail 44. As illustrated in FIG. 3A, during a medical procedure, if an object prevents cameras 46 from viewing one or more DRAs being tracked, the motors may responsively move cameras 46 along curved rail 44. This motorized movement may allow cameras 46 to move to a new position that is no longer obstructed by the object without moving camera tracking system component 6. While cameras 46 is obstructed from viewing one or more tracked DRAs, camera tracking system component 6 may send a stop signal to a surgical robot 4, XR headset, display 34, and/or a tablet. The stop signal may prevent SCARA 24 from moving until cameras 46 has reacquired tracked DRAs 52 and/or can warn an operator wearing the XR headset and/or viewing the display 34 and/or the tablet. This SCARA 24 can be configured to respond to receipt of a stop signal by stopping further movement of the base and/or end effector coupler 22 until the camera tracking system can resume tracking of DRAs.

Figure 3C:
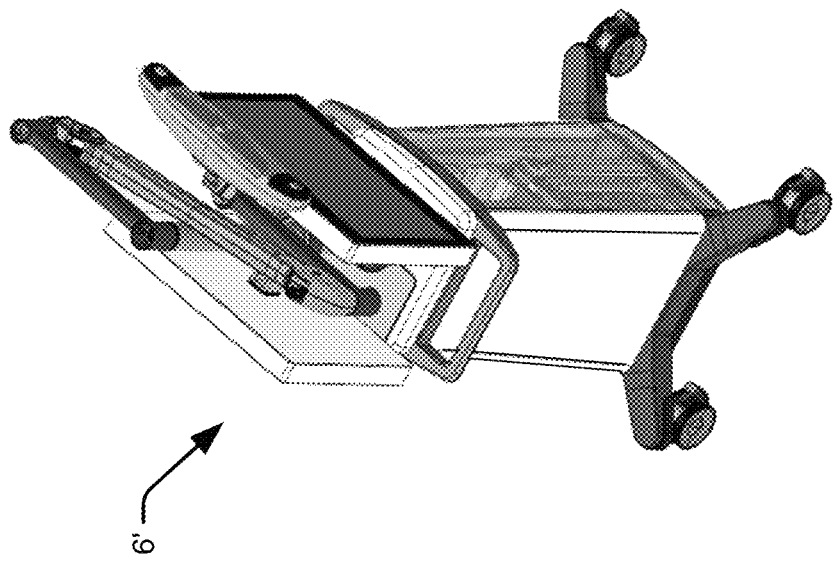
FIGS. 3B and 3C illustrate a front view and isometric view of another camera tracking system component which may be used with the surgical system of FIG. 1 according to some embodiments of the present disclosure.
Figure 3B:
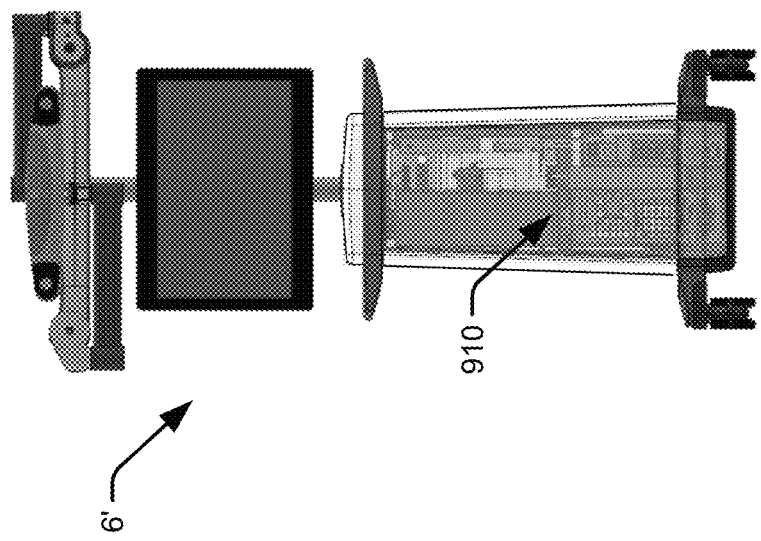

FIGS. 3B and 3C illustrate a front view and isometric view of another camera tracking system component 6' which may be used with the surgical system of FIG. 1 or may be used independent of a surgical robot. For example, the camera tracking system component 6' may be used for providing navigated surgery without use of robotic guidance. One of the differences between the camera tracking system component 6' of FIGS. 3B and 3C and the camera tracking system component 6 of FIG. 3A, is that the camera tracking system component 6' of FIGS. 3B and 3C includes a housing that transports the computer platform 910. The computer platform 910 can be configured to perform camera tracking operations to track DRAs, perform navigated surgery operations that provide surgical navigation information to a display device, e.g., XR headset and/or other display device, and perform other computational operations disclosed herein. The computer platform 910 can therefore include a navigation computer, such as one or more of the navigation computers of FIG. 14.

Figure 6:
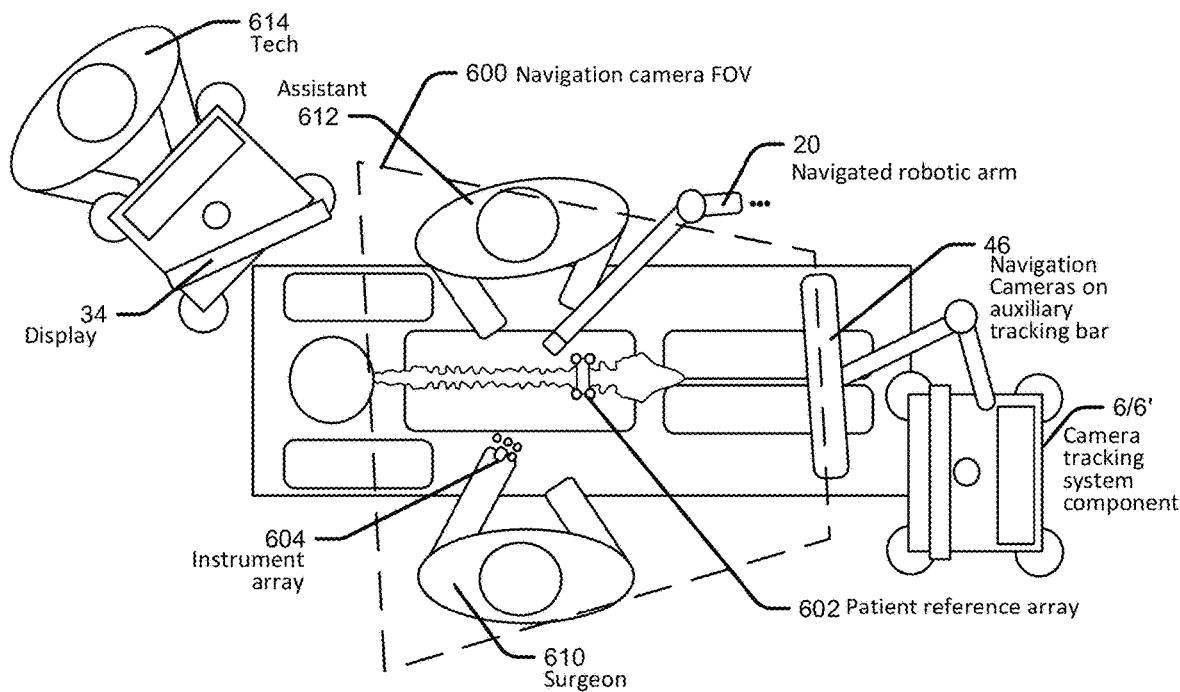
FIG. 6 illustrates a block diagram view of the components of the surgical system of FIG. 5 being used for a medical operation.

FIG. 6 illustrates a block diagram view of the components of the surgical system of FIG. 5 used for the medical operation. Referring to FIG. 6, the tracking cameras 46 on the auxiliary tracking bar has a navigation field-of-view 600 in which the pose (e.g., position and orientation) of the reference array 602 attached to the patient, the reference array 604 attached to the surgical instrument, and the robot arm 20 are tracked. The tracking cameras 46 may be part of the camera tracking system component 6' of FIGS. 3B and 3C, which includes the computer platform 910 configured to perform the operations described below. The reference arrays enable tracking by reflecting light in known patterns, which are decoded to determine their respective poses by the tracking subsystem of the surgical robot 4. If the line-of-sight between the patient reference array 602 and the tracking cameras 46 in the auxiliary tracking bar is blocked (for example, by a medical personnel, instrument, etc.), further navigation of the surgical instrument may not be able to be performed and a responsive notification may temporarily halt further movement of the robot arm 20 and surgical robot 4, display a warning on the display 34, and/or provide an audible warning to medical personnel. The display 34 is accessible to the surgeon 610 and assistant 612 but viewing requires a head to be turned away from the patient and for eye focus to be changed to a different distance and location. The navigation software may be controlled by a tech personnel 614 based on vocal instructions from the surgeon.

Figure 7:
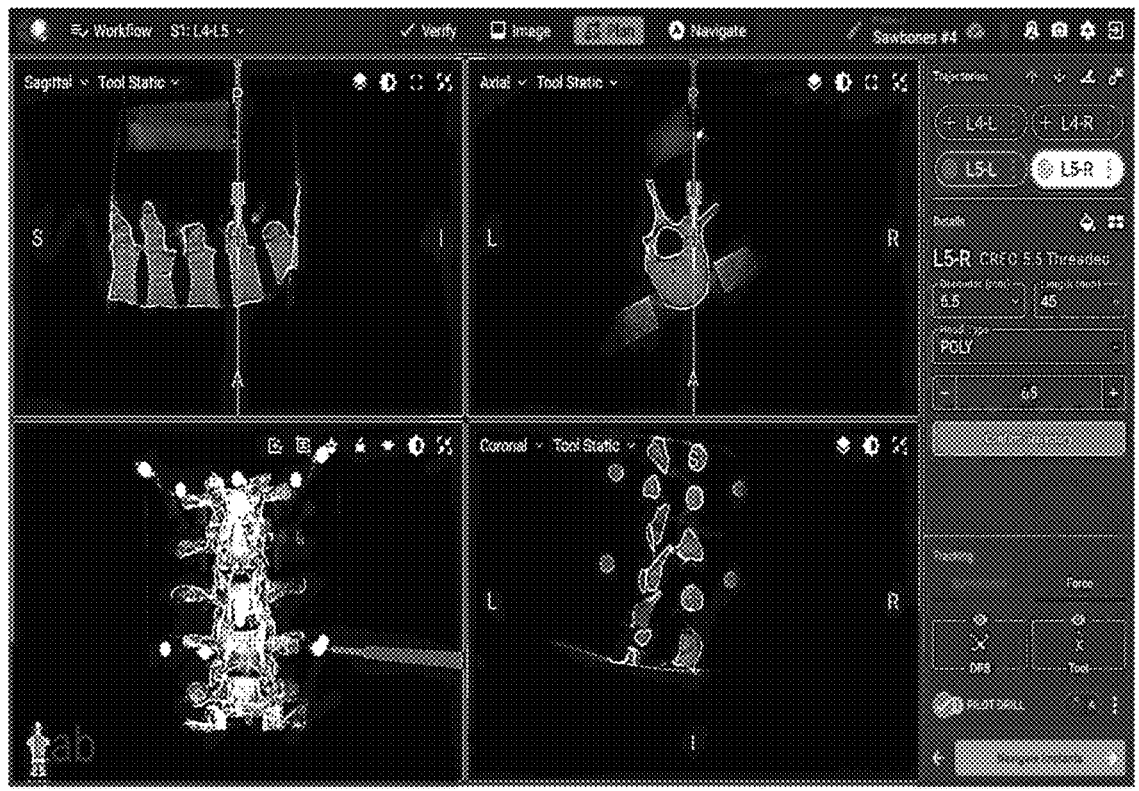
FIG. 7 illustrates various display screens that may be displayed on the display of FIGS. 5 and 6 when using a navigation function of the surgical system.

FIG. 7 illustrates various display screens that may be displayed on the display 34 of FIGS. 5 and 6 by the surgical robot 4 when using a navigation function of the surgical system 2. The display screens can include, without limitation, patient radiographs with overlaid graphical representations of models of instruments that are positioned in the display screens relative to the anatomical structure based on a developed surgical plan and/or based on poses of tracked reference arrays, various user selectable menus for controlling different stages of the surgical procedure and dimension parameters of a virtually projected implant (e.g. length, width, and/or diameter).

For navigated surgery, various processing components (e.g., computer platform 910) and associated software described below are provided that enable pre-operatively planning of a surgical procedure, e.g., implant placement, and electronic transfer of the plan to computer platform 910 to provide navigation information to one or more users during the planned surgical procedure.

For robotic navigation, various processing components (e.g., computer platform 910) and associated software described below are provided that enable pre-operatively planning of a surgical procedure, e.g., implant placement, and electronic transfer of the plan to the surgical robot 4. The surgical robot 4 uses the plan to guide the robot arm 20 and connected end effector 26 to provide a target pose for a surgical tool relative to a patient anatomical structure for a step of the planned surgical procedure.

Various embodiments below are directed to using one or more XR headsets that can be worn by the surgeon 610, the assistant 612, and/or other medical personnel to provide an improved user interface for receiving information from and/or providing control commands to the surgical robot, the camera tracking system component 6/6', and/or other medical equipment in the operating room.

Figure 8:
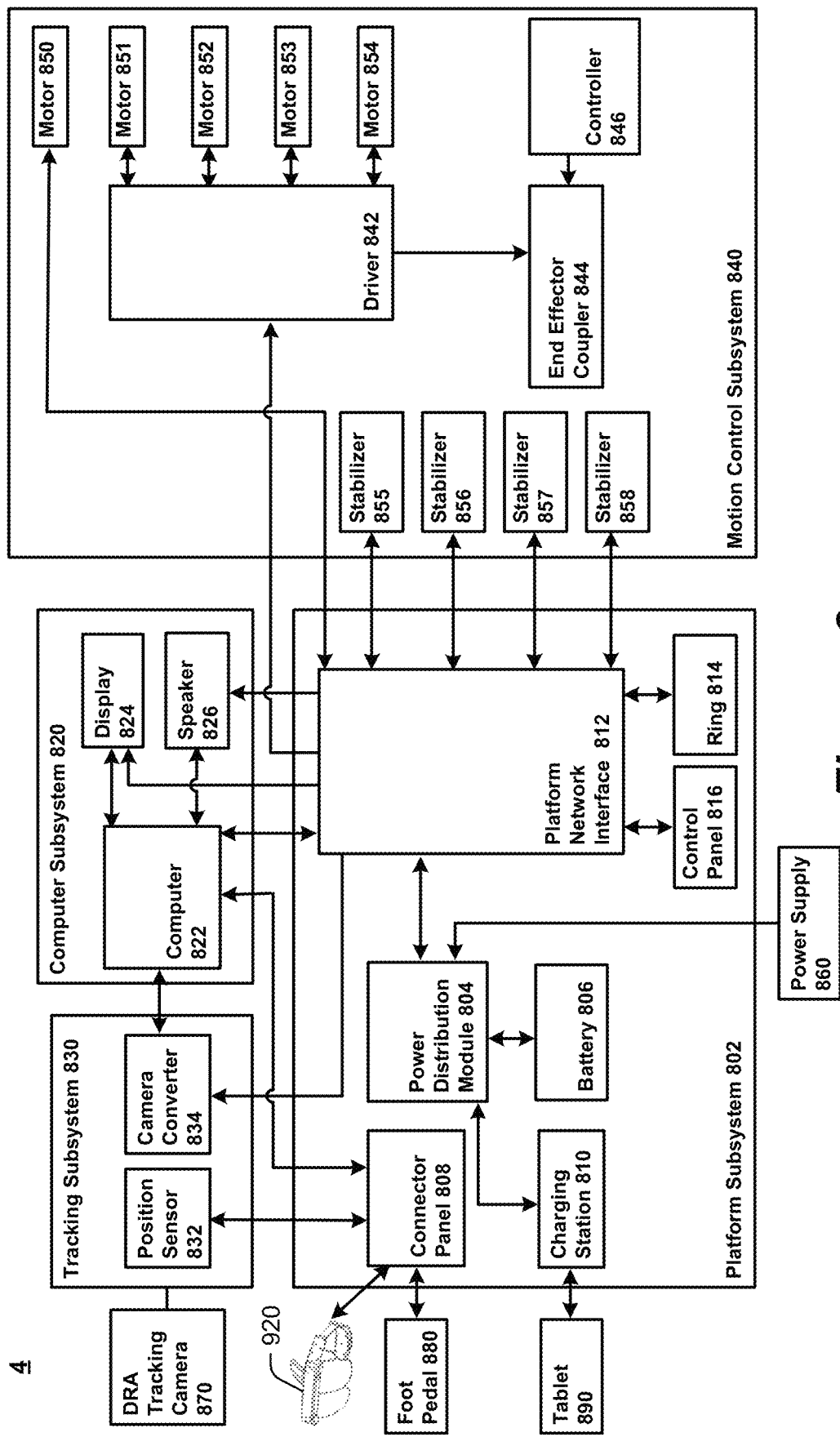
FIG. 8 illustrates a block diagram of some electrical components of a surgical robot according to some embodiments of the present disclosure.

FIG. 8 illustrates a block diagram of some electrical components of the surgical robot 4 according to some embodiments of the present disclosure. Referring to FIG. 8, a load cell (not shown) may be configured to track force applied to end effector coupler 22. In some embodiments the load cell may communicate with a plurality of motors 850, 851, 852, 853, and/or 854. As load cell senses force, information as to the amount of force applied may be distributed from a switch array and/or a plurality of switch arrays to a controller 846. Controller 846 may take the force information from load cell and process it with a switch algorithm. The switch algorithm is used by the controller 846 to control a motor driver 842. The motor driver 842 controls operation of one or more of the motors 850, 851, 852, 853, and 854. Motor driver 842 may direct a specific motor to produce, for example, an equal amount of force measured by load cell through the motor. In some embodiments, the force produced may come from a plurality of motors, e.g., 850-854, as directed by controller 846. Additionally, motor driver 842 may receive input from controller 846. Controller 846 may receive information from load cell as to the direction of force sensed by load cell. Controller 846 may process this information using a motion controller algorithm. The algorithm may be used to provide information to specific motor drivers 842. To replicate the direction of force, controller 846 may activate and/or deactivate certain motor drivers 842. Controller 846 may control one or more motors, e.g. one or more of 850-854, to induce motion of end effector 26 in the direction of force sensed by load cell. This force-controlled motion may allow an operator to move SCARA 24 and end effector 26 effortlessly and/or with very little resistance. Movement of end effector 26 can be performed to position end effector 26 in any suitable pose (i.e., location and angular orientation relative to defined three-dimensional (3D) orthogonal reference axes) for use by medical personnel.

Activation assembly 60, best illustrated in FIG. 5, may form of a bracelet that wraps around end effector coupler 22. The activation assembly 60 may be located on any part of SCARA 24, any part of end effector coupler 22, may be worn by medical personnel (and communicate wirelessly), and/or any combination thereof. Activation assembly 60 may comprise of a primary button and a secondary button.

Depressing primary button may allow an operator to move SCARA 24 and end effector coupler 22. According to one embodiment, once set in place, SCARA 24 and end effector coupler 22 may not move until an operator programs surgical robot 4 to move SCARA 24 and end effector coupler 22, or is moved using primary button. In some examples, it may require the depression of at least two non-adjacent primary activation switches before SCARA 24 and end effector coupler 22 will respond to operator commands. Depression of at least two primary activation switches may prevent the accidental movement of SCARA 24 and end effector coupler 22 during a medical procedure.

Activated by primary button, load cell may measure the force magnitude and/or direction exerted upon end effector coupler 22 by an operator, i.e. medical personnel. This information may be transferred to one or more motors, e.g. one or more of 850-854, within SCARA 24 that may be used to move SCARA 24 and end effector coupler 22. Information as to the magnitude and direction of force measured by load cell may cause the one or more motors, e.g. one or more of 850-854, to move SCARA 24 and end effector coupler 22 in the same direction as sensed by the load cell. This force-controlled movement may allow the operator to move SCARA 24 and end effector coupler 22 easily and without large amounts of exertion due to the motors moving SCARA 24 and end effector coupler 22 at the same time the operator is moving SCARA 24 and end effector coupler 22.

In some examples, a secondary button may be used by an operator as a "selection" device. During a medical operation, surgical robot 4 may notify medical personnel to certain conditions by the XR headset(s) 920, display 34 and/or light indicator 28. The XR headset(s) 920 are each configured to display images on a see-through display screen to form an extended reality image that is overlaid on real-world objects viewable through the see-through display screen. Medical personnel may be prompted by surgical robot 4 to select a function, mode, and/or assess the condition of surgical system 2. Depressing secondary button a single time may activate certain functions, modes, and/or acknowledge information communicated to medical personnel through the XR headset(s) 920, display 34 and/or light indicator 28. Additionally, depressing the secondary button multiple times in rapid succession may activate additional functions, modes, and/or select information communicated to medical personnel through the XR headset(s) 920, display 34 and/or light indicator 28.

With further reference to FIG. 8, electrical components of the surgical robot 4 include platform subsystem 802, computer subsystem 820, motion control subsystem 840, and tracking subsystem 830. Platform subsystem 802 includes battery 806, power distribution module 804, connector panel 808, and charging station 810. Computer subsystem 820 includes computer 822, display 824, and speaker 826. Motion control subsystem 840 includes driver circuit 842, motors 850, 851, 852, 853, 854, stabilizers 855, 856, 857, 858, end effector connector 844, and controller 846. Tracking subsystem 830 includes position sensor 832 and camera converter 834. Surgical robot 4 may also include a removable foot pedal 880 and removable tablet computer 890.

Input power is supplied to surgical robot 4 via a power source which may be provided to power distribution module 804. Power distribution module 804 receives input power and is configured to generate different power supply voltages that are provided to other modules, components, and subsystems of surgical robot 4. Power distribution module 804 may be configured to provide different voltage supplies to connector panel 808, which may be provided to other components such as computer 822, display 824, speaker 826, driver 842 to, for example, power motors 850-854 and end effector coupler 844, and provided to camera converter 834 and other components for surgical robot 4. Power distribution module 804 may also be connected to battery 806, which serves as temporary power source in the event that power distribution module 804 does not receive power from an input power. At other times, power distribution module 804 may serve to charge battery 806.

Connector panel 808 may serve to connect different devices and components to surgical robot 4 and/or associated components and modules. Connector panel 808 may contain one or more ports that receive lines or connections from different components. For example, connector panel 808 may have a ground terminal port that may ground surgical robot 4 to other equipment, a port to connect foot pedal 880, a port to connect to tracking subsystem 830, which may include position sensor 832, camera converter 834, and DRA tracking cameras 870. Connector panel 808 may also include other ports to allow USB, Ethernet, HDMI communications to other components, such as computer 822. In accordance with some embodiments, the connector panel 808 can include a wired and/or wireless interface for operatively connecting one or more XR headsets 920 to the tracking subsystem 830 and/or the computer subsystem 820.

Control panel 816 may provide various buttons or indicators that control operation of surgical robot 4 and/or provide information from surgical robot 4 for observation by an operator. For example, control panel 816 may include buttons to power on or off surgical robot 4, lift or lower vertical column 16, and lift or lower stabilizers 855-858 that may be designed to engage casters 12 to lock surgical robot 4 from physically moving. Other buttons may stop surgical robot 4 in the event of an emergency, which may remove all motor power and apply mechanical brakes to stop all motion from occurring. Control panel 816 may also have indicators notifying the operator of certain system conditions such as a line power indicator or status of charge for battery 806. In accordance with some embodiments, one or more XR headsets 920 may communicate, e.g. via the connector panel 808, to control operation of the surgical robot 4 and/or to received and display information generated by surgical robot 4 for observation by persons wearing the XR headsets 920.

Computer 822 of computer subsystem 820 includes an operating system and software to operate assigned functions of surgical robot 4. Computer 822 may receive and process information from other components (for example, tracking subsystem 830, platform subsystem 802, and/or motion control subsystem 840) in order to display information to the operator. Further, computer subsystem 820 may provide output through the speaker 826 for the operator. The speaker may be part of the surgical robot, part of an XR headset 920, or within another component of the surgical system 2. The display 824 may correspond to the display 34 shown in FIGS. 1 and 2.

Tracking subsystem 830 may include position sensor 832 and camera converter 834. Tracking subsystem 830 may correspond to the camera tracking system component 6 of FIG. 3. The DRA tracking cameras 870 operate with the position sensor 832 to determine the pose of DRAs 52. This tracking may be conducted in a manner consistent with the present disclosure including the use of infrared or visible light technology that tracks the location of active or passive elements of DRAs 52, such as LEDs or reflective fiducials (also called markers), respectively.

Functional operations of the tracking subsystem 830 and the computer subsystem 820 can be included in the computer platform 910, which can be transported by the camera tracking system component 6' of FIGS. 3A and 3B. The tracking subsystem 830 can be configured to determine the poses, e.g., location and angular orientation of the tracked DRAs. The computer platform 910 can also include a navigation controller that is configured to use the determined poses to provide navigation information to users that guides their movement of tracked tools relative to position-registered patient images and/or tracked anatomical structures during a planned surgical procedure. The computer platform 910 can display information on the display of FIGS. 3B and 3C and/or to one or more XR headsets 920. The computer platform 910, when used with a surgical robot, can be configured to communicate with the computer subsystem 820 and other subsystems of FIG. 8 to control movement of the end effector 26. For example, as will be explained below the computer platform 910 can generate a graphical representation of a patient's anatomical structure, surgical tool, user's hand, etc. with a displayed size, shape, color, and/or pose that is controlled based on the determined pose(s) of one or more the tracked DRAs, and which the graphical representation that is displayed can be dynamically modified to track changes in the determined poses over time.

Motion control subsystem 840 may be configured to physically move vertical column 16, upper arm 18, lower arm 20, or rotate end effector coupler 22. The physical movement may be conducted through the use of one or more motors 850-854. For example, motor 850 may be configured to vertically lift or lower vertical column 16. Motor 851 may be configured to laterally move upper arm 18 around a point of engagement with vertical column 16 as shown in FIG. 2. Motor 852 may be configured to laterally move lower arm 20 around a point of engagement with upper arm 18 as shown in FIG. 2. Motors 853 and 854 may be configured to move end effector coupler 22 to provide translational movement and rotation along in about three-dimensional axes. The computer platform 910 shown in FIG. 9 can provide control input to the controller 846 that guides movement of the end effector coupler 22 to position a passive end effector, which is connected thereto, with a planned pose (i.e., location and angular orientation relative to defined 3D orthogonal reference axes) relative to an anatomical structure that is to be operated on during a planned surgical procedure. Motion control subsystem 840 may be configured to measure position of the end effector coupler 22 and/or the end effector 26 using integrated position sensors (e.g. encoders).

Figure 9:
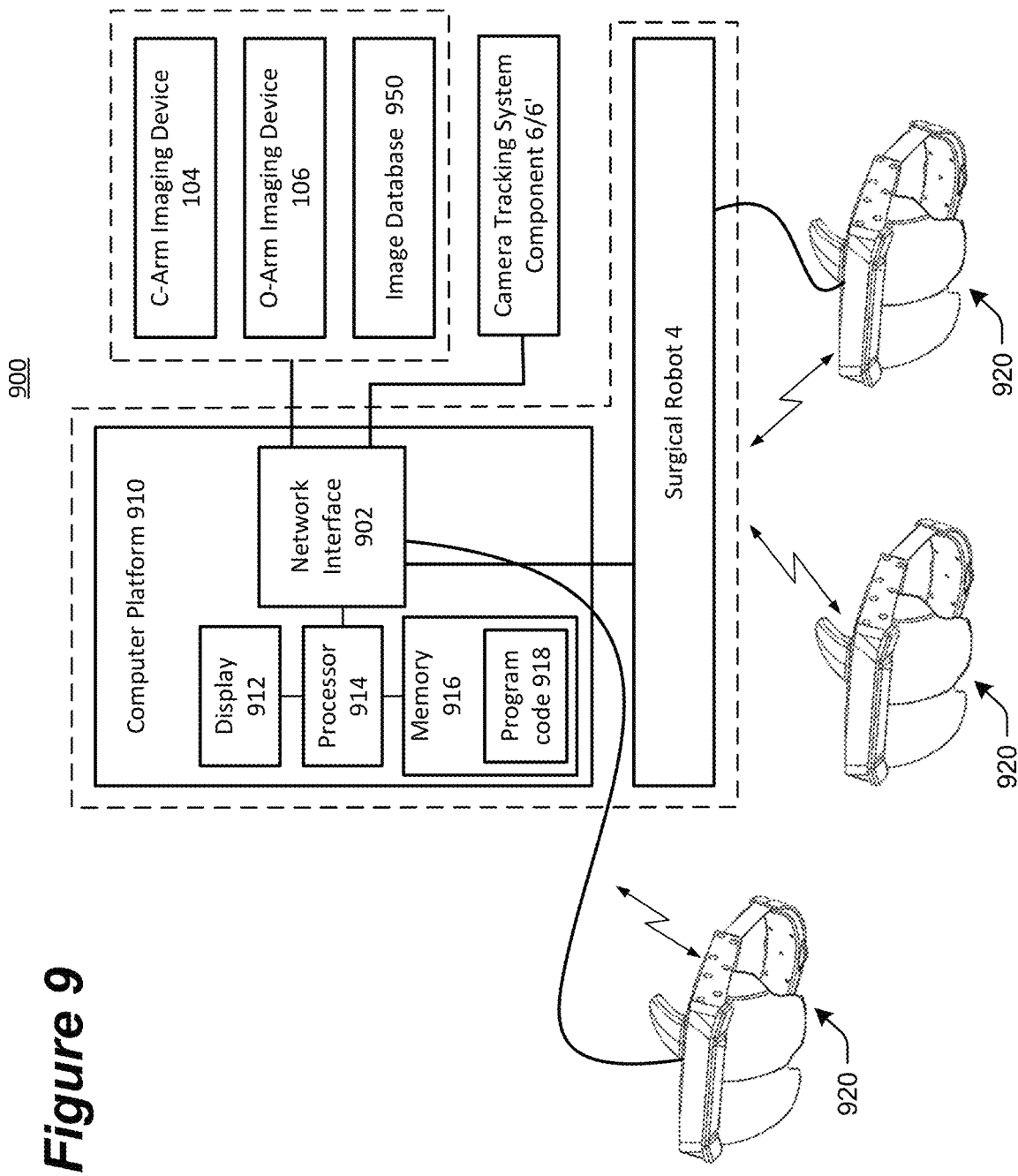
FIG. 9 illustrates a block diagram of components of a surgical system that includes imaging devices connected to a computer platform which can be operationally connected to a camera tracking system and/or surgical robot according to some embodiments of the present disclosure.

FIG. 9 illustrates a block diagram of components of a surgical system that includes imaging devices (e.g., C-Arm 104, O-Arm 106, etc.) connected to a computer platform 910 which can be operationally connected to a camera tracking system component 6 (FIG. 3A) or 6' (FIGS. 3B,3C) and/or to surgical robot 4 according to some embodiments of the present disclosure. Alternatively, at least some operations disclosed herein as being performed by the computer platform 910 may additionally or alternatively be performed by components of a surgical system.

Referring to FIG. 9, the computer platform 910 includes a display 912, at least one processor circuit 914 (also referred to as a processor for brevity), at least one memory circuit 916 (also referred to as a memory for brevity) containing computer readable program code 918, and at least one network interface 902 (also referred to as a network interface for brevity). The display 912 may be part of an XR headset 920 in accordance with some embodiments of the present disclosure. The network interface 902 can be configured to connect to a C-Arm imaging device 104 in FIG.

Figure 11:
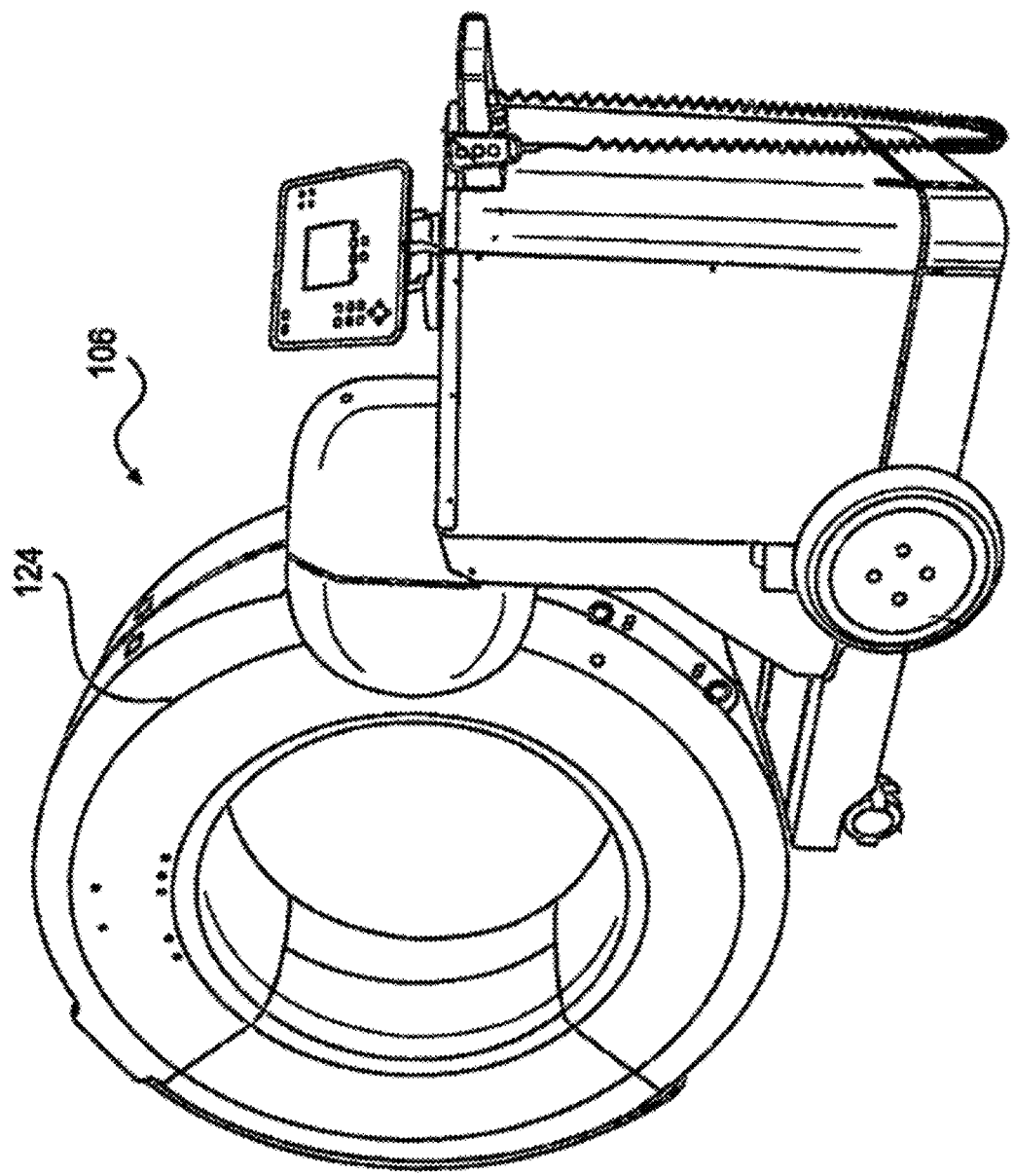
FIG. 11 illustrates an embodiment of an O-Arm imaging device that can be used in combination with the surgical robot in accordance with some embodiments of the present disclosure.

10, an O-Arm imaging device 106 in FIG. 11, another medical imaging device, an image database 950 containing patient medical images, components of the surgical robot 4, and/or other electronic equipment.

When used with a surgical robot 4, the display 912 may correspond to the display 34 of FIG. 2 and/or the tablet 890 of FIG. 8 and/or the XR headset 920 that is operatively connected to the surgical robot 4, the network interface 902 may correspond to the platform network interface 812 of FIG. 8, and the processor 914 may correspond to the computer 822 of FIG. 8. The network interface 902 of the XR headset 920 may be configured to communicate through a wired network, e.g., thin wire ethernet, and/or through wireless RF transceiver link according to one or more wireless communication protocols, e.g., WLAN, 3GPP 4G and/or 5G (New Radio) cellular communication standards, etc.

The processor 914 may include one or more data processing circuits, such as a general purpose and/or special purpose processor, e.g., microprocessor and/or digital signal processor. The processor 914 is configured to execute the computer readable program code 918 in the memory 916 to perform operations, which may include some or all of the operations described herein as being performed for surgery planning, navigated surgery, and/or robotic surgery.

The computer platform 910 can be configured to provide surgery planning functionality. The processor 914 can operate to display on the display device 912 and/or on the XR headset 920 an image of an anatomical structure, e.g., vertebra, that is received from one of the imaging devices 104 and 106 and/or from the image database 950 through the network interface 920. The processor 914 receives an operator's definition of where the anatomical structure shown in one or more images is to have a surgical procedure, e.g., screw placement, such as by the operator touch selecting locations on the display 912 for planned procedures or using a mouse-based cursor to define locations for planned procedures. When the image is displayed in the XR headset 920, the XR headset can be configured to sense in gesture-based commands formed by the wearer and/or sense voice based commands spoken by the wearer, which can be used to control selection among menu items and/or control how objects are displayed on the XR headset 920 as will be explained in further detail below.

The computer platform 910 can be configured to enable anatomy measurement, which can be particularly useful for knee surgery, like measurement of various angles determining center of hip, center of angles, natural landmarks (e.g. transepicondylar line, Whitesides line, posterior condylar line), etc. Some measurements can be automatic while some others can involve human input or assistance. The computer platform 910 may be configured to allow an operator to input a choice of the correct implant for a patient, including choice of size and alignment. The computer platform 910 may be configured to perform automatic or semi-automatic (involving human input) segmentation (image processing) for CT images or other medical images. The surgical plan for a patient may be stored in a cloud-based server, which may correspond to database 950, for retrieval by the surgical robot 4.

During orthopedic surgery, for example, a surgeon may choose which cut to make (e.g. posterior femur, proximal tibia etc.) using a computer screen (e.g. touchscreen) or extended reality (XR) interaction (e.g., hand gesture based commands and/or voice based commands) via, e.g., the XR headset 920. The computer platform 910 can generate navigation information which provides visual guidance to the surgeon for performing the surgical procedure. When used with the surgical robot 4, the computer platform 910 can provide guidance that allows the surgical robot 4 to automatically move the end effector 26 to a target pose so that the surgical tool is aligned with a target location to perform the surgical procedure on an anatomical structure.

In some embodiments, the surgical system 900 can use two DRAs to track patient anatomy position, such as one connected to patient tibia and one connected to patient femur. The system 900 may use standard navigated instruments for the registration and checks (e.g. a pointer similar to the one used in Globus ExcelsiusGPS system for spine surgery).

A particularly challenging task in navigated surgery is how to plan the position of an implant in spine, knee, and other anatomical structures where surgeons struggle to perform the task on a computer screen which is a 2D representation of the 3D anatomical structure. The system 900 could address this problem by using the XR headset 920 to display a three-dimensional (3D) computer generated representations of the anatomical structure and a candidate implant device. The computer generated representations are scaled and posed relative to each other on the display screen under guidance of the computer platform 910 and which can be manipulated by a surgeon while viewed through the XR headset 920. A surgeon may, for example, manipulate the displayed computer-generated representations of the anatomical structure, the implant, a surgical tool, etc., using hand gesture based commands and/or voice based commands that are sensed by the XR headset 920.

For example, a surgeon can view a displayed virtual handle on a virtual implant, and can manipulate (e.g., grab and move) the virtual handle to move the virtual implant to a desired pose and adjust a planned implant placement relative to a graphical representation of an anatomical structure. Afterward, during surgery, the computer platform 910 could display navigation information through the XR headset 920 that facilitates the surgeon's ability to more accurately follow the surgical plan to insert the implant and/or to perform another surgical procedure on the anatomical structure. When the surgical procedure involves bone removal, the progress of bone removal, e.g., depth of cut, can be displayed in real-time through the XR headset 920. Other features that may be displayed through the XR headset 920 can include, without limitation, gap or ligament balance along a range of joint motion, contact line on the implant along the range of joint motion, ligament tension and/or laxity through color or other graphical renderings, etc.

The computer platform 910, in some embodiments, can allow planning for use of standard surgical tools and/or implants, e.g., posterior stabilized implants and cruciate retaining implants, cemented and cementless implants, revision systems for surgeries related to, for example, total or partial knee and/or hip replacement and/or trauma.

Figure 10:
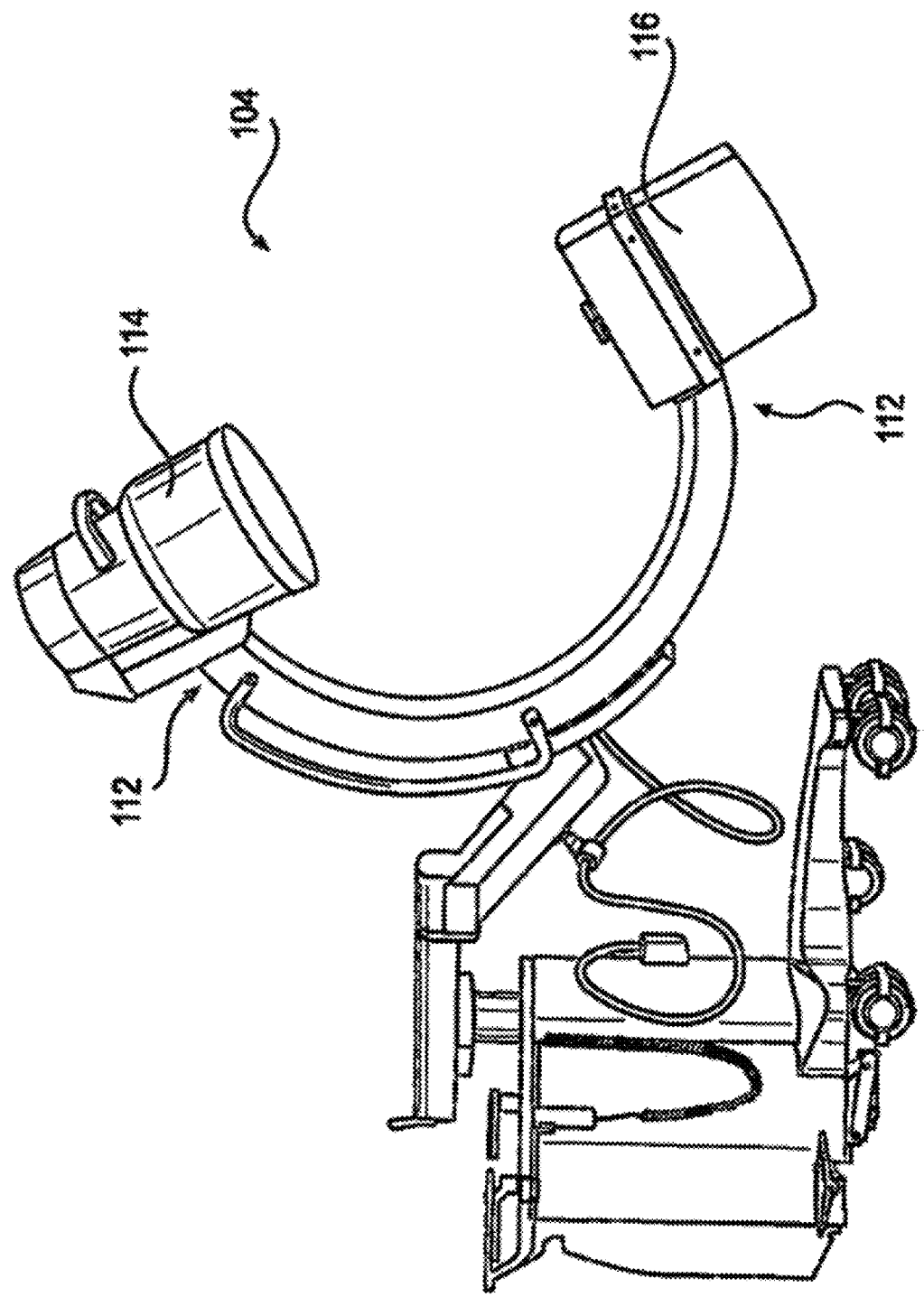
FIG. 10 illustrates an embodiment of a C-Arm imaging device that can be used in combination with the surgical robot in accordance with some embodiments of the present disclosure.

An automated imaging system can be used in conjunction with the computer platform 910 to acquire pre-operative, intra-operative, post-operative, and/or real-time image data of an anatomical structure. Example automated imaging systems are illustrated in FIGS. 10 and 11. In some embodiments, the automated imaging system is a C-arm 104 (FIG. 10) imaging device or an O-arm® 106 (FIG. 11). (O-arm® is copyrighted by Medtronic Navigation, Inc. having a place of business in Louisville, Colo., USA). It may be desirable to take x-rays of a patient from a number of different positions, without the need for frequent manual repositioning of the patient which may be required in an x-ray system. C-arm 104 x-ray diagnostic equipment may solve the problems of frequent manual repositioning and may be well known in the medical art of surgical and other interventional procedures. As illustrated in FIG. 10, a C-arm includes an elongated C-shaped member terminating in opposing distal ends 112 of the "C" shape. C-shaped member is attached to an x-ray source 114 and an image receptor 116. The space within C-arm 104 of the arm provides room for the physician to attend to the patient substantially free of interference from the x-ray support structure.

The C-arm is mounted to enable rotational movement of the arm in two degrees of freedom, (i.e. about two perpendicular axes in a spherical motion). C-arm is slidably mounted to an x-ray support structure, which allows orbiting rotational movement of the C-arm about its center of curvature, which may permit selective orientation of x-ray source 114 and image receptor 116 vertically and/or horizontally. The C-arm may also be laterally rotatable, (i.e. in a perpendicular direction relative to the orbiting direction to enable selectively adjustable positioning of x-ray source 114 and image receptor 116 relative to both the width and length of the patient). Spherically rotational aspects of the C-arm apparatus allow physicians to take x-rays of the patient at an optimal angle as determined with respect to the particular anatomical condition being imaged.

The O-arm® 106 illustrated in FIG. 11 includes a gantry housing 124 which may enclose an image capturing portion, not illustrated. The image capturing portion includes an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of the patient to be acquired from multiple directions or in multiple planes.

The O-arm® 106 with the gantry housing 124 has a central opening for positioning around an object to be imaged, a source of radiation that is rotatable around the interior of gantry housing 124, which may be adapted to project radiation from a plurality of different projection angles. A detector system is adapted to detect the radiation at each projection angle to acquire object images from multiple projection planes in a quasi-simultaneous manner. The gantry may be attached to a support structure O-arm® support structure, such as a wheeled mobile cart with wheels, in a cantilevered fashion. A positioning unit translates and/or tilts the gantry to a planned position and orientation, preferably under control of a computerized motion control system. The gantry may include a source and detector disposed opposite one another on the gantry. The source and detector may be secured to a motorized rotor, which may rotate the source and detector around the interior of the gantry in coordination with one another. The source may be pulsed at multiple positions and orientations over a partial and/or full three hundred and sixty degree rotation for multi-planar imaging of a targeted object located inside the gantry. The gantry may further comprise a rail and bearing system for guiding the rotor as it rotates, which may carry the source and detector. Both and/or either O-arm® 106 and C-arm 104 may be used as automated imaging system to scan a patient and send information to the surgical system 2.

Images captured by an imaging system can be displayed on the XR headset 920 and/or another display device of the computer platform 910, the surgical robot 4, and/or another component of the surgical system 900. The XR headset 920 may be connected to one or more of the imaging devices 104 and/or 106 and/or to the image database 950, e.g., via the computer platform 910, to display images therefrom. A user may provide control inputs through the XR headset 920, e.g., gesture and/or voice based commands, to control operation of one or more of the imaging devices 104 and/or 106 and/or the image database 950.

Figure 12:
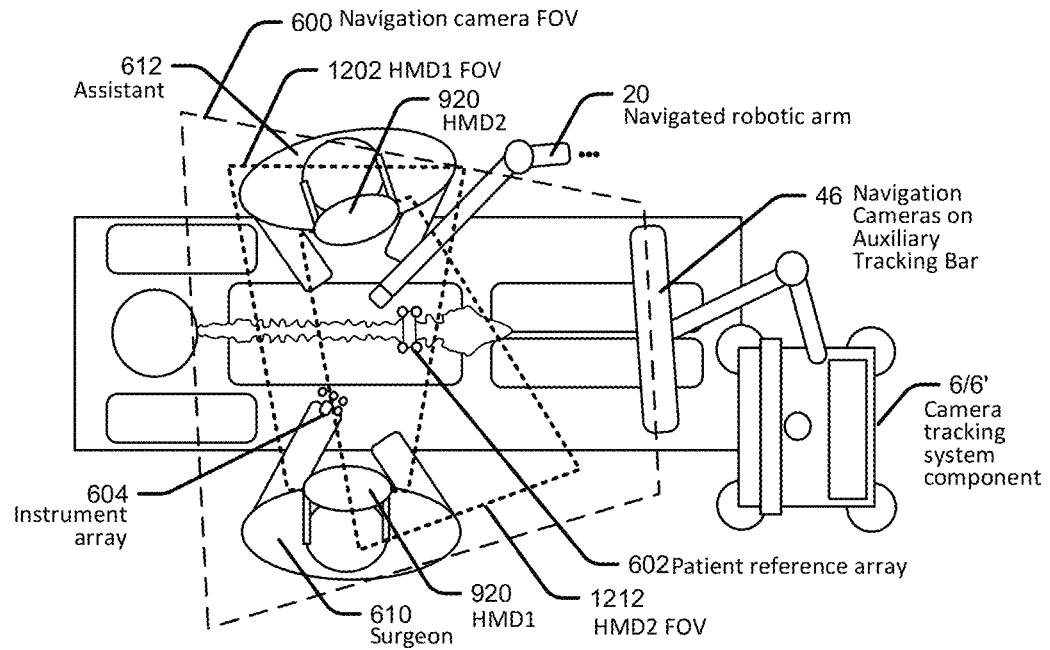
FIG. 12 illustrates a block diagram view of the components of a surgical system that includes a pair of XR headsets and an auxiliary tracking bar which operate in accordance with some embodiments of the present disclosure.
Figure 13:
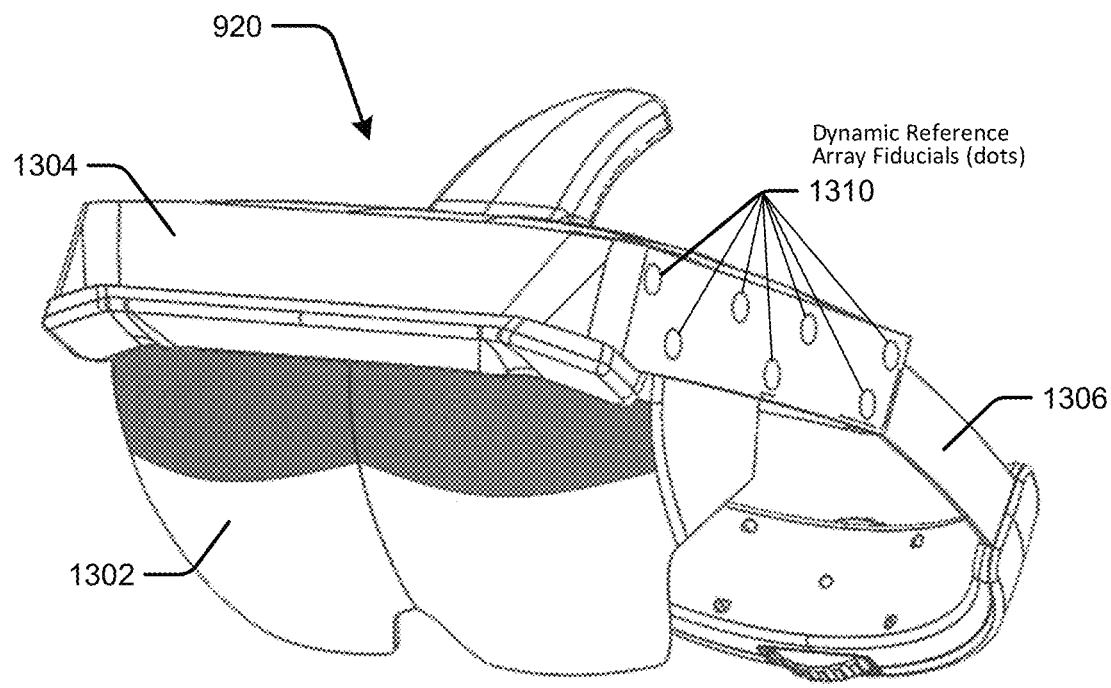
FIG. 13 illustrates an XR headset which is configured in accordance with some embodiments of the present disclosure.

FIG. 12 illustrates a block diagram view of the components of a surgical system that include a pair of XR headsets 920 (head-mounted displays HMD1 and HMD2), which may correspond to the XR headset 920 shown in FIG. 13 and operate in accordance with some embodiments of the present disclosure.

Referring to the example scenario of FIG. 12, the assistant 612 and surgeon 610 are both wearing the XR headsets 920, respectively. It is optional for the assistant 612 to wear the XR headset 920. The XR headsets 920 are configured to provide an interactive environment through which the wearers can view and interact with information related to a surgical procedure as will be described further below. This interactive XR based environment may eliminate a need for the tech personnel 614 shown in FIG. 6 to be present in the operating room and may eliminate a need for use of the display 34 shown in FIG. 6. Each XR headset 920 can include one or more cameras that are configured to provide an additional source of tracking of DRAs or other reference arrays attached to surgical tools, a patient's anatomical structure, the end effector 26, and/or other equipment. In the example of FIG. 12, XR headset 920 has a field-of-view (FOV) 1202 for tracking DRAs and other objects, XR headset 920 has a FOV 1212 partially overlapping FOV 1202 for tracking DRAs and other objects, and the tracking cameras 46 has another FOV 600 partially overlapping FOVs 1202 and 1212 for tracking DRAs and other objects.

If one or more cameras is obstructed from viewing a DRA attached to a tracked object, e.g., a surgical tool, but the DRA is in view of one or more other cameras the tracking subsystem 830 and/or navigation controller 828 can continue to track the object seamlessly without loss of navigation. Additionally, if there is partial occlusion of the DRA from the perspective of one camera, but the entire DRA is visible via multiple camera sources, the tracking inputs of the cameras can be merged to continue navigation of the DRA. One of the XR headsets and/or the tracking cameras 46 may view and track the DRA on another one of the XR headsets to enable the computer platform 910 (FIGS. 9 and 14), the tracking subsystem 830, and/or another computing component to determine the pose of the DRA relative to one or more defined coordinate systems, e.g., of the XR headsets 920, the tracking cameras 46, and/or another coordinate system defined for the patient, table, and/or room.

The XR headsets 920 can be operatively connected to view video, pictures, and/or other received information and/or to provide commands that control various equipment in the surgical room, including but not limited to neuromonitoring, microscopes, video cameras, and anesthesia systems. Data from the various equipment may be processed and displayed within the headset, for example the display of patient vitals or the microscope feed.

Example XR Headset Components and Integration to Navigated Surgery, Surgical Robots, and Other Equipment FIG. 13 illustrates an XR headset 920 which is configured in accordance with some embodiments of the present disclosure. The XR headset includes a headband 1306 configured to secure the XR headset to a wearer's head, an electronic component enclosure 1304 supported by the headband 1306, and a display screen 1302 that extends laterally across and downward from the electronic component enclosure 1304. The display screen 1302 may be a see-through LCD display device or a semi-reflective lens that reflects images projected by a display device toward the wearer's eyes. A set of DRA fiducials 1310, e.g., dots, are painted or attached in a spaced apart known arranged on one or both sides of the headset. The DRA on the headset enables the tracking cameras on the auxiliary tracking bar to track pose of the headset 920 and/or enables another XR headset to track pose of the headset 920.

The display screen 1302 operates as a see-through display screen, also referred to as a combiner, that reflects light from display panels of a display device toward the user's eyes. The display panels can be located between the electronic component enclosure and the user's head, and angled to project virtual content toward the display screen 1302 for reflection toward the user's eyes. The display screen 1302 is semi-transparent and semi-reflective allowing the user to see reflected virtual content superimposed on the user's view of a real-world scene. The display screen 1302 may have different opacity regions, such as the illustrated upper laterally band which has a higher opacity than the lower laterally band. Opacity of the display screen 1302 may be electronically controlled to regulate how much light from the real-world scene passes through to the user's eyes. A high opacity configuration of the display screen 1302 results in high-contrast virtual images overlaid on a dim view of the real-world scene. A low opacity configuration of the display screen 1302 can result in more faint virtual images overlaid on a clearer view of the real-world scene. The opacity may be controlled by applying an opaque material on a surface of the display screen 1302.

Figure 14:
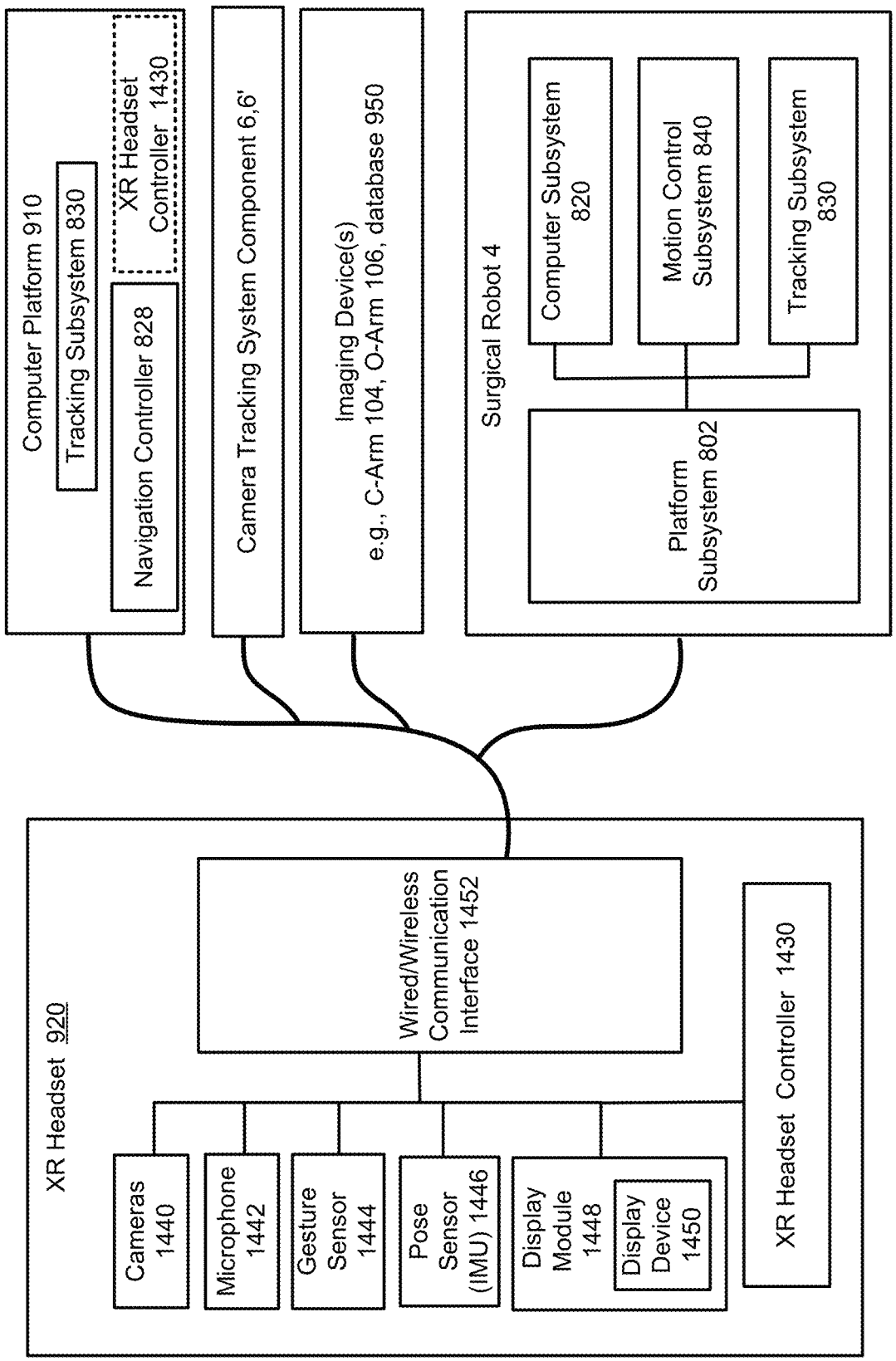
FIG. 14 illustrates electrical components of the XR headset that can be operatively connected to a computer platform, imaging device(s), and/or a surgical robot in accordance with some embodiments of the present disclosure.

According to some embodiments, the surgical system includes an XR headset 920 and an XR headset controller, e.g., controller 1430 in FIG. 14. The XR headset 920 is configured to be worn by a user during a surgical procedure and has a see-through display screen 1302 that is configured to display an XR image and to allow at least a portion of a real-world scene to pass therethrough for viewing by the user. The XR headset 920 also includes an opacity filter positioned between at least one of the user's eyes and the real-world scene when the see-through display screen 1302 is viewed by the user. The opacity filter is configured to provide opaqueness to light from the real-world scene. The XR headset controller is configured to communicate with a navigation controller, e.g., controller(s) 828A, 828B, and/or 828C in FIG. 14, to receive navigation information from the navigation controller which provides guidance to the user during the surgical procedure on an anatomical structure, and is further configured to generate the XR image based on the navigation information for display on the see-through display screen 1302.

Opacity of the display screen 1302 may be configured as a gradient having a more continuously changing opacity with distance downward from a top portion of the display screen 1302. The gradient's darkest point can be located at the top portion of the display screen 1302, and gradually becoming less opaque further down on the display screen 1302 until the opacity is transparent or not present. In an example further embodiment, the gradient can change from about 90% opacity to entirely transparent approximately at the mid-eye level of the display screen 1302. With the headset properly calibrated and positioned, the mid-eye level can correspond to the point where the user would look straight out, and the end of the gradient would be located at the "horizon" line of the eye. The darker portion of the gradient will allow crisp, clear visuals of the virtual content and help to block the intrusive brightness of the overhead operating room lights.

Using an opacity filter in this manner enables the XR headset 920 to provide virtual reality (VR) capabilities, by substantially or entirely blocking light from the real-world scene, along an upper portion of the display screen 1302 and to provide AR capabilities along a middle or lower portion of the display screen 1302. This allows the user to have the semi-translucence of AR where needed and allowing clear optics of the patient anatomy during procedures. Configuring the display screen 1302 as a gradient instead of as a more constant opacity band can enable the wearer to experience a more natural transition between a more VR type view to a more AR type view without experiencing abrupt changes in brightness of the real-world scene and depth of view that may otherwise strain the eyes such as during more rapid shifting between upward and downward views.

The display panels and display screen 1302 can be configured to provide a wide field of view see-through XR display system. In one example configuration they provide an 80° diagonal field-of-view (FOV) with 55° of vertical coverage for a user to view virtual content. Other diagonal FOV angles and vertical coverage angles can be provided through different size display panels, different curvature lens, and/or different distances and angular orientations between the display panels and curved display screen 1302.

FIG. 14 illustrates electrical components of the XR headset 920 that can be operatively connected to the computer platform 910, to one or more of the imaging devices, such as the C-arm imaging device 104, the O-arm imaging device 106, and/or the image database 950, and/or to the surgical robot 800 in accordance with various embodiments of the present disclosure.

The XR headset 920 provides an improved human interface for performing navigated surgical procedures. The XR headset 920 can be configured to provide functionalities, e.g., via the computer platform 910, that include without limitation any one or more of: identification of hand gesture based commands and/or voice based commands, display XR graphical objects on a display device 1450. The display device 1450 may be a video projector, flat panel display, etc., which projects the displayed XR graphical objects onto the display screen 1302. The user can view the XR graphical objects as an overlay anchored to particular real-world objects viewed through the display screen 1302 (FIG. 13). The XR headset 920 may additionally or alternatively be configured to display on the display screen 1450 video feeds from cameras mounted to one or more XR headsets 920 and other cameras.

Electrical components of the XR headset 920 can include a plurality of cameras 1440, a microphone 1442, a gesture sensor 1444, a pose sensor (e.g., inertial measurement unit (IMU) 1446, a display module 1448 containing the display device 1450, and a wireless/wired communication interface 1452. As will be explained below, the cameras 1440 of the XR headset may be visible light capturing cameras, near infrared capturing cameras, or a combination of both.

The cameras 1440 may be configured operate as the gesture sensor 1444 by capturing for identification user hand gestures performed within the field of view of the camera(s) 1440. Alternatively the gesture sensor 1444 may be a proximity sensor and/or a touch sensor that senses hand gestures performed proximately to the gesture sensor 1444 and/or senses physical contact, e.g. tapping on the sensor or the enclosure 1304. The pose sensor 1446, e.g., IMU, may include a multi-axis accelerometer, a tilt sensor, and/or another sensor that can sense rotation and/or acceleration of the XR headset 920 along one or more defined coordinate axes. Some or all of these electrical components may be contained in the component enclosure 1304 or may be contained in another enclosure configured to be worn elsewhere, such as on the hip or shoulder.

As explained above, the surgical system 2 includes a camera tracking system component 6/6' and a tracking subsystem 830 which may be part of the computer platform 910. The surgical system may include imaging devices (e.g., C-arm 104, O-arm 106, and/or image database 950) and/or a surgical robot 4. The tracking subsystem 830 is configured to determine a pose of DRAs attached to an anatomical structure, an end effector, a surgical tool, etc. A navigation controller 828 is configured to determine a target pose for the surgical tool relative to an anatomical structure based on a surgical plan, e.g., from a surgical planning function performed by the computer platform 910 of FIG. 9, defining where a surgical procedure is to be performed using the surgical tool on the anatomical structure and based on a pose of the anatomical structure determined by the tracking subsystem 830. The navigation controller 828 may be further configured to generate steering information based on the target pose for the surgical tool, the pose of the anatomical structure, and the pose of the surgical tool and/or the end effector, where the steering information indicates where the surgical tool and/or the end effector of a surgical robot should be moved to perform the surgical plan. Various of the cameras 1440 of the XR headset 920 may be connected to the camera tracking system component 6/6' to track poses of DRAs, user's hand(s), etc.

The electrical components of the XR headset 920 can be operatively connected to the electrical components of the computer platform 910 through a wired/wireless interface 1452. The electrical components of the XR headset 920 may be operatively connected, e.g., through the computer platform 910 or directly connected, to various imaging devices, e.g., the C-arm imaging device 104, the I/O-arm imaging device 106, the image database 950, and/or to other medical equipment through the wired/wireless interface 1452.

The surgical system 2 further includes at least one XR headset controller 1430 (also referred to as "XR headset controller" for brevity) that may reside in the XR headset 920, the computer platform 910, and/or in another system component connected via wired cables and/or wireless communication links. Various functionality is provided by software executed by the XR headset controller 1430. The XR headset controller 1430 is configured to receive navigation information from the navigation controller 828 which provides guidance to the user during the surgical procedure on an anatomical structure, and is configured to generate an XR image based on the navigation information for display on the display device 1450 for projection on the see-through display screen 1302.

The configuration of the display device 1450 relative to the display screen (also referred to as "see-through display screen") 1302 is configured to display XR images in a manner such that when the user wearing the XR headset 920 looks through the display screen 1302 the XR images appear to be in the real world. The display screen 1302 can be positioned by the headband 1306 in front of the user's eyes.

The XR headset controller 1430 can be within a housing that is configured to be worn on a user's head or elsewhere on the user's body while viewing the display screen 1302 or may be remotely located from the user viewing the display screen 1302 while being communicatively connected to the display screen 1302. The XR headset controller 1430 can be configured to operationally process signaling from the cameras 1440, the microphone 142, and/or the pose sensor 1446, and is connected to display XR images on the display device 1450 for user viewing on the display screen 1302. Thus, the XR headset controller 1430 illustrated as a circuit block within the XR headset 920 is to be understood as being operationally connected to other illustrated components of the XR headset 920 but not necessarily residing within a common housing (e.g., the electronic component enclosure 1304 of FIG. 13) or being otherwise transportable by the user. For example, the XR headset controller 1430 may reside within the computer platform 910 which, in turn, may reside within a housing of the computer tracking system component 6' shown in FIGS. 3B and 3C.

Example XR Headset Component Optical Arrangement

Figure 15:
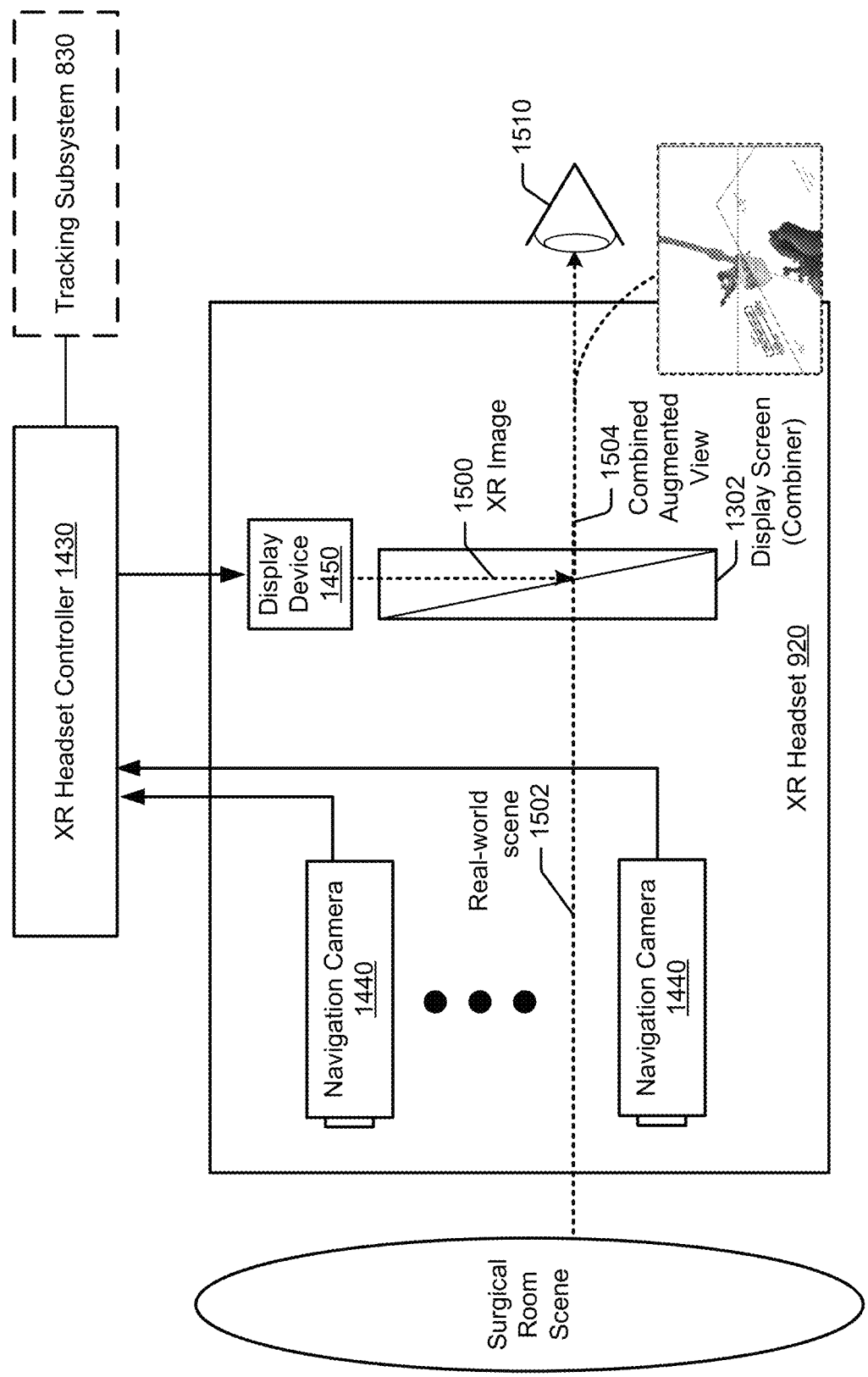
FIG. 15 illustrates a block diagram showing arrangement of optical components of the XR headset in accordance with some embodiments of the present disclosure.

FIG. 15 illustrates a block diagram showing arrange of optical components of the XR headset 920 in accordance with some embodiments of the present disclosure. Referring to FIG. 15, the display device 1450 is configured to display XR images generated by the XR headset controller 1430, light from which is projected as XR images 1500 toward the display screen 1302. The display screen 1302 is configured to combine light of the XR images 1500 and light from the real-world scene 1502 into a combined augmented view 1504 that is directed to the user's eye(s) 1510. The display screen 1302 configured in this manner operates as a see-through display screen. The XR headset 920 can include any plural number of tracking cameras 1440. The cameras 1440 may be visible light capturing cameras, near infrared capturing cameras, or a combination of both.

Example User Views Through the XR Headset

The XR headset operations can display both 2D images and 3D models on the display screen 1302. The 2D images may preferably be displayed in a more opaque band of the display screen 1302 (upper band) and the 3D model may be more preferably displayed in the more transparent band of the display screen 1302, otherwise known as the environmental region (bottom band). Below the lower band where the display screen 1302 ends the wearer has an unobstructed view of the surgical room. It is noted that where XR content is display on the display screen 1302 may be fluidic. It is possible that where the 3D content is displayed moves to the opaque band depending on the position of the headset relative to the content, and where 2D content is displayed can be placed in the transparent band and stabilized to the real world. Additionally, the entire display screen 1302 may be darkened under electronic control to convert the headset into virtual reality for surgical planning or completely transparent during the medical procedure. As explained above, the XR headset 920 and associated operations not only support navigated procedures, but also can be performed in conjunction with robotically assisted procedures.

Figure 16:
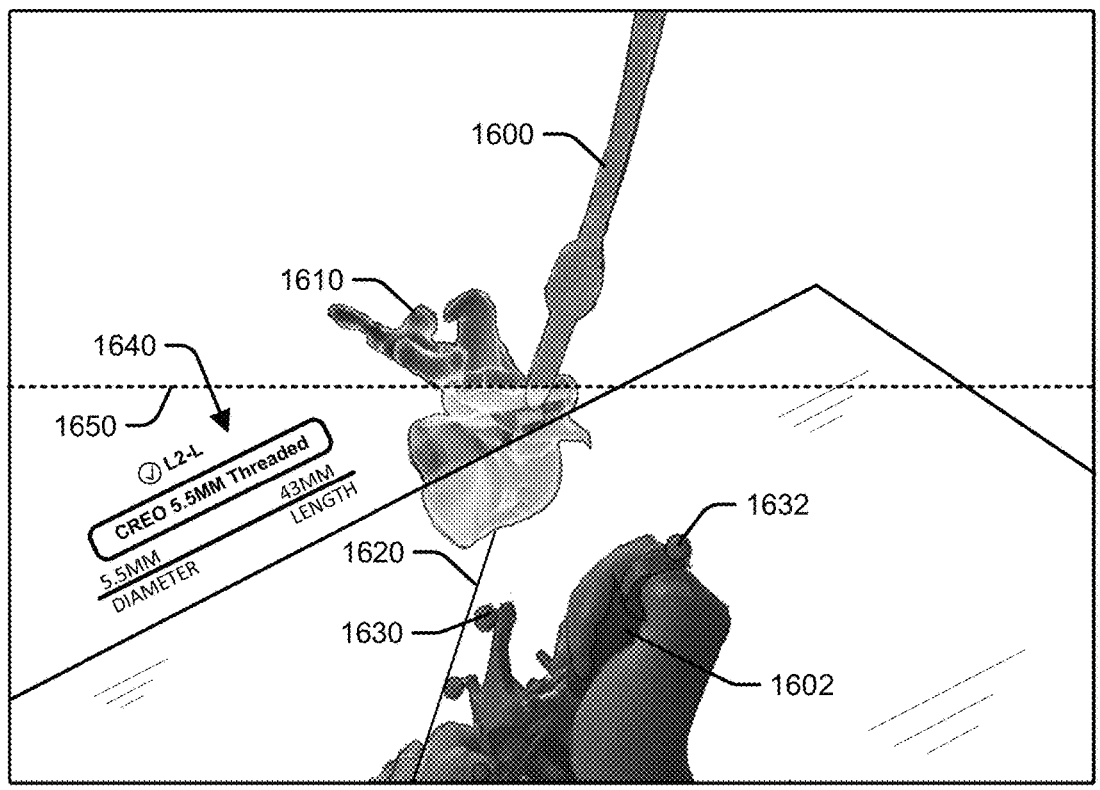
FIG. 16 illustrates an example view through the display screen of an XR headset for providing navigation assistance to manipulate a surgical tool during a medical procedure in accordance with some embodiments of the present disclosure.

FIG. 16 illustrates an example view through the display screen 1302 of the XR headset 920 for providing navigation assistance to a user who is manipulating a surgical tool 1602 during a medical procedure in accordance with some embodiments of the present disclosure. Referring to FIG. 16, when the surgical tool 1602 is brought in vicinity of a tracked anatomical structure so that dynamic reference arrays 1630 and 1632, connected to the surgical tool 1602, become within the field of view of the cameras 1440 (FIG. 15) and/or 46 (FIG. 6), a graphical representation 1600 of the tool can be displayed in 2D and/or 3D images in relation to a graphical representation 1610 of the anatomical structure. The user can use the viewed graphical representations to adjust a trajectory 1620 of the surgical tool 1602, which can be illustrated as extending from the graphical representation 2000 of the tool through the graphical representation 1610 of the anatomical structure. The XR headset 920 may also display textual information and other objects 1640. The dashed line 1650 extending across the viewed display screen represents an example division between different opacity level upper and lower bands.

Other types of XR images (virtual content) that can be displayed on the display screen 1302 can include, but are not limited to any one or more of:

1) 2D Axial, Sagittal and/or Coronal views of patient anatomy;
2) overlay of planned vs currently tracked tool and surgical implant locations;
3) gallery of preoperative images;
4) video feeds from microscopes and other similar systems or remote video conferencing;
5) options and configuration settings and buttons;
6) floating 3D models of patient anatomy with surgical planning information;
7) real-time tracking of surgical instruments relative to floating patient anatomy;
8) augmented overlay of patient anatomy with instructions and guidance; and
9) augmented overlay of surgical equipment.

Example Configuration of Cameras for Tracking System Component

Figure 17:
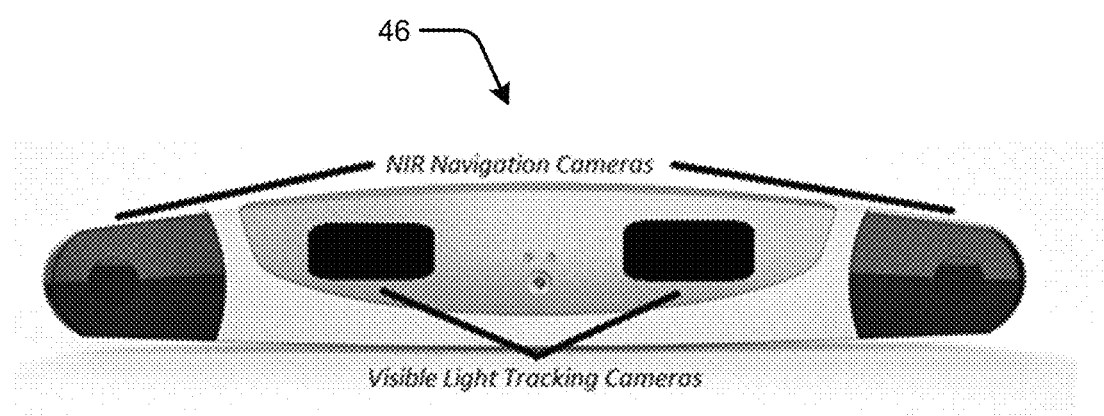
FIG. 17 illustrates an example configuration of an auxiliary tracking bar having two pairs of stereo cameras configured in accordance with some embodiments of the present disclosure.

FIG. 17 illustrates example configuration of an auxiliary tracking bar 46 having two pairs of stereo tracking cameras configured in accordance with some embodiments of the present disclosure. The auxiliary tracking bar 46 is part of the camera tracking system component of FIGS. 3A, 3B, and 3C. The stereo tracking cameras include a stereo pair of spaced apart visible light capturing cameras and another stereo pair of spaced apart near infrared capturing cameras, in accordance with one embodiment. Alternatively, only one stereo pair of visible light capturing cameras or only one stereo pair of near infrared capture cameras can used in the auxiliary tracking bar 46. Any plural number of near infrared and/or visible light cameras can be used.

Pose Measurement Chaining

As explained above, navigated surgery can include computer vision tracking and determination of pose (e.g., position and orientation in a six degree-of-freedom coordinate system) of surgical instruments, such as by determining pose of attached DRAs that include spaced apart fiducials, e.g., disks or spheres, arranged in a manner known to the camera tracking system. The computer vision uses spaced apart tracking cameras, e.g., stereo cameras, that are configured to capture near infrared and/or visible light. In this scenario, there are three parameters jointly competing for optimization: (1) accuracy, (2) robustness, and (3) user ergonomics during a surgical procedure.

Computer operations may combine (chain) measured poses in ways that can improve optimization of one or more of the above three parameters by incorporating additional tracking cameras mounted to one or more XR headsets. As shown in FIG. 17, a stereo pair of visible light tracking cameras and another stereo pair of near infrared tracking cameras can be attached to the auxiliary tracking bar of the camera tracking system component in accordance with some embodiments of the present disclosure. Operational algorithms are disclosed that analyze the pose of DRAs that are fully observed or partially observed (e.g., when less than all of the fiducials of a DRA are viewed by a pair of stereo cameras), and combine the observed poses or partial poses in ways that can improve accuracy, robustness, and/or ergonomics during navigated surgery.

As explained above, the XR headset may be configured to augment a real-world scene with computer generated XR images. The XR headset may be configured to provide an XR viewing environment by displaying the computer generated XR images on a see-through display screen that allows light from the real-world scene to pass therethrough for combined viewing by the user. Alternatively, the XR headset may be configured to provide a VR viewing environment by preventing or substantially preventing light from the real-world scene from being directly viewed by the user along the viewing path of the displayed XR images. An XR headset can be configured to provide both AR and VR viewing environments. In one embodiment, both AR and VR viewing environments are provided by lateral bands of substantially differing opacity arranged between the see-through display screen and the real-world scene, so that a VR viewing environment is provided for XR images aligned with a high opacity band and an AR viewing environment is provided for XR images aligned with the low opacity band. In another embodiment, both AR and VR viewing environments are provided by computer adjustable control of an opacity filter that variably constrains how much light from the real-world scene passes through a see-through display screen for combining with the XR images viewed by the user. Thus, the XR headset can also be referred to as an AR headset or a VR headset.

As was also explained above, the XR headset can include near infrared tracking cameras and/or visible light tracking cameras that are configured to track fiducials of DRAs connected to surgical instruments, patient anatomy, other XR headset(s), and/or a robotic end effector. Using near infrared tracking and/or visible light tracking on the XR headset provides additional tracking volume coverage beyond what cameras on a single auxiliary tracking bar can provide. Adding near infrared tracking cameras to the existing auxiliary tracking bar allows for the headset location to be tracked more robustly but less accurately than in visible light. Mechanically calibrating the visible and near infrared tracking coordinate systems enables the coordinate systems to be aligned sufficiently to perform 3D DRA fiducials triangulation operations using stereo matching to jointly identify pose of the DRA fiducials between the visible and near infrared tracking coordinate systems. Using both visible and near infrared tracking coordinate systems can enable any one or more of: (a) identifying tools that would not be identified using a single coordinate system; (b) increased pose tracking accuracy; (c) enabling a wider range of motion without losing tracking of surgical instruments, patient anatomy, and/or a robotic end effector; and (d) naturally track an XR headset in the same coordinate system as the navigated surgical instruments.

Figure 18:
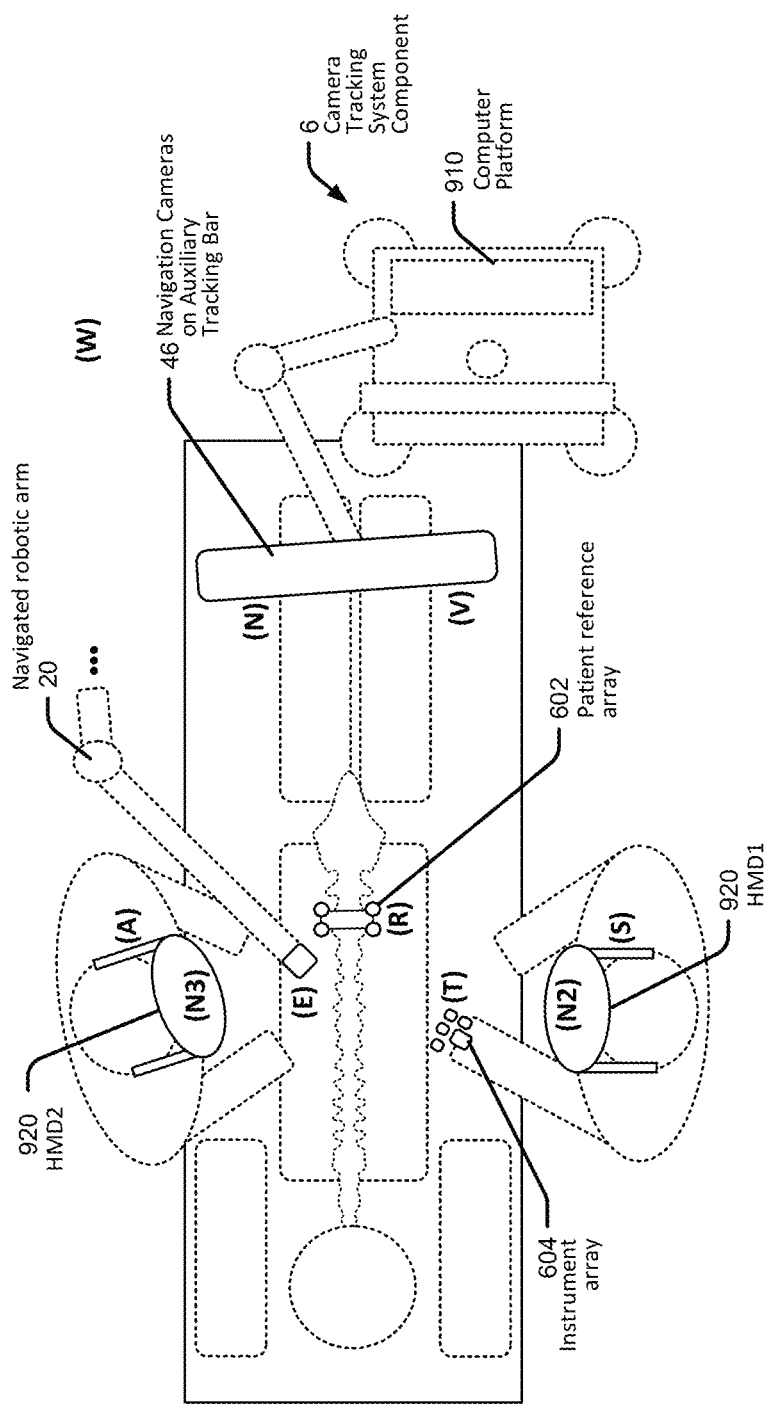
FIG. 18 illustrates a block diagram view of the components of a surgical system that includes tracking cameras in a pair of XR headsets and in an auxiliary tracking bar which collectively operate in accordance with some embodiments of the present disclosure.

FIG. 18 illustrates a block diagram view of the components of a surgical system that include tracking cameras in a pair of XR headsets 920 (head-mounted displays HMD1 and HMD2) and tracking cameras in a camera tracking bar in the camera tracking system component 6' which houses the computer platform 910. The computer platform 910 can include the tracking subsystem 830, the navigation controller 828, and the XR headset controller 1430 as was earlier shown in FIG. 14.

Referring to the surgical system of FIG. 18, a surgeon and an assistant are both wearing XR headsets HMD1 920 and HMD2 920, respectively, each if which includes tracking cameras that may be configured as shown in FIG. 13. It is optional for the assistant to wear the XR headset HMD2 920.

The combination of XR headsets HMD1 920 and HMD2 920 and the tracking cameras 46 on the auxiliary tracking bar can, in operation with the computer platform 910, more robustly track the example objects of a patient reference array (R), robotic end effector (E), and surgical tool (T) or instrument. The overlapping views from different perspectives that are provided by the XR headsets HMD1 920 and HMD2 920 and the tracking cameras 46 on the auxiliary tracking bar are shown in FIG. 12.

Each of the items labeled in FIG. 18 represent a unique coordinate system. Descriptions of the coordinate system labels are as follows:

A=visible light coordinate system of second headset HMD2 920;

N3=near infra-red (NIR) coordinate system of second headset HMD2 920;

S=visible light coordinate system of primary headset HMD1 920;

N2=NIR coordinate system of the primary headset HMD1 920;

N=NIR coordinate system of the auxiliary navigation bar 46;

V=visible light coordinate system of the auxiliary navigation bar 46;

R=NIR coordinate system of a patient reference fiducial array 602;

T=NIR coordinate system of a tracked tool 604;

E=NIR coordinate system of a tracked robot end effector on robotic arm 20; and W=Inertially navigated world coordinate system with stable gravity vector.

The spatial relationships of some of these labeled objects (and by extension, coordinate systems) can be measured and calibrated during the manufacturing process, when the equipment is installed in an operating room, and/or before a surgical procedure is to be performed. In the disclosed system, the following coordinate systems are calibrated: $T_{N2}^{S}$; $T_{N3}^{A}$; $T_{N}^{V}$, where the term "T" is defined as a six degree-of-freedom (6 DOF) homogeneous transformation between the two indicated coordinates systems. Thus, for example, the term $T_{N2}^{S}$ is a 6 DOF homogeneous transformation between the visible light coordinate system of the primary headset HMD1 920 and the NIR coordinate system of the primary headset HMD1 920.

In one embodiment, the XR headsets HMD1 920 and HMD2 920 have passive visible light fiducials painted or otherwise attached to them (coordinate systems S and A), such as the reference array fiducials 1310 shown in FIG. 13. The tracking cameras are spatially calibrated to these passive fiducials (coordinate systems N2 and N3).

As explained above, the cameras on the XR headset HMD1 920 and HMD2 920 and the tracking cameras 46 on the auxiliary tracking bar have partially overlapping field of views. If one or more of the cameras on the XR headset HMD1 920 are obstructed from viewing a DRA attached to a tracked object, e.g., a tracked tool (T), but the DRA is in view of the cameras of the other XR headset HMD2 920 and/or the tracking cameras 46 on the auxiliary tracking bar, the computer platform 910 can continue to track the DRA seamlessly without loss of navigation. Additionally, if there is partial occlusion of the DRA from the perspective of the cameras on the XR headset HMD1 920, but the entire DRA is visible via cameras of the other XR headset HMD2 920 and/or the tracking cameras 46 on the auxiliary tracking bar, the tracking inputs of the cameras can be merged to continue navigation of the DRA.

More particularly, the various coordinate systems can be chained together by virtue of independent observations the various camera systems provided by the XR headsets HMD1 920 and HMD2 920 and the tracking cameras 46 on the auxiliary tracking bar. For example, each of the XR headsets HMD1 920 and HMD2 920 may require virtual augmentation of the robotic end effector (E). While one XR headset HMD1 920 (N2) and the tracking cameras 46 on the auxiliary tracking bar (N) are able to see (E), perhaps the other XR headset HMD2 920 (N3) cannot. The location of (E) with respect to (N3) can still be computed via one of several different operational methods. Operations according to one embodiment performing chaining of poses from a patient reference (R). If the patient reference (R) is seen by (N3) and either one of (N) or (N2), the pose of (E) with respect to (N3) can be solved directly by either one of the following two equations:

$$T_{N3}^{E} = T_{N2}^{E} T_{R}^{N2} T_{N3}^{R} \text{ -or- } T_{N3}^{E} = T_{N}^{E} T_{N}^{R} T_{N3}^{R}$$

They key to this pose chaining is that the relationship between the frames at the end of each chain are inferred (circled and transported below). The chains can be arbitrarily long and are enabled by having more than one stereo camera system (e.g., N, N2, N3).

The camera tracking system can be configured to receive tracking information related to tracked objects from a first tracking camera (e.g., N3) and a second tracking camera (e.g., N2) during a surgical procedure. The camera tracking system can determine a first pose transform (e.g., $T_{N3}^{R}$) between a first object (e.g., R) coordinate system and the first tracking camera (e.g., N3) coordinate system based on first object tracking information from the first tracking camera (e.g., N3) which indicates pose of the first object (e.g., R). The camera tracking system can determine a second pose transform (e.g., $T_{R}^{N2}$) between the first object (e.g., R) coordinate system and the second tracking camera (e.g., N2) coordinate system based on first object tracking information from the second tracking camera (e.g., N2) which indicates pose of the first object (e.g., R). The camera tracking system can determine a third pose transform (e.g., $T_{N2}^{E}$) between a second object (e.g., E) coordinate system and the second tracking camera (e.g., N2) coordinate system based on second object tracking information from the second tracking camera (e.g., N2) which indicates pose of the second object (e.g., E). The camera tracking system can determine a fourth pose transform (e.g., $T_{N3}^{E}$) between the second object (e.g., E) coordinate system and the first tracking camera (e.g., N3) coordinate system based on combining the first, second, and third pose transforms.

In some further embodiments, the camera system can further determine pose of the second object (e.g., E) and the first tracking camera system (e.g., N3) coordinate system based on processing the tracking information through the fourth pose transform.

Because of the overlapping field of views of the various camera systems, the camera tracking system is capable of determining the pose of the second object (e.g., E) relative to first tracking camera (e.g., N3) when the first camera is blocked from seeing the second object (e.g., E). For example, in some embodiments the camera tracking system is further configured to determine the fourth pose transform (e.g., $T_{N3}^{E}$) between the second object (e.g., E) coordinate system and the first tracking camera (e.g., N3) coordinate system without use of any tracking information from the first tracking camera (e.g., N3) indicating pose of the second object (e.g., E).

The camera tracking system may achieve higher tracking accuracy by merging synchronized imagery from multiple camera systems. For example, the camera tracking system can determine pose of the second object (e.g., E) relative to first tracking camera (e.g., N3) by merging synchronized imagery of the second object (e.g., E) from multiple perspectives (first and second tracking cameras), and can use weighting which can be determined based on accuracy specs of the respective cameras. More particularly, the camera tracking system can be further configured to determine the fourth pose transform (e.g., $T_{N3}^{E}$) between the second object (e.g., E) coordinate system and the first tracking camera (e.g., N3) coordinate system based on second object tracking information from the first tracking camera (e.g., N3) which indicates pose of the second object (e.g., E) and further based on a result of the combining of the first, second, and third pose transforms.

The surgical system may be configured to display on the see-through display screen of an XR headset an XR image having a pose that is determined based on the fourth pose transform. The camera tracking system may be further configured to generate the XR image as a graphical representation of the second object (e.g., E) that is posed on the see-through display screen based on processing through the fourth pose transform the first object tracking information from the first and second tracking cameras and the second object tracking information from the second tracking camera.

As explained above, the camera tracking system can include a navigation controller 828 communicatively connected to the first tracking camera (e.g., N3) and the second tracking camera (e.g., N2) to receive the tracking information and configured to perform the determination of the first, second, third, and fourth pose transforms.

Registration of Surgical Tool Characteristics to a Reference Array Identified by Camera Tracking System During a surgical procedure, the camera tracking system can simultaneously track the poses of surgical tools which are being held or supported within the field-of-view of a set of tracking cameras, and can resume tracking of a surgical tool when it is moved from outside to inside that field-of-view, e.g., after being picked-up again. Many surgical tools require software configuration to track properly. Because the camera tracking system tracks poses of the reference arrays attached to or on the surgical tools, the camera tracking system should be informed of which surgical tool characteristics are registered to which of the tracked reference arrays. The navigation controller 828 (FIG. 14) can thereby operate with knowledge of the particular characteristics of the surgical tool. For example, registration of surgical tool characteristics of the distance from an identified reference array to a tip of the surgical tool enables the navigation controller 828 to navigate a surgeon's movement of the tool tip during a surgical procedure. Similarly, registration of a direction of curvature of a surgical tool relative to an identified reference array enables the navigation controller 828 to display an accurate graphical representation of the surgical tool through the XR headset 920 and accurately posed relative to a tracked anatomical structure during the surgical procedure.

The registration process is also referred to as a pairing process during which a user holds a surgical tool having a reference array in the field-of-view of the set of tracking cameras for identification of the reference array, and the user then define characteristics of that surgical tool, in accordance with some embodiments. The registration process is repeated for each combination of reference array and surgical tool characteristics that will be tracked during a surgical procedure, and can be further repeated when a reference array is detached from one type of surgical tool and attached to a different type of surgical tool. It can be important to enable a surgeon or other medical personnel wearing an XR headset to be able to time efficiently perform registration processes for a set of surgical tools, to assist the surgeon with avoiding making errors when registering surgical tool characteristics with reference arrays, and to reduce interruption of a surgeon's concentration before and during a surgical procedure.

Some further embodiments of the present disclosure are directed to using an XR headset during a registration process to register an identified reference array to characteristics of a surgical tool, and to display a representation of those characteristics through the XR headset so that a user can verify correctness of the registration. Using the XR headset during the registration process can provide a more intuitive, time efficient and reliable process for surgeons and other medical personnel (users) to register surgical tools with a camera tracking system before and/or during a surgical procedure.

Figure 19:
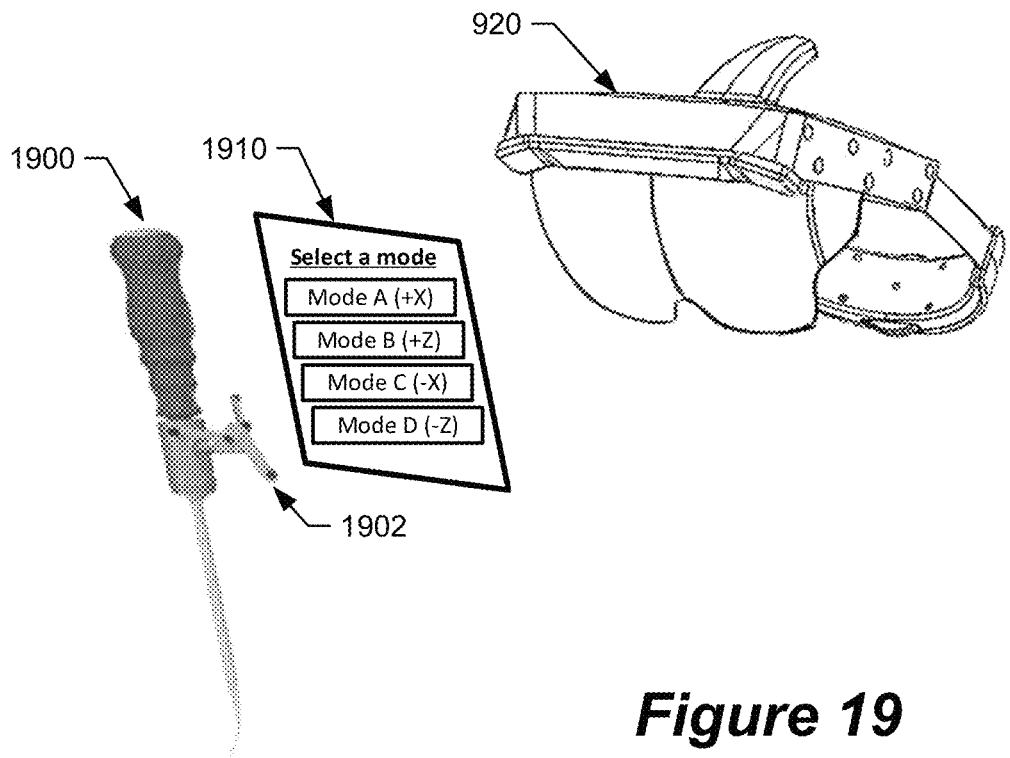
FIG. 19 illustrates a graphical representation of surgical tool characteristics displayed by the XR headset when a reference array is being registered to a surgical tool for use in computer assisted navigation of the surgical tool during surgery, in accordance with some embodiments of the present disclosure.
Figure 20:
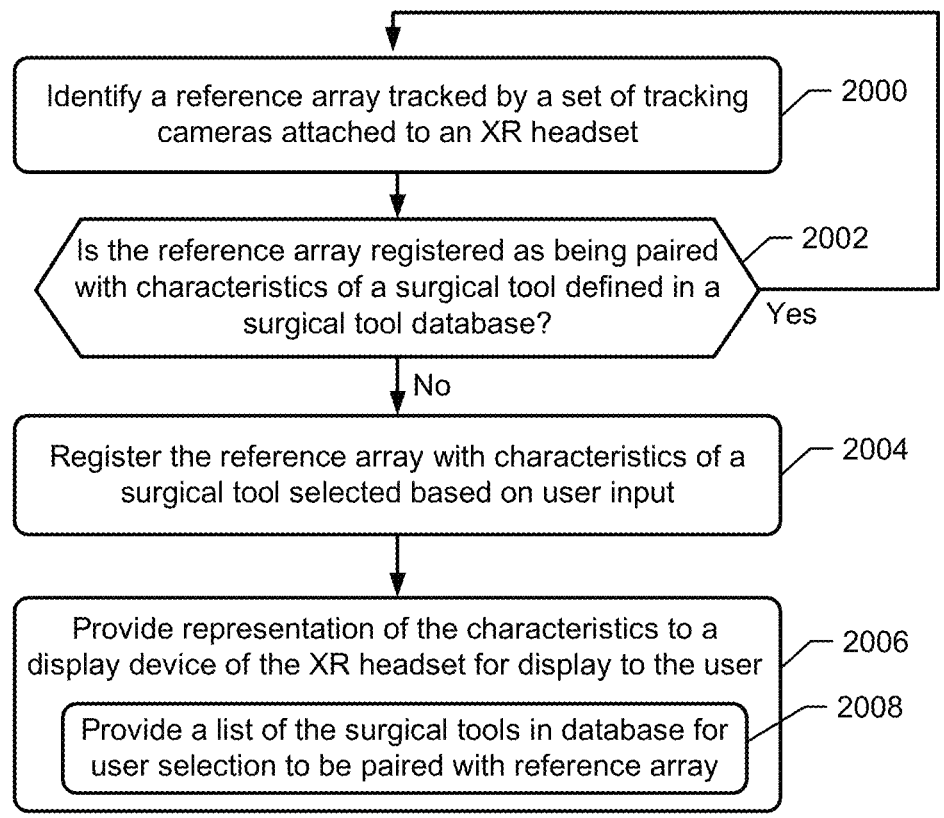
FIG. 20 illustrates a flowchart of registration operations performed by the camera tracking system to provide the graphical representation of the surgical tool characteristics in FIG. 19, in accordance with some embodiments of the present disclosure.

The registration process may be automatically initiated responsive to a reference array being brought into the field-of-view of a set of tracking cameras and the camera tracking system determining that the identified reference array has not yet been registered as being paired with characteristics of a surgical tool. FIG. 19 illustrates a graphical representation 1910 of surgical tool characteristics that can be displayed by the XR headset when a reference array 1902 is being registered to characteristics of a surgical tool 1900 for use in computer assisted navigation of the surgical tool 1900 during surgery, in accordance with some embodiments of the present disclosure. FIG. 20 illustrates a flowchart of registration operations performed by the camera tracking system (e.g., system 6 in FIG. 18), and which may provide the graphical representation of the surgical tool characteristics in FIG. 19, in accordance with some embodiments of the present disclosure.

Referring to FIGS. 19 and 20, the example XR headset includes a set of tracking cameras which may, for example, be contained in the electronic component enclosure 1304 of the XR headset 920 as shown in FIG. 13. The camera tracking system (e.g., system 6 in FIG. 18) identifies 2000 a reference array 1902 which is tracked by the set of tracking cameras, such as by identifying reference array in video streams from the tracking cameras. As explained above, reference arrays can be uniquely identified based on the differing orientations between the sets of fiducials forming respective reference arrays. The camera tracking system determines 2002 whether the identified reference array 1902 is registered as being paired with characteristics of one of a plurality of surgical tools defined in a surgical tool database. Based on the reference array 1902 being determined 2002 to not be registered and based on receiving user input, the camera tracking system registers 2004 the reference array 1902 as being paired with characteristics of the surgical tool 1900 which is selected among the plurality of surgical tools based on the user input. The camera tracking system then provides 2006 a representation of the characteristics to a display device of the XR headset 920 for display to the user.

Thus, in the example illustration of FIG. 19, a user can initiate registration by raising the surgical tool 1900 into the field-of-view of the set of tracking cameras attached to the XR headset 920. When an unregistered reference array comes into the field-of-view of the tracking cameras, the camera tracking system can cause a visual prompt to be displayed through the XR headset 920 which prompts the user to perform registration of the reference array to characteristics of the associated surgical tool. The camera tracking system receives video from the tracking cameras, identifies 2000 the reference array based on the spacing and relative, and determines 2002 that the identified reference array has not yet been registered as being paired with any defined characteristics of a surgical tool defined in the surgical tool database. The camera tracking system receives user input identifying characteristics of the surgical tool, and registers 2004 the reference array as being paired with characteristics of the surgical tool 1900. The camera tracking system.

Example surgical tool characteristics can include, without limitation, structural and/or operational characteristics of a drill, saw, screw driver, retractor, and implant such as a screw, spacer, interbody fusion device, plate, rod, etc.

The camera tracking system can facilitate the user's definition of the surgical tool characteristics that are to be registered with the identified reference array 1902, by providing 2008 a list of the surgical tools in the database for display through the XR headset 920 for user selection among to be registered with the reference array 1902. For example, based on the reference array 1902 being determined 2002 to not be registered, the camera tracking system can provide to the display device of the XR headset 920 a list of at least some of the plurality of the surgical tools defined in the surgical tool database for the user to select one of the surgical tools to be registered as paired with the reference array 1902.

Some surgical tools are asymmetric and require additional characteristic configuration during registration. In the particular example of FIG. 19, the tip of the surgical tool 1900 curves off to one side and requires a user to select one of four modes displayed as a list 1910 during registration based on which direction the tool tip is curving with respect to the reference array 1902. The four modes include Mode A corresponding to +X curvature, Mode B corresponding to +Z curvature, Mode C corresponding to −X curvature, and Mode D corresponding to −Z curvature. Use of the XR headset 920 during such surgical tool registration can intuitively facilitate the user's registration of the surgical tool characteristics as well as provide safeguards to ensure the correct characteristics are registered to the correct reference array 1902.

The camera tracking system may be configured to track movement of a user's hand and to identify hand gestures as user input during the tool registration process. For example, in the example of FIG. 19, a user may be able to virtually touch-select one of the modes (Mode A-D) displayed in the virtual space to have the surgical tool characteristics which have been defined for the selected mode to become registered to the reference array 1902. More particularly, the camera tracking system may be configured to determine the user's selection among the displayed list 1910, based on tracking information from the set of tracking cameras indicating pose of a hand of the user in XR space relative to the displayed list 1910.

The camera tracking system may display the characteristics and other information so that it appears near to the surgical tool 1900 when viewed by the surgeon through the XR headset 920, such as illustrated by the listing 1910 that is graphically displayed adjacent to the surgical tool 1900 when viewed by the surgeon through the XR headset 920. In one embodiment, the camera tracking system receives tracking information from the set of tracking cameras indicating pose of the reference array 1902 relative to the XR headset 920, and determines a pose for how the representation of the characteristics (e.g., tool information) is to be displayed relative to the reference array based on the tracking information. The camera tracking system then controls the XR headset 920 to display the representation of the characteristics with the determined pose relative to the reference array 1902.

Once the surgical tool 1900 has been registered to the reference array 1902, the camera tracking system can display visual feedback of the registered characteristics to enable the surgeon to verify accuracy of registration. Displaying informational description about the registered surgical tool 1900 provides one level of verification to ensure that the correct surgical tool has been registered. Another level of verification can include displaying a 2D or 3D graphical representation of the surgical tool characteristics that have been, or are being, registered to the reference array 1902.

Figure 21:
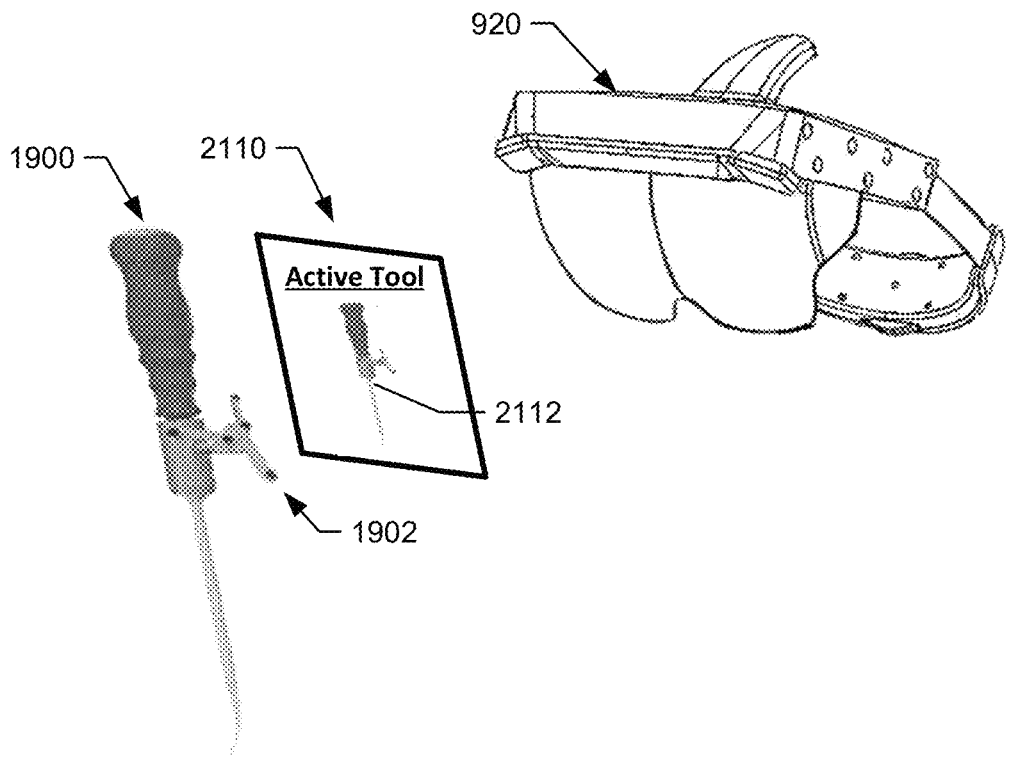
FIG. 21 illustrates a graphical representation of a registered actively-used surgical tool which is displayed by the XR headset, in accordance with some embodiments of the present disclosure.
Figure 22:
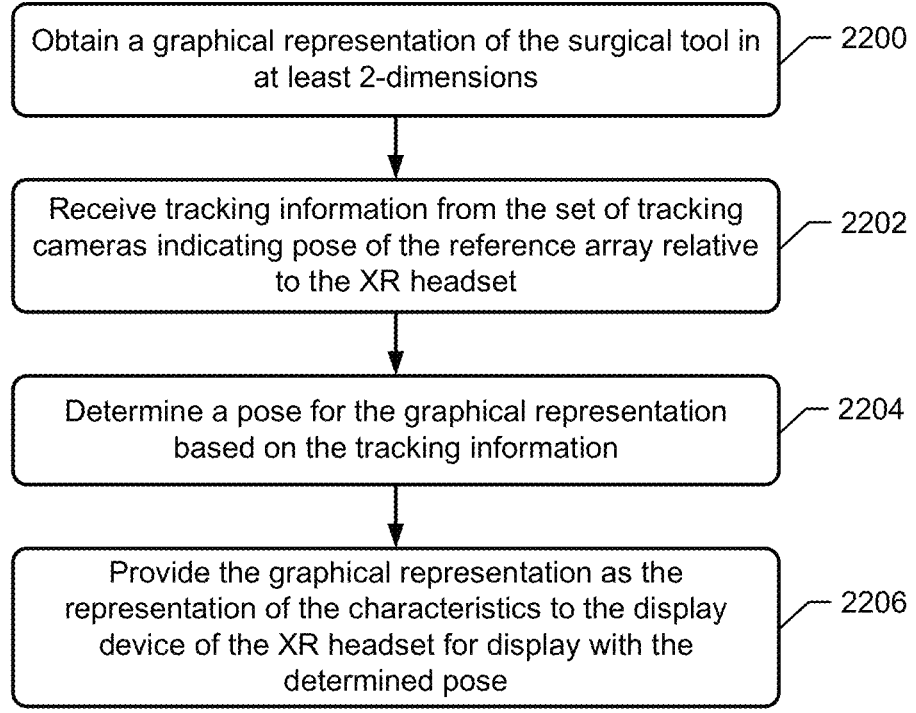
FIG. 22 illustrates a flowchart of operations performed by the camera tracking system to provide the graphical representation of the registered actively-used surgical tool in FIG. 21, in accordance with some embodiments of the present disclosure.

FIG. 21 illustrates a graphical representation 2112 of a registered actively-used surgical tool 1900 which is displayed by the XR headset 920, in accordance with some embodiments of the present disclosure. FIG. 22 illustrates a flowchart of operations performed by the camera tracking system to provide the graphical representation 2112 of the registered actively-used surgical tool 1900 in FIG. 21, in accordance with some embodiments of the present disclosure.

Referring to FIGS. 21 and 22, the camera tracking system obtains 2200 a graphical representation 2112 of the surgical tool 1900 in at least 2-dimensions (i.e., a 2D model or 3D model), and receives 2202 tracking information from the set of tracking cameras indicating pose of the reference array 1902 relative to the XR headset 920. The camera tracking system determines 2204 a pose for the graphical representation 2112 based on the tracking information, and provides 2206 the graphical representation 2112 as the representation of the characteristics to the display device of the XR headset 920 for display with the determined pose.

In the illustrated example of FIG. 21, the camera tracking system has obtained a 3D representation 2112 of the registered surgical tool 1900, and displays the 3D representation 2112 in a feedback window 2110 which is adjacent to the surgical tool 1900 and with a pose that matches a current pose of the surgical tool 1900. A surgeon holding the surgical tool 1900 in front of the XR headset 920 is thereby shown which characteristics of a particular one of the surgical tools that have been registered to the reference array 1902, which enables the surgeon to visually compare the displayed 3D representation 2112 to the physical surgical tool 1900 to verify the correctness of the registration. These operations can, for example, enable a surgeon to confirm that the correct mode among the list 1910 (FIG. 19) has been selected by comparing the tool tip bend direction shown in the graphical representation 2112 to that of the physical surgical tool 1900.

When the set of tracking cameras identifies a reference array connected to a surgical tool, the camera tracking system may determine how accurately, i.e., a measure of tracking accuracy (also called tracking quality), the reference array is being tracked by the tracking cameras. The tracking accuracy can become degraded when the tracking cameras are not positioned properly relative to the surgical tool 2100, when a location of one or more of the fiducials has been moved through deformation of the fiducials support structure, and/or when a fiducial is damaged and/or has become covered by bodily fluid or other material. It can therefore be important to enable a surgeon to be able to observe the tracking accuracy while viewing the surgical tool 2100 through the XR headset 920.

Figure 23:
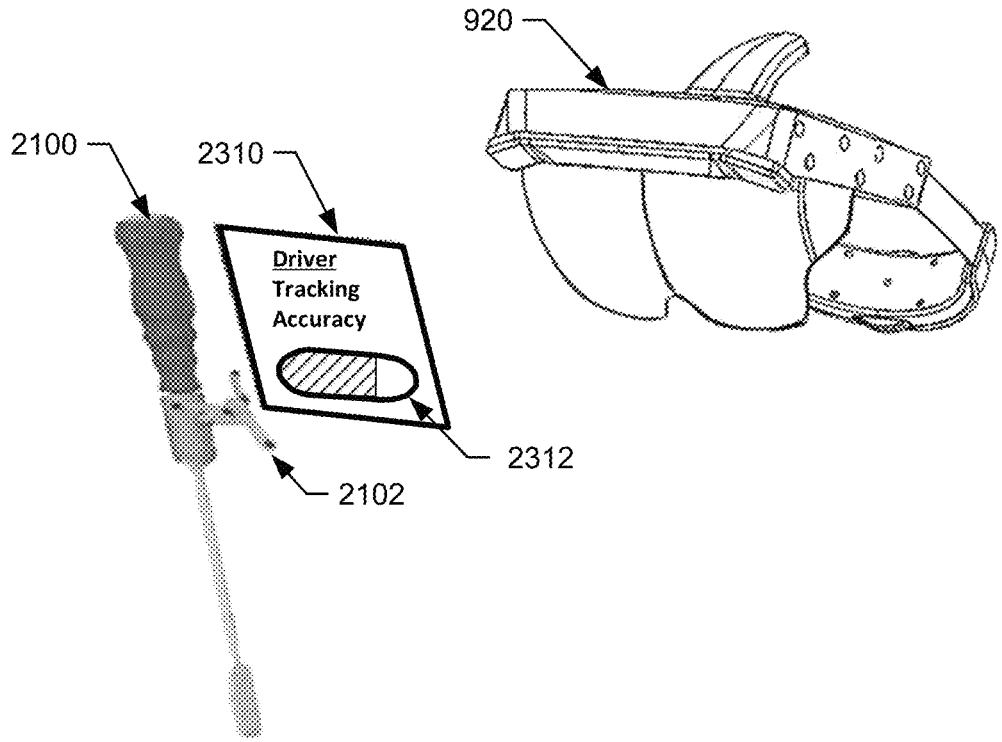
FIG. 23 illustrates a graphical representation of tracking accuracy information displayed by the XR headset for a registered reference array while a user is viewing the surgical tool, in accordance with some embodiments of the present disclosure.
Figure 24:
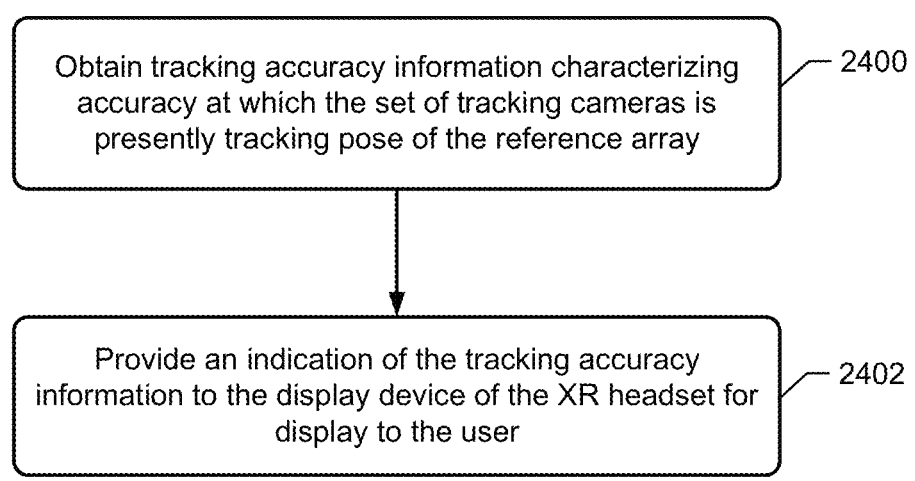
FIG. 24 illustrates a flowchart of operations performed by the camera tracking system to provide the graphical representation of the tracking accuracy information in FIG. 23, in accordance with some embodiments of the present disclosure.

FIG. 23 illustrates a graphical representation 2312 of tracking accuracy information displayed by the XR headset 920 for a registered reference array 2102 while a user is viewing the surgical tool 2100, in accordance with some embodiments of the present disclosure. FIG. 24 illustrates a flowchart of operations performed by the camera tracking system to provide the graphical representation 2312 of the tracking accuracy information in FIG. 23, in accordance with some embodiments of the present disclosure.

Referring to FIGS. 23 and 24, the camera tracking system obtains 2400 tracking accuracy information characterizing accuracy at which the set of tracking cameras is presently tracking pose of the reference array 2102. The camera tracking system then provides 2402 an indication 2312 of the tracking accuracy information to the display device of the XR headset for display to the user. In the illustrative example of FIG. 23, the camera tracking system has displayed the tracking accuracy in the form of a graphical sliding scale within a tracking quality window 2310 viewable through the XR headset 920, although other graphical indications, textual descriptions (e.g., poorly-tracked, well-tracked, fully-tracked), and/or colored graphical indicia could be displayed.

The tracking accuracy may be determined based on how closely the measured positions of the fiducials forming the reference array 2102 match the positions of the fiducials that have been earlier defined for the reference array 2102 (e.g., a defined model for the identified reference array 2101), and/or based on how well the shape of the fiducials identified in video from the tracking cameras fits a defined shape of the fiducials (e.g., a defined ellipse shape). Alternatively or additionally, the tracking accuracy may be determined based on comparing a pose of the reference array 2102 to an expected pose when a defined location (e.g., tip) of the surgical tool is touched to a known location (e.g., a calibration divot on another registered reference array). The graphical representation of the tracking accuracy is generated to visually indicate the determined or accuracy at which the tracking cameras are tracking the reference array 2102.

The camera tracking system may be configured to display other information associated with the surgical tool 2100. To ensure that surgical tools can operate properly during surgical procedure, such as by not being structurally bent or lacking proper range of extension and/or angular motion, they can be regularly verified. For example, whether a surgical tool has a bent tip can be determined by positioning the tool tip at a location known to the camera tracking system, such as a known calibration divot, to confirm that the tracked reference array has an expected pose while the tool tip is at the known location. The results of this verification process can be stored in a surgical database, and displayed near the surgical tool to ensure that users are notified if the tool should not be used during a surgical procedure and/or whether enough time has transpired since a last verification such that the surgical tool should be re-verified before use. The camera tracking system may be configured to obtain a last verified date which indicates when the surgical tool 2100 was last verified to not have structural deformation, and to provide an indication of the last verified date to the display device of the XR headset 920 for display to the user.

Such graphical characteristics of a surgical tool can be selectively displayed depending upon whether the surgical tool is within an inspection region that has been defined relative to location XR headset 920. For example, when the surgeon holds the surgical tool so that it is above the surgeon's chest or neck within a defined inspection region, the camera tracking system can respond by displaying the registered characteristics of the surgical tool. In contrast, while the surgeon holds the surgical tool below the inspection region the camera tracking system can prevent the display of the registered characteristics of the surgical tool. This enables the surgeon to quickly inspect displayed characteristics that have been registered with a particular surgical tool by holding within the inspection region, and then having those display characteristics disappear from view as the surgical tools moved outside the inspection region in order to, for example, avoid interfering with the surgeon's view of a surgical site during use of the tool in a surgical procedure.

The camera tracking system may compare a shape of a portion of the tool (e.g., shape of the shaft of tool 2100) to a defined template shape for the tool 2100. Differences in the compared shape that exceed a defined threshold may cause a notification to be displayed through the XR headset 920. For example, a graphical highlight may be displayed overlapping a portion of the shaft of tool 2100 that appears to deviate from the defined template shape, in order to intuitively notify the user of a potential problem which may necessitate replacement of the shaft and/or the tool 2100.

Figure 26:
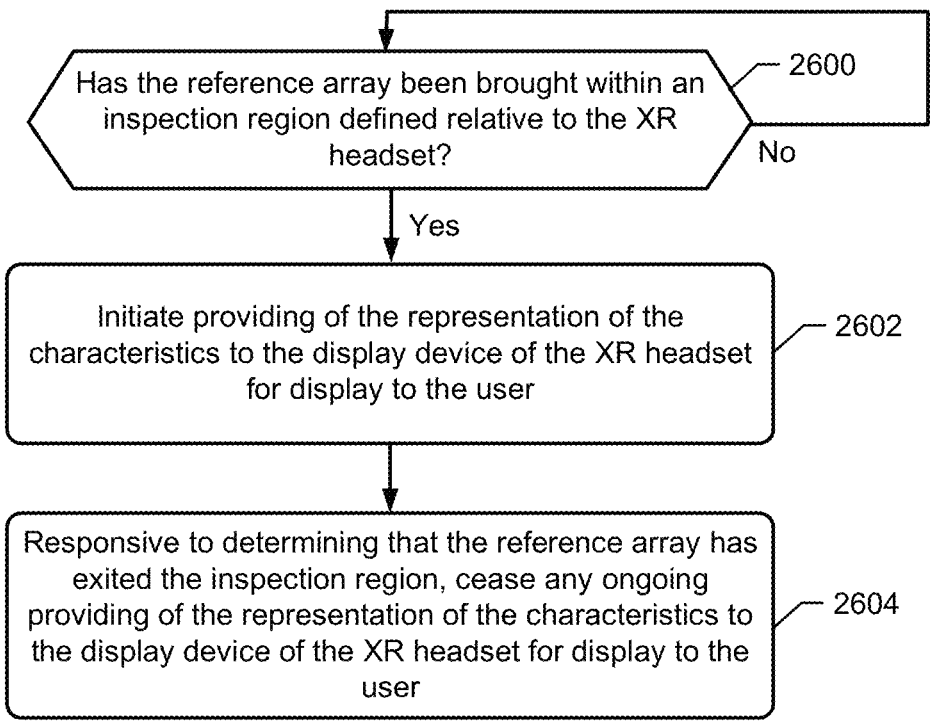
FIG. 26 illustrates a flowchart of operations performed by the camera tracking system to selectively display characteristics of a surgical tool registered with a reference array depending upon whether the reference array is within an inspection region defined relative to the XR headset, in accordance with some embodiments of the present disclosure.

FIG. 26 illustrates a flowchart of operations performed by the camera tracking system to selectively display characteristics of a surgical tool registered with a reference array depending upon whether the reference array is within an inspection region defined relative to the XR headset, in accordance with some embodiments of the present disclosure.

Referring to FIG. 26, the camera tracking system is configured to determine 2600 when the reference array has been brought within an inspection region which is defined relative to location of the XR headset. Responsive to determining that the reference array has been brought within the inspection region, the camera tracking system initiates 2602 the providing of the representation of the characteristics to the display device of the XR headset for display to the user. In contrast, responsive to determining that the reference array has exited the inspection region, the camera tracking system ceases 2604 any ongoing providing of the representation of the characteristics to the display device of the XR headset for display to the user.

Figure 25:
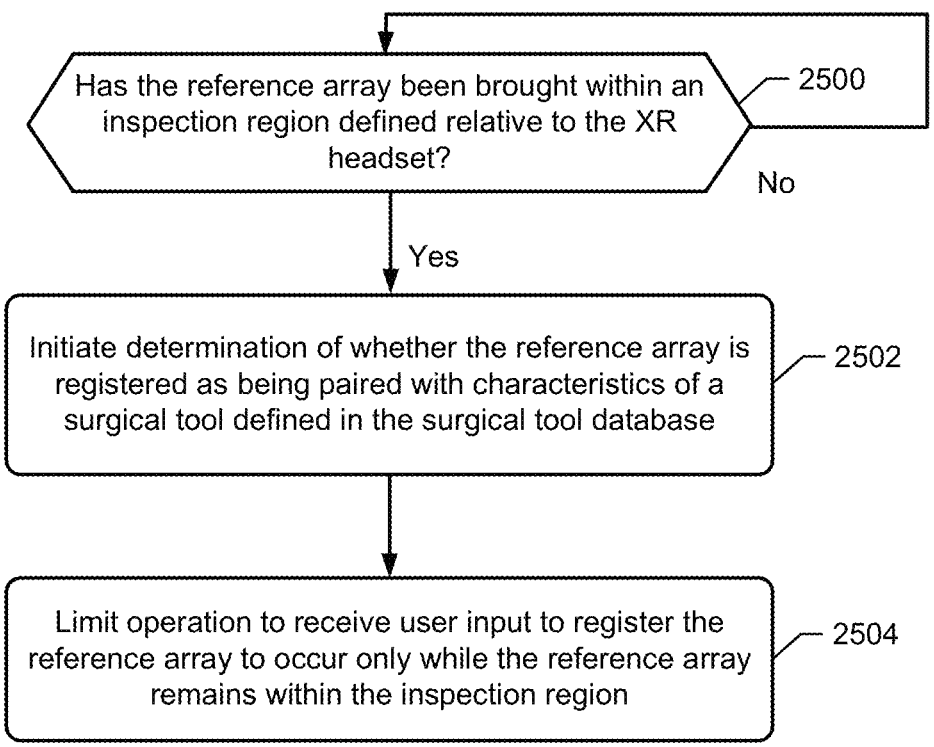
FIG. 25 illustrates a flowchart of operations performed by the camera tracking system to selectively allow user registration of a reference array depending upon whether the reference array is within an inspection region defined relative to the XR headset, in accordance with some embodiments of the present disclosure.

An inspection region can be similarly defined to selectively enable a registration process to be performed for a surgical tool. FIG. 25 illustrates a flowchart of operations performed by the camera tracking system to selectively allow user registration of a reference array depending upon whether the reference array is within an inspection region defined relative to the XR headset, in accordance with some embodiments of the present disclosure.

Referring to FIG. 25, the camera tracking system is configured to determine 2500 when the reference array has been brought within an inspection region which is defined relative to location of the XR headset. Responsive to determining that the reference array has been brought within the inspection region, the camera tracking system initiates 2502 the determination of whether the reference array is registered as being paired with characteristics of one of a plurality of surgical tools defined in the surgical tool database. In contrast, the camera tracking system is configured to limit 2504 operation to receive user input to register the reference array as paired with characteristics of one of the plurality of surgical tools defined in the surgical tool database, to occur only while the reference array remains within the inspection region.

During a surgical procedure, one or more of the fiducials which are arranged to form a reference array can become obscured or otherwise not viewable by the set of tracking cameras because, for example, it has been damaged during a surgical procedure and/or has become covered by bodily fluid or other material. Some embodiments are directed to displaying information that shows which fiducials in a reference array are being tracked by the tracking cameras. For example, when tracking fails because one or more fiducials are occluded, the remaining fiducials can be reported as strays. In this case, the camera tracking system can identify poses (e.g., position) of some of the fiducials but does not have enough information to match the identified fiducials to one of the plurality of predefined reference arrays. However, the poses of the stray fiducials can still be used to inform the surgeon as to which of the fiducials are being tracked. Virtual representations of each tracked fiducial can be displayed through the XR headset at their poses (e.g., positions) in the real world as viewed through the XR headset. In this manner, the surgeon will know which of the fiducials are occluded or need adjustment or replacement.

Figure 27:
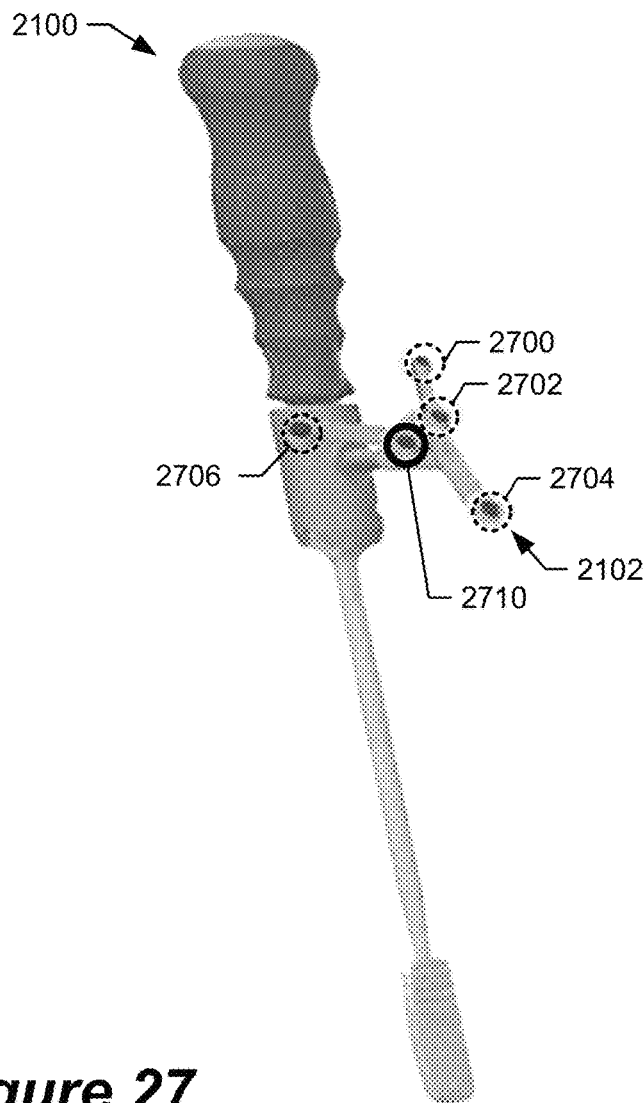
FIG. 27 illustrates a surgical tool viewed through the XR headset with graphical indicia displayed at least partially overlapping identified poses of fiducials of the reference array and another graphical indicia displayed at least partially overlapping an estimated pose of a missing fiducial, in accordance with some embodiments of the present disclosure.

Referring to the example embodiment of FIG. 27, a surgical tool 2100 having five fiducials forming the reference array 2102 is viewed through the XR headset 920 with graphical indicia 2700, 2702, 2704, 2706 that are displayed at least partially overlapping identified poses of four of the fiducials of the reference array 2102 and another graphical indicia 2710 that is displayed at least partially overlapping an estimated pose of a missing fiducial, in accordance with some embodiments of the present disclosure.

Figure 28:
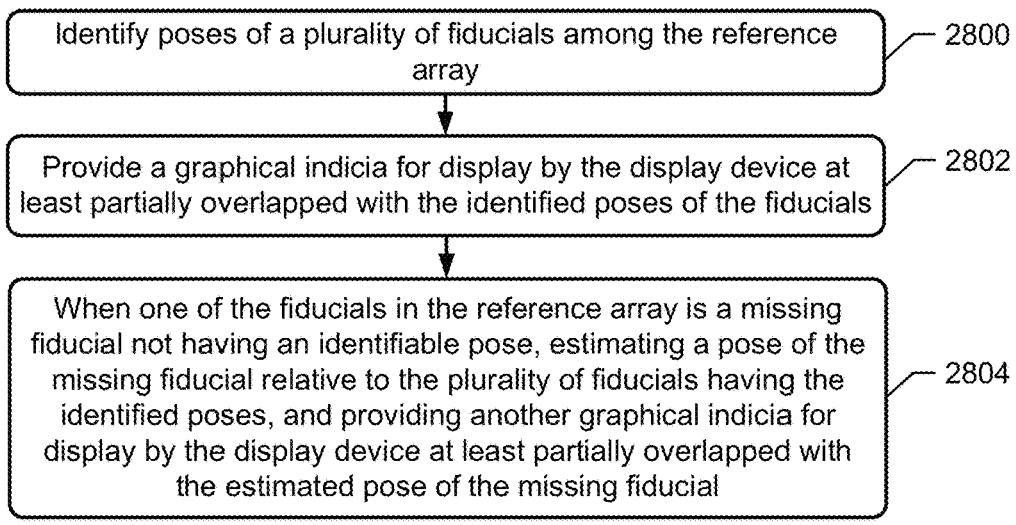
FIG. 28 illustrates a flowchart of operations performed by the camera tracking system to display the graphical indicia relative to the identified and missing fiducials, such as shown in FIG. 27, in accordance with some embodiments of the present disclosure.

FIG. 28 illustrates a flowchart of operations performed by the camera tracking system to display the graphical indicia relative to the identified and missing fiducials, such as shown in FIG. 27, in accordance with some embodiments of the present disclosure.

Referring to FIGS. 27 and 28, the camera tracking system is further configured to identify 2800 poses of a plurality of fiducials among the reference array 2102. For each of the plurality of fiducials among the reference array 2102 having the identified poses, the camera tracking system provides 2802 a graphical indicia (e.g., 2700, 2702, 2704, and 2706) for display by the display device of the XR headset 920 at least partially overlapped with the identified pose of the fiducial. The camera tracking system may be further configured to respond to when one of the fiducials in the reference array 2102 is a missing fiducial not having an identifiable pose, by estimating 2804 a pose of the missing fiducial relative to the plurality of fiducials having the identified poses, and providing 2804 another graphical indicia 2710 for display by the display device of the XR headset 920 at least partially overlapped with the estimated pose of the missing fiducial. A process to estimate 2804 the pose of the missing fiducial may be performed based on comparing the presently identified poses of the fiducials 2700-2706 to a defined template of the relative poses of the fiducials of the identified reference array 2102, to estimate a present pose of the missing fiducial. In this manner, a surgeon can intuitively identify which fiducials are being properly tracked by the tracking cameras and can also identify which, if any fiducials, are not being properly tracked. When, for example, the missing fiducial is excessively obscured by body fluid or other material, the surgeon can remedy the situation to enable accurate tracking of the reference array 2102.

Some further embodiments are directed to avoiding interpretation of a user's hand movements while holding a surgical tool as being a user's attempt to provide input to a hand-tracking input interface. This can be particularly important while a surgeon is holding a surgical tool because the tracking cameras may not maintain a sufficient view of the hands during movement of the surgical tool, and which can result in inaccurate tracking of the hands and cause accidental interactions with the user interface. In accordance with these further embodiments, a hand-user-interface exclusion zone is defined relative to the reference array. While a user's hand is determined to be at least partially within the hand-user-interface exclusion zone, the hand tracking information is not used as input from the user to a user-interface.

Figure 29:
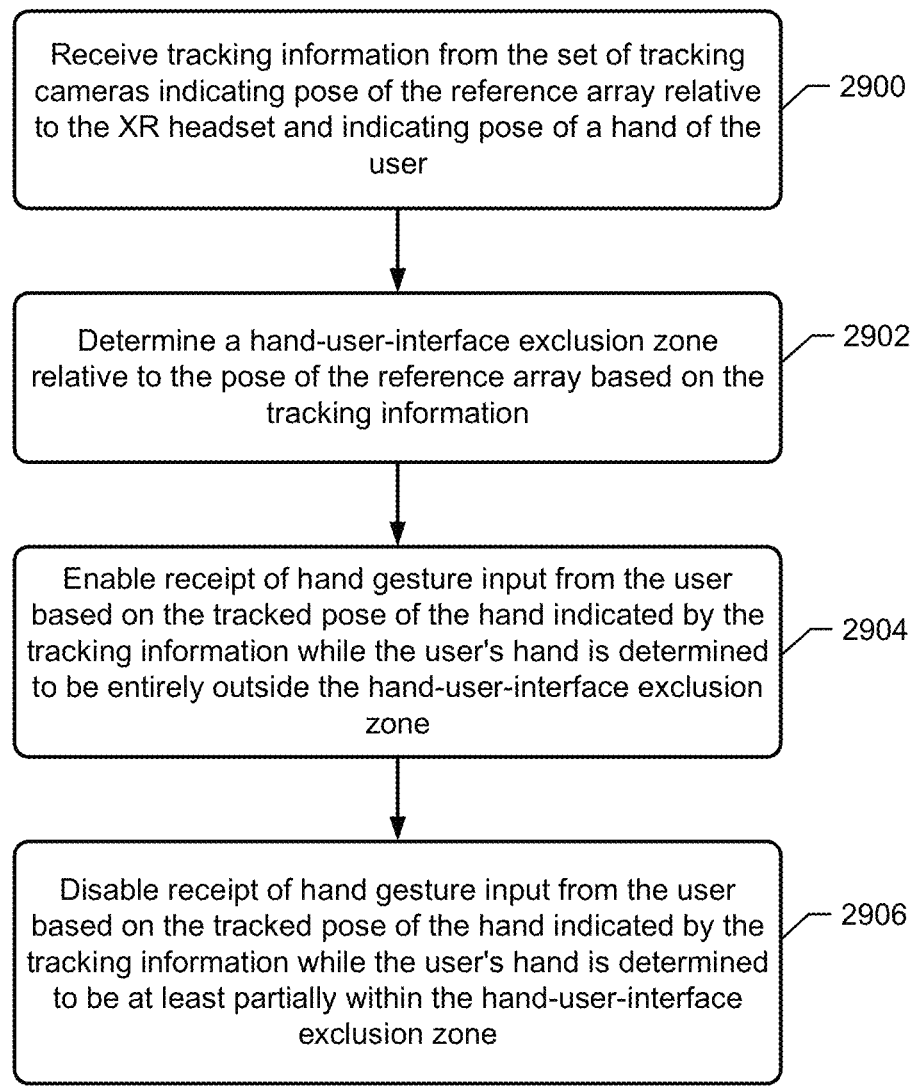
FIG. 29 illustrates a flowchart of operations performed by the camera tracking system to selectively enable receipt of hand gesture input based on whether the user's hand is at least partially within a hand-user-interface exclusion zone determined relative to the reference array, in accordance with some embodiments of the present disclosure.
Figure 30:
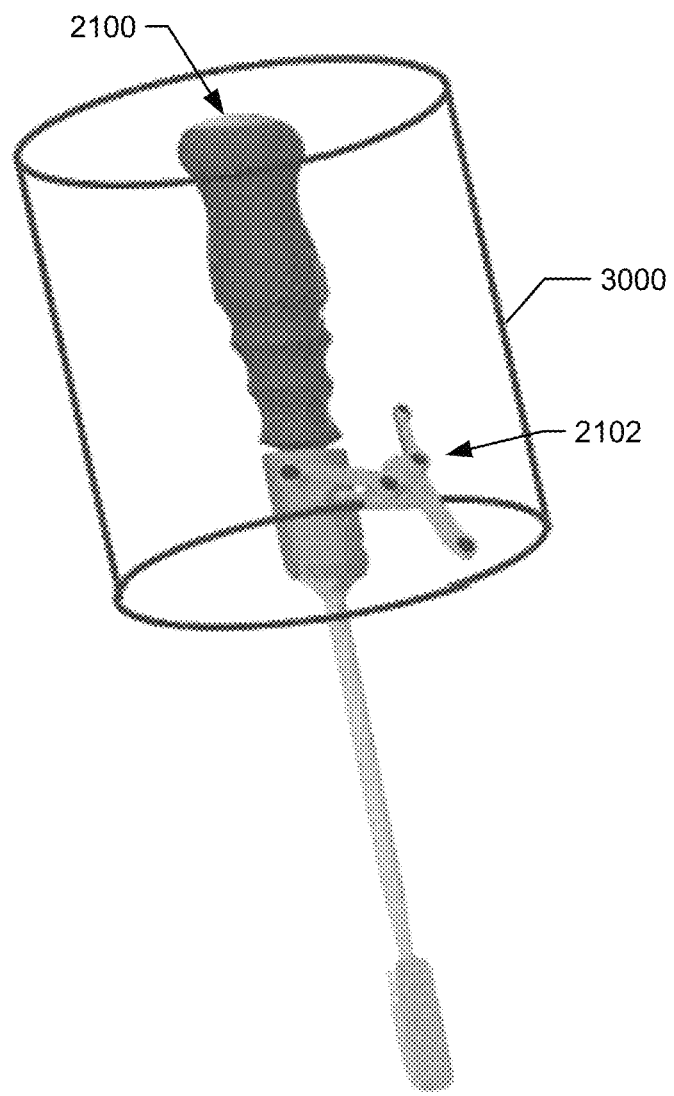
FIG. 30 illustrates a hand-user-interface exclusion zone determined relative to the reference array in accordance with some embodiments of the present disclosure.

FIG. 29 illustrates a flowchart of operations performed by the camera tracking system to selectively enable receipt of hand gesture input based on whether the user's hand is at least partially within a hand-user-interface exclusion zone determined relative to the reference array, in accordance with some embodiments of the present disclosure. FIG. 30 illustrates a hand-user-interface exclusion zone 3000 that is determined relative to the reference array 2102 connected to the surgical tool 2100, in accordance with some embodiments of the present disclosure.

Referring to FIG. 29, the camera tracking system is configured to receive 2900 tracking information from the set of tracking cameras indicating pose of the reference array 2102 relative to the XR headset and pose of a hand of the user. The camera tracking system determines 2902 the hand-user-interface exclusion zone 3000 relative to the pose of the reference array 2102 based on the tracking information. The camera tracking system enables 2904 receipt of hand gesture input from the user based on the tracked pose of the hand indicated by the tracking information while the user's hand is determined to be entirely outside the hand-user-interface exclusion zone 3000. In contrast, the camera tracking system disables 2906 receipt of hand gesture input from the user based on the tracked pose of the hand indicated by the tracking information while the user's hand is determined to be at least partially within the hand-user-interface exclusion zone 3000. Thus, while the user's hand is outside the exclusion zone 3000 the camera tracking system may interpret movement of the user's hand as gesture input being provided to, for example, select among the displayed list 1910 of modes that are displayed as shown in FIG. 19 in virtual space adjacent to the surgical tool 1900. In contrast, while the user's hand is at least partially within the exclusion zone 3000, such as while holding the surgical tool 2100, the camera tracking system prevents interpretation of movement of the user's hand as a gesture input to the system and would thereby, for example, not enable a user to use a hand gesture to select among the displayed list 1910 of modes.

Although various embodiments have been described in the context of using a set of tracking cameras on and XR headset, these and other embodiments can be used with any form of tracking cameras such as the set of tracking cameras on an auxiliary tracking bar and/or on another XR headset. Thus, in some embodiments, the set of tracking cameras are separate and spaced apart from the XR headset while the camera tracking system is receiving the tracking information from the set of tracking cameras. Various operations disclosed herein for pose chaining may be used to track poses of a reference array and/or a user's hand.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A camera tracking system for computer assisted navigation during surgery, the camera tracking system configured to:
   automatically initiate a registration process when a reference array of a surgical tool is brought into in a field of view of a set of tracking cameras attached to an extended reality (XR) headset;
   automatically identify the reference array of the surgical tool for tracking by the set of tracking cameras attached to the extended reality (XR) headset adapted to be worn by a user, the set of tracking cameras of the XR headset adapted for tracking the surgical tools and supplementing a main navigation system having a plurality of cameras for tracking the same surgical tools and an anatomical structure of a patient;

automatically determine whether the identified reference array captured by the tracking cameras of the XR headset is registered as being paired with characteristics of one of the surgical tools defined in a surgical tool database;

based on the reference array being determined to not be registered, provide to the display device a list of at least some of the plurality of the surgical tools defined in the surgical tool database for the user to select the one of the surgical tools to be registered as paired with the reference array;

based on the reference array being determined to not be registered and receiving user input, register the reference array as paired with characteristics of one of the surgical tools selected based on the user input, wherein the user input is in the form of one or more hand gestures recognizable by the set of tracking cameras of the XR headset; and provide a representation of the characteristics to a display device of the XR headset for display to the user.

2. The camera tracking system of claim 1, further configured to:
determine the user's selection among the displayed list of the one of the surgical tools to be registered as paired with the reference array, based on tracking information from the set of tracking cameras indicating pose of a hand of the user in XR space relative to the displayed list.

3. The camera tracking system of claim 1, further configured to:
receive tracking information from the set of tracking cameras indicating pose of the reference array relative to the XR headset;
determine a pose for where the representation of the characteristics is to be displayed relative to the reference array based on the tracking information; and
control the XR headset to display the representation of the characteristics with the determined pose relative to the reference array.

4. The camera tracking system of claim 1, further configured to:
obtain tracking accuracy information characterizing accuracy at which the set of tracking cameras is presently tracking pose of the reference array; and
provide an indication of the tracking accuracy information to the display device of the XR headset for display to the user.

5. The camera tracking system of claim 1, further configured to:
obtain a graphical representation of the one of the plurality of surgical tools in at least 2-dimensions;
receive tracking information from the set of tracking cameras indicating pose of the reference array relative to the XR headset;
determine a pose for the graphical representation based on the tracking information; and provide the graphical representation as the representation of the characteristics to the display device of the XR headset for display with the determined pose.

6. The camera tracking system of claim 1, further configured to:
obtain a last verified date which indicates when the one of the surgical tools was last verified to not have structural deformation; and
provide an indication of the last verified date to the display device of the XR headset for display to the user.

7. The camera tracking system of claim 1, further configured to:
determine when the reference array has been brought within an inspection region which is defined relative to location of the XR headset;
responsive to determining that the reference array has been brought within the inspection region, initiate the determination of whether the reference array is registered as being paired with characteristics of one of a plurality of surgical tools defined in the surgical tool database; and
limit operation to receive user input to register the reference array as paired with characteristics of one of the plurality of surgical tools defined in the surgical tool database, to occur only while the reference array remains within the inspection region.

8. The camera tracking system of claim 1, further configured to:
determine when the reference array has been brought within an inspection region which is defined relative to location of the XR headset;
responsive to determining that the reference array has been brought within the inspection region, initiate the providing of the representation of the characteristics to the display device of the XR headset for display to the user; and
responsive to determining that the reference array has exited the inspection region, cease any ongoing providing of the representation of the characteristics to the display device of the XR headset for display to the user.

9. The camera tracking system of claim 1, further configured to:
identify poses of a plurality of fiducials among the reference array; and
for each of the plurality of fiducials among the reference array having the identified poses, providing a graphical indicia for display by the display device at least partially overlapped with the identified pose of the fiducial.

10. The camera tracking system of claim 9, further configured to:
when one of the fiducials in the reference array is a missing fiducial not having an identifiable pose, estimating a pose of the missing fiducial relative to the plurality of fiducials having the identified poses, and providing another graphical indicia for display by the display device at least partially overlapped with the estimated pose of the missing fiducial.

11. The camera tracking system of claim 1, further configured to:
receive tracking information from the set of tracking cameras indicating pose of the reference array relative to the XR headset and pose of a hand of the user;
determine a hand-user-interface exclusion zone relative to the pose of the reference array based on the tracking information;
enable receipt of hand gesture input from the user based on the tracked pose of the hand indicated by the tracking information while the user's hand is determined to be entirely outside the hand-user-interface exclusion zone; and
disable receipt of hand gesture input from the user based on the tracked pose of the hand indicated by the tracking information while the user's hand is determined to be at least partially within the hand-user-interface exclusion zone.

12. A computer program product comprising a non-transitory computer readable medium storing program code executable by at least one processor of a camera tracking system for computer assisted navigation surgery to:
  automatically initiate a registration process when a reference array of a surgical tool is brought into in a field of view of a set of tracking cameras attached to an extended reality (XR) headset;
  automatically identify the reference array of the surgical tool for tracking by the set of tracking cameras attached to the extended reality (XR) headset adapted to be worn by a user when the reference array is brought into a field of view of the set of tracking cameras, the set of tracking cameras of the XR headset adapted for tracking the surgical tools and supplementing a main navigation system having a plurality of cameras for tracking the same surgical tools and an anatomical structure of a patient;
  automatically determine whether the identified reference array captured by the tracking cameras of the XR headset is registered as being paired with characteristics of one of the surgical tools defined in a surgical tool database;
  based on the reference array being determined to not be registered, provide to the display device a list of at least some of the plurality of the surgical tools defined in the surgical tool database for the user to select the one of the surgical tools to be registered as paired with the reference array;
  based on the reference array being determined to not be registered and receiving user input through the XR headset, register the reference array as paired with characteristics of one of the surgical tools selected based on the user input, wherein the user input is in the form of one or more hand gestures recognizable by the set of tracking cameras of the XR headset; and
  provide a representation of the characteristics to a display device of the XR headset for display to the user.

13. The computer program product on non-transitory computer readable medium of claim 12, wherein the program code executable by the at least one processor of the camera tracking system is further configured to:
  receive tracking information from the set of tracking cameras indicating pose of the reference array relative to the XR headset;
  determine a pose for where the representation of the characteristics is to be displayed relative to the reference array based on the tracking information; and
  control the XR headset to display the representation of the characteristics with the determined pose relative to the reference array.

14. The computer program product on non-transitory computer readable medium of claim 12, wherein the program code executable by the at least one processor of the camera tracking system is further configured to:
  obtain tracking accuracy information characterizing accuracy at which the set of tracking cameras is presently tracking pose of the reference array; and
  provide an indication of the tracking accuracy information to the display device of the XR headset for display to the user.

15. The computer program product on non-transitory computer readable medium of claim 12, wherein the program code executable by the at least one processor of the camera tracking system is further configured to:
  obtain a graphical representation of the one of the plurality of surgical tools in at least 2-dimensions;
  receive tracking information from the set of tracking cameras indicating pose of the reference array relative to the XR headset;
  determine a pose for the graphical representation based on the tracking information; and
  provide the graphical representation as the representation of the characteristics to the display device of the XR headset for display with the determined pose.

16. The computer program product on non-transitory computer readable medium of claim 12, wherein the program code executable by the at least one processor of the camera tracking system is further configured to:
  determine when the reference array has been brought within an inspection region which is defined relative to location of the XR headset;
  responsive to determining that the reference array has been brought within the inspection region, initiate the determination of whether the reference array is registered as being paired with characteristics of one of a plurality of surgical tools defined in the surgical tool database; and
  limit operation to receive user input to register the reference array as paired with characteristics of one of the plurality of surgical tools defined in the surgical tool database, to occur only while the reference array remains within the inspection region.

17. The computer program product on non-transitory computer readable medium of claim 12, wherein the program code executable by the at least one processor of the camera tracking system is further configured to:
  identify poses of a plurality of fiducials among the reference array; and
  for each of the plurality of fiducials among the reference array having the identified poses, providing a graphical indicia for display by the display device at least partially overlapped with the identified pose of the fiducial.

18. A method by a camera tracking system for computer assisted navigation during surgery, the method comprising:
  automatically initiating a registration process when a reference array of a surgical tool is brought into in a field of view of a set of tracking cameras attached to an extended reality (XR) headset;
  identifying a reference array of a surgical tool tracked by a set of tracking cameras attached to an extended reality (XR) headset adapted to be worn by a user, the set of tracking cameras of the XR headset adapted for tracking the surgical tools and supplementing a main navigation system having a plurality of cameras for tracking the same surgical tools and an anatomical structure of a patient;
  automatically determining whether the identified reference array captured by the tracking cameras of the XR headset is registered as being paired with characteristics of one of the surgical tools defined in a surgical tool database;
  based on the reference array being determined to not be registered, providing to the display device a list of at least some of the plurality of the surgical tools defined in the surgical tool database for the user to select the one of the surgical tools to be registered as paired with the reference array;
  based on the reference array being determined to not be registered and receiving user input, registering the reference array as paired with characteristics of one of the surgical tools selected based on the user input, wherein the user input is in the form of one or more hand gestures recognizable by the set of tracking cameras of the XR headset; and providing a representation of the characteristics to a display device of the XR headset for display to the user.

\* \* \* \* \*